United States Patent
Takeda et al.

(10) Patent No.: US 9,815,812 B2
(45) Date of Patent: Nov. 14, 2017

(54) THIOPYRANOSE COMPOUND AND METHOD FOR PRODUCING SAME

(71) Applicant: FUJIFILM Corporation, Tokyo (JP)

(72) Inventors: Akira Takeda, Kanagawa (JP); Toru Watanabe, Kanagawa (JP); Taiji Katsumata, Kanagawa (JP); Takayuki Ito, Kanagawa (JP); Toshihiko Sawada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/238,784

(22) Filed: Aug. 17, 2016

(65) Prior Publication Data

US 2016/0355497 A1 Dec. 8, 2016

Related U.S. Application Data

(63) Continuation of application No. PCT/JP2015/052304, filed on Jan. 28, 2015.

(30) Foreign Application Priority Data

Feb. 19, 2014 (JP) .................................. 2014-029978

(51) Int. Cl.
| | | |
|---|---|---|
| *C07D 335/02* | (2006.01) | |
| *C07C 69/63* | (2006.01) | |
| *C07C 69/78* | (2006.01) | |
| *C07C 309/68* | (2006.01) | |
| *C07C 309/73* | (2006.01) | |
| *C07H 1/00* | (2006.01) | |
| *C07H 5/10* | (2006.01) | |
| *C07H 13/08* | (2006.01) | |
| *C07H 15/18* | (2006.01) | |

(52) U.S. Cl.
CPC ............ *C07D 335/02* (2013.01); *C07C 69/63* (2013.01); *C07C 69/78* (2013.01); *C07C 309/68* (2013.01); *C07C 309/73* (2013.01); *C07H 1/00* (2013.01); *C07H 5/10* (2013.01); *C07H 13/08* (2013.01); *C07H 15/18* (2013.01)

(58) Field of Classification Search
CPC .................................................. C07D 335/02
USPC .......................................................... 549/28
See application file for complete search history.

(56) References Cited

U.S. PATENT DOCUMENTS

| | | |
|---|---|---|
| 3,116,282 A | 12/1963 | Hunter |
| 3,243,425 A | 3/1966 | Whistler |
| 4,211,773 A | 7/1980 | Lopez et al. |
| 4,220,774 A | 9/1980 | Kuehne |
| 4,803,272 A | 2/1989 | Anton et al. |
| 5,811,408 A | 9/1998 | Yoshimura et al. |
| 6,103,707 A | 8/2000 | Yamada et al. |
| 6,147,058 A | 11/2000 | Yoshimura et al. |
| 6,448,415 B1 | 9/2002 | Lee et al. |
| 7,148,223 B2 | 12/2006 | Secrist, III et al. |
| 8,329,925 B2 | 12/2012 | Voigtländer et al. |
| 8,420,831 B2 | 4/2013 | Voigtländer et al. |
| 9,221,865 B2 | 12/2015 | Nakamura et al. |
| 9,475,835 B2 | 10/2016 | Nakamura et al. |
| 2006/0142238 A1 | 6/2006 | McGuigan |
| 2009/0069263 A1 | 3/2009 | Damha et al. |
| 2013/0252918 A1 | 9/2013 | McGuigan |
| 2015/0011499 A1 | 1/2015 | Baba et al. |
| 2016/0362389 A1 | 12/2016 | Nakamura et al. |

FOREIGN PATENT DOCUMENTS

| | | |
|---|---|---|
| CN | 101058557 A | 10/2007 |
| CN | 101200463 A | 6/2008 |
| EP | 0841344 A1 | 5/1998 |
| EP | 2883866 A1 | 6/2015 |

(Continued)

OTHER PUBLICATIONS

King, Med. Chem., Principle and Practice (1994), pp. 206-208.*
Communication dated Dec. 22, 2016, from the European Patent Office in counterpart European application No. 15751531.3.
Cox, J.M., et al., "Cyclic Hemithioacetals: Analogues of Thiosugars with Sulphur in the Ring", J. Chem. Soc., Section C, 1967, pp. 1130-1134.
International Search Report, issued by International Searching Authority in corresponding International Application No. PCT/JP2015/052304, dated Mar. 10, 2015.
Hua Lin et al. "Highly Efficient Asymmetric Synthesis of Enantiopure Dihydro-1, 2-oxazines: Dual-Organocatalyst-Promoted Asymmetric Cascade Reaction" Organic Letters (2012), vol. 14, No. 15; pp. 3818-3821.

(Continued)

*Primary Examiner* — Taofiq A Solola
(74) *Attorney, Agent, or Firm* — Sughrue Mion, PLLC

(57) ABSTRACT

There is provided a production method of a thiopyranose compound represented by the following Formula (2) by reacting a compound represented by the following Formula (1) with a sulfur compound.

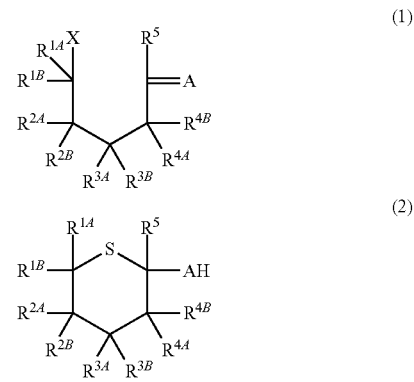

X represents a leaving group. A represents an oxygen atom or a sulfur atom. Further, each of $R^{1A}$ to $R^{4B}$, $R^{1B}$ to $R^{4B}$, and $R^5$ represents a hydrogen atom or a specific substituent.

21 Claims, No Drawings

(56) References Cited

FOREIGN PATENT DOCUMENTS

| | | |
|---|---|---|
| JP | 53-119810 A | 10/1978 |
| JP | 55-49395 A | 4/1980 |
| JP | 56-92239 A | 7/1981 |
| JP | 5-178875 A | 7/1993 |
| JP | 6-501261 A | 2/1994 |
| JP | 8-53490 A | 2/1996 |
| JP | 8-504753 A | 5/1996 |
| JP | 10-282039 A | 10/1998 |
| JP | 2003-172990 A | 6/2003 |
| JP | 2005-503358 A | 2/2005 |
| JP | 2006-335737 A | 12/2006 |
| JP | 2006-528162 A | 12/2006 |
| JP | 2007-514643 A | 6/2007 |
| JP | 4202327 B2 | 12/2008 |
| JP | 2010-59173 A | 3/2010 |
| JP | 2011-526242 A | 10/2011 |
| JP | 2013-514260 A | 4/2013 |
| JP | 2013-540129 A | 10/2013 |
| WO | 91/04982 A1 | 4/1991 |
| WO | 94/05687 A1 | 3/1994 |
| WO | 96/01834 A1 | 1/1996 |
| WO | 97/37993 A1 | 10/1997 |
| WO | 97/38001 A1 | 10/1997 |
| WO | 97/49716 A1 | 12/1997 |
| WO | 99/28312 A1 | 6/1999 |
| WO | 99/43690 A1 | 9/1999 |
| WO | 03/000200 A2 | 1/2003 |
| WO | 2004/014930 A1 | 2/2004 |
| WO | 2004/014931 A1 | 2/2004 |
| WO | 2004/027658 A1 | 4/2004 |
| WO | 2004/100891 A2 | 11/2004 |
| WO | 2004/106352 A1 | 12/2004 |
| WO | 2006/073197 A1 | 7/2006 |
| WO | 2007/068113 A1 | 6/2007 |
| WO | 2011/074484 A1 | 6/2011 |
| WO | 2013/146833 A1 | 10/2013 |
| WO | 2014/027658 A1 | 2/2014 |

OTHER PUBLICATIONS

Wu-Bao Wang et al. "A Practical Synthesis of Sugar-Derived Cyclic Nitrones: Powerful Synthons for the Synthesis of Iminosugars" Synlett, 2010, No. 3; pp. 488-492.
David A. Berges et al. "Bicyclic diazasugars. Part 3: β-D-Mannose and 6-deoxy-β-L-gulose analogues" Tetrahedron, 2001, vol. 57; pp. 9915-9924.
Ronald C. Horton Jr. et al "Aldehyde-Terminated Self-Assembled Monolayers on Gold: Immobilization of Amines onto Gold Surfaces" J. Am. Chem. Soc., 1997, vol. 119; pp. 12980-12981.
H. Driguez et al. "A Novel Synthesis of 5-Thio-D-Glucose" Tetrahedron Letters, 1981, vol. 22, No. 50, pp. 5061-5062.
R. M. Rowell et al. "Derivatives of α-D-Glucothiopyranose" J. Org. Chem., 1996, vol. 31; pp. 1514-1516.
Eva Bozo et al. "Synthesis of 4-cyanophenyl and 4-nitrophenyl 1,5-dithio-L-and -D-arabinopyranosides possessing antithrombotic activity[1,2]" Carbohydrate Research 1998, vol. 311; pp. 191-202.
International Preliminary Report on Patentability issued from the International Bureau in counterpart International Application No. PCT/JP2015/052304, dated Feb. 16, 2016.
Johan Fanton et al: "Enzymatic and Organocatalyzed Asymmetric Aldolization Reactions for the Synthesis of Thiosugar Scaffolds", Eur. Journal Org. Chem. 2012, pp. 203-210.
Junji Fujita et al. "Synthesis of thiosaccharides employing the Pummerer rearrangement of tetrahydrothiopyran oxides" Tetrahedron 2004, vol. 60, No. 32, pp. 6829-6851.
Dusan Miljkovic et al. "An improved synthesis of methyl 5-thio-D-arabino-pyranosides" Journal of the Serbian Chemical Society, vol. 55, 1990; pp. 359-361.
Hironobu Hashimoto et al. "Novel conversion of aldopyranosides into 5-thioaldopyranosides via acyclic monothioacetals with inversion and retention of configuration at C-5" Carbohydrate Research, vol. 282, Issue 2 (Feb. 23, 1996) pp. 207-221.
Communication dated Apr. 4, 2017 from the Japanese Patent Office in counterpart application No. 2014-029978.
Communication dated Mar. 28, 2017 from the European Patent Office in counterpart application No. 15751531.3.
Communication dated Mar. 13, 2017 from the U.S. Patent and Trademark Office in U.S. Appl. No. 15/238,232.
Communication dated Apr. 18, 2017 from the Japanese Patent Office in application No. 2016-504110.
Communication dated Jan. 31, 2017 from the European Patent Office in application No. 15751503.2.
Communication dated Mar. 24, 2015 from the U.S. Patent and Trademark Office in U.S. Appl. No. 14/621,119.
Communication dated Jul. 2, 2015 from the U.S. Patent and Trademark Office in U.S. Appl. No. 14/621,119.
Communication dated Nov. 30, 2015 from the U.S. Patent and Trademark Office in U.S. Appl. No. 14/621,119.
Communication dated Feb. 8, 2016 from the U.S. Patent and Trademark Office in U.S. Appl. No. 14/873,966.
Communication dated May 26, 2016 from the U.S. Patent and Trademark Office in U.S. Appl. No. 14/873,966.
Communication dated Jul. 6, 2016 from the U.S. Patent and Trademark Office in U.S. Appl. No. 14/873,966.
Communication dated Sep. 12, 2016 from the U.S. Patent and Trademark Office in U.S. Appl. No. 14/873,966.
Vorbruggen et al., Org. Reactions (2000), pp. 55.
Watts et al., Nuclei. Acids Res. (2007) vol. 35(5), pp. 1441-1451.
Karrer, Org Chem. 2nd Ed. (1996). pp. 92-102.
Kamal N. Tiwari et al. "Synthesis and Biological Activity of 4'-Thio-L-Xylofuranosyl Nucleosides" Nucleosides, Nucleotides & Nucleic Acids, 20(4-7), 2001, pp. 743-746 (4 pages total).
Kamal N. Tiwari et al. "The Synthesis and Biological Activity of 1-(2-Deoxy-4-Thio-a-L-Threo-Pentofuranosyl) Thymine" Nucleosides & Nucleotides, 12(8), pp. 841-846 (1993).
Hiroshi Satoh et al. "Synthesis of L-Enantiomers of 4'-Thioarabinofuranosyl Pyrimidine Nucleosides" Bioorganic & Medicinal Chemistry Letters 8 (1998) pp. 989-992.
Yuichi Yoshimura et al. "A Facile, Alternative Synthesis of 4'-Thioarabinonucleosides and their Biological Activities" J. Med. Chem. 1997, 40(14); pp. 2177-2183.
Yun-Lung Fu et al. "An Alternative Synthesis of Anomeric Methyl 2-Deoxy-4-thio-D-erythro-pentofuranosides" J. Org. Chem., vol. 41 No. 24; 1976, pp. 3831-3834 (4 pages total).
John A. Secrist III et al. "Synthesis and Biological Activity of 2'-Deoxy-4'-thio Pryimidine Nucleosides" J. Med. Chem. 1991, 34, No. 8 (pp. 2361-2366).
International Search Report, issued by International Searching Authority dated May 19, 2015, in International Application No. PCT/JP2015/054305.
Martin W. Bredenkamp et al. "Stannylene Directed Selective Acylation of Some Open-Chain L-Arabinose Derivatives" Tetrahedron Letters, 1990, 31(19) pp. 2759-2762.
Elmer J. Reist et al. "Thio Sugars, Synthesis of the Adenine Nucleosides of 4-Thio-D-Xylose and 4-Thio-D-Arabinose" Journal of Organic Chemistry, 1968, 33(1) pp. 189-192.
Elmer J. Reist et al. "Synthesis the 4-Thio-D-and-L-Ribofuranose and the Corresponding Adenine Nucleosides" Journal of the American Chemical Society, 1964, 86(24), pp. 5658-5663.
Stephanie A. Hartsel et al. "Synthesis of 9-(4-Thioxylofuranosyl) adenine via a Novel Glycosylation Reaction" Tetrahedron Letters 39 (1998) pp. 205-208.
Vjera Pejanovic et al. "Synthesis and Biological Evaluation of Some Novel 4'-Thio-L-ribonucleosides with Modified Nucleobase Moieties" Bioorganic & Medicinal Chemistry Letters, 2003, 13(11) pp. 1849-1852.
Kamal N. Tiwari et al. "Synthesis and Anti-cancer Activity of Some Novel 5-Azacytosine Nucleosides" Nucleosides, Nucleotides & Nucleic Acids, 2003, 22(12), pp. 2161-2170.
International Preliminary Report on Patentability issued from the International Bureau in International Application No. PCT/JP2015/054305, dated Jan. 4, 2016.

(56) References Cited

OTHER PUBLICATIONS

Peter Haeberli et al. "Syntheses of 4'-thioribonucleosides and thermodynamic stability and crystal structure of RNA oligomers with incorporated 4'-thiocytosine" Nucleic Acids Research, 2005, vol. 33 No. 13; pp. 3965-3975.
Yuichi Yoshimura et al. "An Alternative Synthesis of the Antineoplastic Nucleoside 4'-ThioFAC and Its Application to the Synthesis of 4'-ThioFAG and 4'-Thiocytarazid" Journal of Organic Chemistry, 1999, vol. 64 No. 21; pp. 7912-7920.
G. Inguaggiato et al. "Novel Triazole 2'-Deoxy-4'-Thionucleosides: Stereoselective Synthesis and Biological Evaluation" Nucleosides & Nucleotides, 1999; vol. 18 No. 3; pp. 457-467.
Houssine Ait-sir et al;. "Synthesis and configurational assignments of 3-substituted 2-deoxy-4-thio-D erythro-pentofuranose derivatives" Journal of the Chemical Society, Perkin transactions 1, 1996; No. 14; pp. 1665-1671.
Johan Fanton et al. "Enzymatic and Organocatalyzed Asymmetric Aldolization Reactions for the Synthesis of Thiosugar Scaffolds" European Journal of Organic Chemistry 2012, No. 1; pp. 203-210.
Choo et al., "Synthesis, Anti-HIV Activity, and Molecular Mechanism of Drug Resistance of L-2',3'-Didehydro-2',3'-dideoxy-2'-fluoro-4'-thionucleosides," Journal of Medicinal Chemistry, 2003, vol. 46, No. 3, pp. 389-398.
Cottrell et al., "Reactions of Sugar Chlorosulfates VII. Some Conformational Aspects," Canadian Journal of Chemistry, Jul. 1, 1966, vol. 44, No. 13, pp. 1483-1491.
International Search Report issued in PCT/JP2013/071871, dated Nov. 26, 2013.
Jean-Baptiste et al., "Synthesis of 2',3'-Dideoxy-2'-Fluoro-4'-Thionucleosides from a Fluoroxanthate," Synlett, 2008, No. 6, pp. 817-820.
Kawana et al., "The Synthesis of 2',3'-Dideoxycytidine and Its 2'-Azido Analogue. Applications of the Deoxygenative [1,2]-Hydride Shift of Sulfonates with Mg(OMe) 2-NaBH4," The Chemical Society of Japan, Chemistry Letters, 1987, pp. 2419-2422.
Khare et al., "Synthesis of 4-deoxy-4-thioarabinofuranosyl disaccharides, analogs of Mycobacterial arabinogalactan," Indian Journal of Chemistry, vol. 47B. Nov. 2008, pp. 1748-1752.
Ototani et al., "Preparation and Antitumor Activity of 4 '-Thio Analogs of 2,2'-Anhydro-1-B-D-arabinofuranosylcytosine," Journal of Medicinal Chemistry, 1974, vol. 17, No. 5, pp. 535-537.
Yoshimura et al., "An Alternative Synthesis of the Antineoplastic Nucleoside 4'-ThioFAC and Its Application to the Synthesis of 4'-ThioFAG and 4'-Thiocytarazid," J. Org. Chem., 1999, vol. 64, No. 21, pp. 7912-7920.
Zheng et al, "Synthesis of L•11-3'-Deoxy-3',3'-difluoro-4'-thionucleosides," Organic Letters, 2006, vol. 8, No. 26, pp. 6083-6086.
Canadian Office Action for Application No. 2,880,794, dated Nov. 2, 2015.
International Preliminary Report on Patentability and Written Opinion of the International Searching Authority (forms PCT/IB/338, PCT/IB/373, PCT/ISA/237 and PCT/IB/326), dated Feb. 26, 2015, for International Application No. PCT/JP2013/071871, along with English translations.
Canadian Office Action issued in Application No. 2,880,794 dated Aug. 18, 2016.
Australian Office Action for Application No. 2013303534 dated Dec. 1, 2015.
Chinese Office Action for Application No. 201380042642.1, dated Nov. 2, 2015 with English language translation.
Extended European Search Report for Application No. 13879640.4 dated May 18, 2016.
Japanese Office Action for Application No. 2014-530560 dated Mar. 1, 2016 with English language translation.
Korean Office Action for Application No. 10-2015-7003655, dated May 12, 2016 with English language translation.
Partial Supplementary European Search Report issued in Application No. 13879640.4, dated Feb. 16, 2016.
Russian Office Action for Application No. 2015108790, dated Apr. 25, 2016 with English language translation.
Yoshimura et al., "Synthetic Studies on 2'-Substituted-4'-Thiocytidine Derivatives as Antineoplastic Agents", Nucleosides & Nucleotides, vol. 18, No. 4/5. Jan. 1, 1999, pp. 815-820.
Attardo et al., "Efficient Synthesis of 5,8-Disubstituted-1,4-Dihydrobenzoxathiin-3-Oxides and Their Isomeric Structures, 4,7-Disubstituted-1,3-Dihydrobenzo[b] Thiophene-2,2-Dioxides," Tetrahedron Letters, vol. 35, No. 27, 1994, pp. 4743-4746.
Australian Office Action for Australian Application No. 2013241341, dated Oct. 5, 2015.
Baker et al., "Large-Scale Preparation of D-allose: Observations on the Stereoselectivity of the Reduction of 1,2:5,6-di-O-isopropylidene-a-D-ribo-hexofuranos-3-ulose hydrate," Carbohydrate Research, vol. 24, 1972, pp. 192-197.
Berge et al., "Pharmaceutical Salts," Journal of Pharmaceutical Sciences, vol. 66, No. 1, Jan. 1977, pp. 1-19.
Canadian Office Action for Canadian Application No. 2,865,742, dated Mar. 29, 2016.
Chinese Office Action and Search Report for Chinese Application No. 201380016308.9, dated Jul. 1, 2015, with an English translation of the Chinese Office Action.
European Office Action for corresponding European Application No. 13879640.4, dated May 8, 2017.
European Office Action for European Application No. 13770090.2, dated May 19, 2017.
Extended European Search Report for European Application No. 13770090.2, dated Oct. 12, 2015.
Fujita et al., "Gene Expression Levels as Predictive Markers of Outcome in Pancreatic Cancer after Gemcitabine-Based Adjuvant Chemotherapy", Neoplasia, vol. 12, No. 10, Oct. 2010, pp. 807-817 (13 pages total).
Hertel et al., "Evaluation of the Antitumor Activity of Gemcitabine (2',2'-Difluoro-2'-deoxycytidine)," Cancer Research, vol. 50, Jul. 15, 1990, pp. 4417-4422 (7 pages total).
International Preliminary Report on Patentability and Written Opinion of the International Searching Authority (Forms PCT/IB/326, PCT/IB/373 and PCT/ISA/237) for International Application No. PCT/JP2010/072182, dated Jun. 19, 2012.
International Preliminary Report on Patentability and Written Opinion of the International Searching Authority (Forms PCT/IB/326, PCT/IB/373, PCT/ISA/237 and PCT/IB/338) for International Application No. PCT/JP2013/058896, dated Oct. 1, 2014, with an English translation of the Written Opinion.
International Preliminary Report on Patentability and Written Opinion of the International Searching Authority (Forms PCT/IB/338, PCT/ISA/237, PCT/IB/326 and PCT/IB/373) for International Application No. PCT/JP2015/080885, dated May 2, 2017, with an English translation of the Written Opinion.
International Search Report and Written Opinion of the International Searching Authority (Forms PCT/ISA/210 and PCT/ISA/237) for International Application No. PCT/JP2010/072182, dated Apr. 29, 2011.
International Search Report and Written Opinion of the International Searching Authority (Forms PCT/ISA/210, PCT/ISA/220 and PCT/ISA/237) for International Application No. PCT/JP2013/058896, dated Jun. 4, 2013, with an English translation of the International Search Report.
International Search Report and Written Opinion of the International Searching Authority PCT/ISA/210, PCT/ISA/220 and PCT/ISA/237) for International Application No. PCT/JP2015/080885, dated Feb. 2, 2016, with an English translation of the International Search Report.
Israeli Office Action for Israeli Application No. 234222, dated Sep. 13, 2016, with an English translation.
Japanese Decision to Final Rejections for Japanese Application No. 2014-507938, dated Apr. 7, 2015, with an English translation.
Jeong et al., "NG-Substituted D-4'-Thioadenosine-5'-methyluronamides: Potent and Selective Agonists at the Human A3 Adenosine Receptor," J. Med. Chem., vol. 46, No. 18, 2003 (published online Aug. 6, 2003), pp. 3775-3777.
Jeong et al., Chemistry Letters, 1995, pp. 301-302.

(56) References Cited

OTHER PUBLICATIONS

Jeong et al., Tetrahedron Letters, vol. 35, No. 41, 1994, pp. 7569-7572.
Jeong et al., Tetrahedron Letters, vol. 35, No. 41, 1994, pp. 7573-7576.
Karrer, "Organic Chemistry," Second Edition, Elsevier Publ. Comp., Inc., New York, 1946, pp. 92-102 (pp. 91-93 provided) (6 pages total).
Komine et al., "Synthesis and Structure-Activity Relationship Studies of Highly Potent Novel Oxazolidinone Antibacterials," J. Med. Chem., vol. 51, No. 20, 2008 (published online Oct. 1, 2008), pp. 6558-6562.
Korean Notice of Final Rejection for Korean Application No. 10-2015-7003655, dated Nov. 21, 2016, with an English translation thereof.
Korean Notice of Submission of Opinion for Korean Application No. 10-2014-7030209, dated Oct. 25, 2016, with an English translation thereof.
Korean Notification of Reason for Refusal for Korean Application No. 10-2015-7003655, dated Jan. 11, 2017, with an English translation thereof.
Korean Office Action for Korean Application No. 10-2014-7030209, dated Apr. 3, 2017, with an English translation thereof.
Mercer et al., "Looking Glass Inhibitors: Both Enantiomeric N-benzyl Derivatives of 1,4-dideoxy-1,4-imino-D-lyxitol [A Potent Competitive Inhibitor of a-D-galactosidase] and . . . ," Tetrahedron: Asymmetry, vol. 20, 2009 (published online Oct. 29, 2009), pp. 2368-2373.
Mexican Office Action for Mexican Application No. MX/a/2014/011182, dated Apr. 26, 2017, with an English translation.
Miura et al., "Antitumor Activity of a Novel Orally Effective Nucleoside, 1-(2-deoxy-2-fluoro-4-thio-13-D-arabinofuranosyl)cytosine," Cancer Letters, vol. 129, 1998, pp. 103-110.
Miura et al., "Comparison of 1-(2-deoxy-2-fluoro-4-thio-(3-D-arabinofuranosyl)cytosine with Gemcitabine in its Antitumor Activity," Cancer Letters, vol. 144, 1999, pp. 177-182.
Miura et al., "Suppression of Peritoneal Dissemination by 4'-thio-FAC," Oncology Reports, vol. 9, No. 6, Nov.-Dec. 2002, pp. 1319-1322 (9 pages total).
New Zealand Office Action for New Zealand Application No. 701245, dated Aug. 21, 2015.
New Zealand Office Action for New Zealand Application No. 701245, dated Jan. 28, 2015.
Partial European Search Report for European Application No. 10163406.1, dated Nov. 24, 2010.
Plunkett et al., "Preclinical Characteristics of Gemcitabine," Anti-Cancer Drugs, vol. 6, Suppl, 6, 1995.
Russian Office Action and Search Report for Russian Application No. 2014143277, dated Nov. 5, 2015, with an English translation thereof.
Russian Office Action for Russian Application No. 2014143277, dated Mar. 21, 2016, with an English translation thereof.
Serajuddin, "Salt Formation to Improve Drug Solubility," Advanced Drug Delivery Reviews, vol. 59, 2007 (available online May 29, 2007), pp. 603-616.
Singaporean Office Action for Singaporean Application No. 11201406080V, dated Mar. 19, 2015.
Slusarczyk et al., "Application of ProTide Technology to Gemcitabine: A Successful Approach to Overcome the Key Cancer Resistance Mechanisms Leads to a New Agent (NUC-1031) in Clinical Development," J. Med. Chem., vol. 57, No. 4, Jan. 28, 2014, 1531-1542 (12 pages total).
Taiwanese Office Action and Search Report for Taiwanese Application No. 102110915, dated May 25, 2016, with an English translation thereof.
Taiwanese Office Action for Taiwanese Application No. 102110915, dated Sep. 30, 2016, with an English translation thereof.
Takahashi et al., "Synthesis and Crystal Structure of 2'-deoxy-2'-fluoro-4'-thioribonucleosides: Substrates for the Synthesis of Novel Modified RNAs," Tetrahedron, vol. 64, 2008 (published online Mar. 4, 2008), pp. 4313-4324.
U.S. Notice of Allowance for U.S. Appl. No. 12/959,735, dated Aug. 30, 2012.
U.S. Notice of Allowance for U.S. Appl. No. 14/498,334, dated Feb. 15, 2017.
U.S. Office Action for U.S. Appl. No. 13/606,746, dated Nov. 8, 2012.
U.S. Office Action for U.S. Appl. No. 14/498,334, dated Aug. 11, 2016.
Vanhessche et al., "L-Ribulose: A Novel Chiral Pool Compound," Tetrahedron Letters, vol. 31, No. 16, 1990, pp. 2337-2340.
Varela et al., "First Synthesis of Aldopentono-1,4-thiolactones," J. Org. Chem., vol. 58, No. 27, 1993 (abstract published in advance Nov. 15, 1993), pp. 7860-7864.
Wang et al., "Synthesis of 2'(S), 3'(R),5'-Trihydroxypentyladenine," Tetrahedron Letters, vol. 29, No. 10, 1988, pp. 1107-1110.
Watts et al., "Synthesis and Conformational Analysis of 2'-Fluoro-5-methyl-4'-thioarabinouridine (4'S-FMAU)," J. Org. Chem., vol. 71, No. 3, 2006 (published online Jan. 11, 2006), pp. 921-925.
Y. Yoshimura et al., Journal of Organic Chemistry, vol. 61, No. 3, 1996, pp. 822-823.
Y. Yoshimura et al., Nucleic Acids Symposium Series, No. 35, 1996, pp. 15-16.
Yoshimura et al., "A Novel Synthesis of 2'-Modified 2'-Deoxy-4'-thiocytidines from D-Glucose," J. Org.Chem., vol. 62, No. 10, 1997, pp. 3140-3152.
Yoshimura et al., "An Alternative Synthesis of Antineoplastic 4'-Thiocytidine Analogue 4'-ThioFAC," Tetrahedron Letters, vol. 40, 1999, pp. 1937-1940.
Yoshimura et al., "An Alternative Synthesis of Antineoplastic Nucleoside 4'-thioFAC," Nucleic Acids Symposium Series, No. 39, 1998, pp. 11-12.
Yoshimura et al., "Synthesis and Biological Activities of 2'-Deoxy-2'-fluoro-4'-thioarabinofuranosylpyrimidine and -Purine Nucleosides," Bioorganic & Medicinal Chemistry, vol. 8, 2000, pp. 1545-1558.
Zajchowski et al., "Anti-tumor Efficacy of the Nucleoside Analog 1-(2-deoxy-2-fluoro-4-thio-p-D-arabinofuranosyl) cytosine (4'-thio-FAC) in Human Pancreatic and Ovarian Tumor Xenograft Models," Int. J. Cancer, vol. 114, 2005 (published online Jan. 11, 2005), pp. 1002-1009.
Chinese Office Action, dated Jan. 16, 2017, for Chinese Application No. 201380042642.1, with an English translation.
Extended European Search Report, dated Mar. 16, 2017, for European Application No. 17150141.4.
Russian Office Action, dated Dec. 29, 2016, for corresponding Russian Application No. 2015108790, along with an English translation.

* cited by examiner

THIOPYRANOSE COMPOUND AND METHOD FOR PRODUCING SAME

CROSS-REFERENCE TO RELATED APPLICATIONS

This application is a Continuation of PCT International Application No. PCT/JP2015/052304 filed on Jan. 28, 2015, which claims priority under 35 U.S.C. §119 (a) to Japanese Patent Application No. JP2014-029978 filed in Japan on Feb. 19, 2014. Each of the above applications is hereby expressly incorporated by reference, in its entirety, into the present application.

BACKGROUND OF THE INVENTION

1. Field of the Invention

The present invention relates to a thiopyranose compound and a method for producing the same.

2. Description of the Related Art

Pyranose compound is a collective term for carbohydrates configuring a six-membered ring in which five carbon atoms and one oxygen atom form vertexes. Among these, glucopyranose having a glucose structure, mannopyranose having a mannose structure, and the like are included therein. There is an example in which a thiopyranose compound in which the oxygen atom included in the ring structure of the pyranose compound has been substituted with a sulfur atom is synthesized, and usefulness thereof as a resin material is known (refer to U.S. Pat. No. 3,243,425A). In recent years, a 5-thio-β-glucopyranoside compound has been expected as an effective component of a therapeutic medicine for diabetes, and development thereof has been progressing (refer to WO2004/014931A).

The synthetic methods of a thiopyranose compound are disclosed in U.S. Pat. No. 3,243,425A, WO2004/014931A, WO2004/106352A, and JP2010-059173A, and additionally, examples of the synthetic methods are exemplified in Journal of the Serbian Chemical Society, Volume: 55, Issue: 6, Pages: 359-61, Journal, 1990 (An improved synthesis of methyl 5-thio-D-arabino-pyranosides) and Carbohydrate Research Volume 282, Issue 2, 23 Feb. 1996, Pages 207-221.

SUMMARY OF THE INVENTION

However, the production methods described in the above-described patent documents and non-patent documents are not necessarily efficient, and there is room for improvement. Specifically, problems in which it is necessary to deal with an easily oxidized intermediate, the number of steps is large, the steps are complicated, and the like are exemplified. In addition, a pyranose compound has chirality, but in the above patent documents and non-patent documents, the synthesis control thereof is not particularly taken into consideration. Considering the use as medicine as described above, it is desired to stably obtain a desired product, if possible.

In view of the above problems, an object of the present invention is to provide a production method of a novel thiopyranose compound, which can synthesize a thiopyranose compound without passing through an unstable synthetic intermediate and without performing a complicated reaction operation, a product synthesized by the method, and an intermediate thereof.

In addition, if necessary, another object of the present invention is to provide a production method of a thiopyranose compound which can be obtained by controlling the steric conformation of a specific substituent of a product, the product, and an intermediate thereof.

According to the present invention, the following means is provided:

[1] A production method of a thiopyranose compound represented by the following Formula (2) by reacting a compound represented by the following Formula (1) with a sulfur compound.

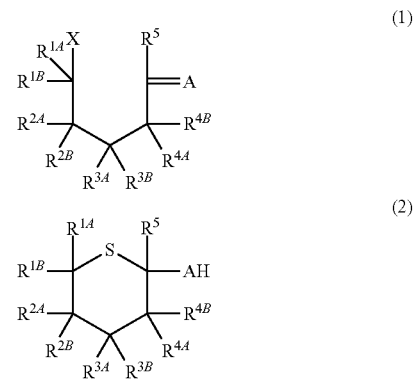

X represents a leaving group.

A represents an oxygen atom or a sulfur atom.

$R^{1A}$, $R^{1B}$, and $R^5$ are the same as or different from each other, and each of $R^{1A}$, $R^{1B}$, and $R^5$ represents a hydrogen atom, a hydroxyl group, a carboxyl group, a $C_{1-6}$ alkyl group, a $C_{2-6}$ alkenyl group, a $C_{2-6}$ alkynyl group, a $C_{6-20}$ aryl group, or a $C_{2-20}$ heterocyclic group.

$R^{2A}$ to $R^{4A}$ and $R^{2B}$ to $R^{4B}$ are the same as or different from each other, and each of $R^{2A}$ to $R^{4A}$ and $R^{2B}$ to $R^{4B}$ represents a hydrogen atom, a hydroxyl group, a halogen atom, a cyano group, an azido group, an amino group, a carboxyl group, $-OR^{OH}$, a $C_{1-6}$ alkyl group, a $C_{2-6}$ alkenyl group, a $C_{2-6}$ alkynyl group, a $C_{1-6}$ alkoxy group, a $C_{2-6}$ alkenyloxy group, a $C_{1-6}$ alkylthio group, a $C_{6-20}$ aryl group, a $C_{6-20}$ aryloxy group, a $C_{6-20}$ arylthio group, a $C_{1-20}$ acyloxy group, a $C_{1-20}$ acylimino group, a $C_{3-20}$ silyloxy group, a $C_{2-20}$ heterocyclic group, a $C_{2-20}$ heterocyclic oxy group, or a $C_{2-20}$ heterocyclic thio group.

Each pair of $R^{2A}$ and $R^{2B}$, $R^{3A}$ and $R^{3B}$, and $R^{4A}$ and $R^{4B}$ may be bonded to form a $C_{1-6}$ alkylidene group.

Two of $R^{1A}$ to $R^{4A}$ and $R^{1B}$ to $R^{4B}$ may be bonded to each other to form a group represented by $-O-Y^1-O-$.

Each of $R^{1A}$ to $R^{4A}$, $R^{1B}$ to $R^{4B}$, and $R^5$ may have a substituent or a protecting group.

$R^{OH}$ represents a hydroxyl protecting group.

$Y^1$ represents a $C_{1-6}$ alkylene group or a $C_{2-20}$ silylene group.

[2] The production method of a thiopyranose compound according to [1], in which $R^{1A}$ to $R^{4A}$, $R^{1B}$ to $R^{4B}$, $R^5$, and X in the above formulas are selected from the following list.

TABLE 1

| | |
|---|---|
| $R^{1A}$ | Hydrogen atom, |
| $R^{1B}$ | $C_{1-6}$ alkyl group, $C_{2-6}$ alkenyl group, $C_{6-20}$ aryl group, $C_{2-20}$ heterocyclic group, $C_{1-6}$ alkoxy $C_{1-6}$ alkyl group, $C_{6-20}$ aryloxy $C_{1-6}$ alkyl group, $C_{6-20}$ aryl $C_{1-6}$ alkyloxy $C_{1-6}$ alkyl group, $C_{2-6}$ alkanoyloxy $C_{1-6}$ alkyl group, $C_{7-20}$ aroyloxy $C_{1-6}$ alkyl group, $C_{3-20}$ silyloxy $C_{1-6}$ alkyl group |

TABLE 1-continued

| | |
|---|---|
| $R^{2A}$ | Hydrogen atom, hydroxyl group, |
| $R^{2B}$ | $C_{1-6}$ alkyl group, $C_{2-6}$ alkenyl group, $C_{6-20}$ aryl group, $C_{2-20}$ |
| $R^{3A}$ | heterocyclic group, $C_{1-6}$ alkoxy group, $C_{2-6}$ alkenyloxy group, $C_{6-20}$ |
| $R^{3B}$ | aryloxy group, $C_{6-20}$ aryl $C_{1-6}$ alkyloxy group, $C_{2-6}$ alkanoyloxy group, |
| $R^{4A}$ | $C_{7-20}$ aroyloxy group, $C_{3-20}$ silyloxy group, azido group, halogen atom, |
| $R^{4B}$ | $C_{1-20}$ acylimino group |
| $R^5$ | Hydrogen atom, $C_{1-6}$ alkyl group, $C_{2-6}$ alkenyl group, $C_{6-20}$ aryl group, $C_{1-6}$ alkoxy $C_{1-6}$ alkyl group, $C_{6-20}$ aryloxy $C_{1-6}$ alkyl group, $C_{6-20}$ aryl $C_{1-6}$ alkyloxy $C_{1-6}$ alkyl group, $C_{2-6}$ alkanoyloxy $C_{1-6}$ alkyl group, $C_{7-20}$ aroyloxy $C_{1-6}$ alkyl group |
| X | Halogen atom, $C_{1-6}$ alkylsulfonyloxy group, $C_{6-20}$ arylsulfonyloxy group |

Two adjacent alkoxy groups of $R^{1A}$ to $R^{4A}$ may be linked to form —O—$Y^1$—O—. Each of $R^{1A}$ to $R^{4A}$, $R^{1B}$ to $R^{4B}$, and $R^5$ may have a substituent selected from the substituent groups A and B.

Substituent group A: a halogen atom, a cyano group, a nitro group, an amino group, a hydroxyl group, a carboxyl group, a carbamoyl group, a sulfamoyl group, a $C_{1-6}$ alkyl group, a $C_{2-6}$ alkenyl group, a $C_{2-6}$ alkynyl group, a $C_{3-8}$ cycloalkyl group, a $C_{6-20}$ aryl group, a $C_{1-6}$ alkoxy group, a $C_{6-20}$ aryloxy group, a $C_{1-20}$ acyl group, a $C_{1-20}$ acyloxy group, a $C_{1-20}$ acylamino group, a $C_{1-6}$ alkoxycarbonyl group, a $C_{6-20}$ aryloxycarbonyl group, a $C_{1-6}$ alkoxycarbonyloxy group, a $C_{1-6}$ alkylamino group, a di($C_{1-6}$ alkyl) amino group, a $C_{1-6}$ alkylthio group, a $C_{1-6}$ alkylsulfonyl group, a $C_{6-20}$ arylsulfonyl group, a $C_{1-6}$ alkylsulfonyloxy group, a $C_{6-20}$ arylsulfonyloxy group, a $C_{1-18}$ silyl group, a $C_{2-20}$ heterocyclic group, and an oxo group.

The substituent group A may be substituted with the following substituent group B.

The hydroxyl group, the amino group, and the carboxyl group in the substituent group A may be protected.

Substituent group B: a halogen atom, a cyano group, a nitro group, an amino group, a hydroxyl group, a carboxyl group, a $C_{1-6}$ alkyl group, a $C_{6-20}$ aryl group, a $C_{1-6}$ alkoxy group, a $C_{2-20}$ heterocyclic group, and an oxo group.

The above-described substituents may be further substituted with a group in the substituent group B.

[3] The production method of a thiopyranose compound according to [1] or [2], in which A in the above formulas is an oxygen atom.

[4] The production method of a thiopyranose compound according to any one of [1] to [3], in which $R^5$ in the above formulas is a hydrogen atom.

[5] The production method of a thiopyranose compound according to any one of [1] to [4], in which each of $R^{2A}$ to $R^{4A}$ and $R^{2B}$ to $R^{4B}$ in the above formulas is independently a hydrogen atom or $OR^{OH}$.

[6] The production method of a thiopyranose compound according to any one of [1] to [5], in which $R^{1B}$, $R^{2B}$, $R^{3B}$, to $R^{4B}$ in the above formulas are hydrogen atoms.

[7] The production method of a thiopyranose compound according to any one of [1] to [6], in which the sulfur compound is sodium hydrogen sulfide.

[8] The production method of a thiopyranose compound according to any one of [1] to [7], in which $R^{2A}$, $R^{3A}$, and $R^{4A}$ in the above formulas are $OR^{OH}$'s.

[9] The production method of a thiopyranose compound according to any one of [1] to [8], in which $R^{1A}$ in the above formulas is a hydrogen atom, a methyl group, or $CH_2OR^{OH}$.

[10] The production method of a thiopyranose compound according to any one of [1] to [9], in which X in the above formula is a $C_{1-6}$ alkylsulfonyloxy group or a $C_{6-20}$ arylsulfonyloxy group.

[11] The production method of a thiopyranose compound according to any one of [1] to [9], in which X in the above formula is a halogen atom.

[12] The production method of a thiopyranose compound according to any one of [1] to [11], in which a reaction of the compound represented by Formula (1) with the sulfur compound is performed in an aprotic polar solvent.

[13] The production method of a thiopyranose compound according to any one of [1] to [11], in which the reaction of the compound represented by Formula (1) with the sulfur compound is performed in a protic polar solvent.

[14] The production method of a thiopyranose compound according to any one of [1] to [7] and [9] to [13], in which $R^{1A}$ in the above formulas is a hydrogen atom, a methyl group, or $CH_2OR^{OH}$, and $R^{2A}$ in the above formulas is a hydrogen atom.

[15] The production method of a thiopyranose compound according to any one of [1] to [14], in which the compound represented by Formula (2) is a compound represented by any one of the following Formulas (2-1) to (2-6).

(2-1)

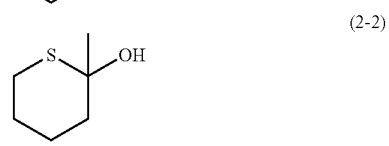

(2-2)

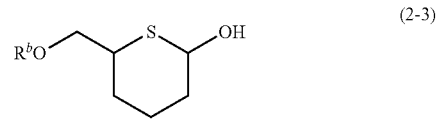

(2-3)

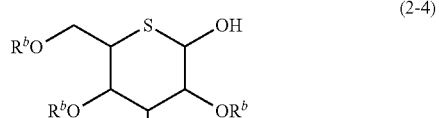

(2-4)

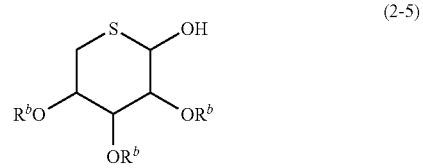

(2-5)

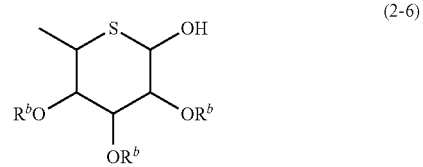

(2-6)

$R^b$ represents a $C_{2-6}$ alkanoyl group, a $C_{7-20}$ aroyl group, or a $C_{6-20}$ aryl $C_{1-6}$ alkyl group.

[16] The production method of a thiopyranose compound according to [15], in which $R^b$ in Formulas (2-4) to (2-6) is a $C_{2-6}$ alkanoyl group or a $C_{7-20}$ aroyl group.

[17] The production method of a thiopyranose compound according to [16], in which $R^b$ in Formulas (2-4) to (2-6) is an acetyl group or a benzoyl group.

[18] The production method of a thiopyranose compound according to any one of [1] to [17], in which the compound represented by Formula (2) is a compound represented by any one of the following Formulas (3-1) to (3-5).

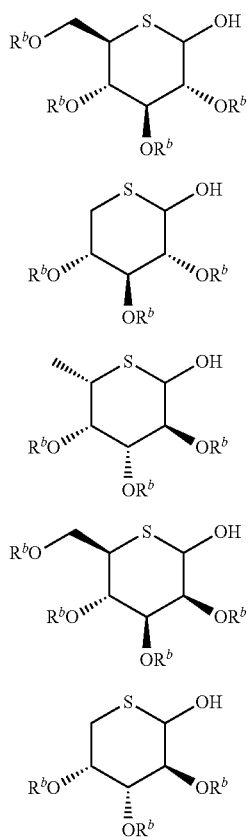

$R^b$ represents a benzoyl group.

[19] The production method of a thiopyranose compound according to any one of [1] to [18], in which the hydroxyl protecting group $R^{OH}$ is a $C_{7-20}$ aroyl group having a molecular weight of 106 or greater.

[20] The production method of a thiopyranose compound according to any one of [1] to [19], in which the compound represented by Formula (2) is synthesized through any synthesis route of the following (i) to (iii).

(i) By synthesizing the compound represented by Formula (1) from a compound represented by the following Formula (A) through a compound represented by the following Formula (C), a compound represented by Formula (E) is obtained as the compound represented by Formula (2)

(ii) By synthesizing the compound represented by Formula (1) from the compound represented by the following Formula (A) through a compound represented by the following Formula (C'), and through the compound represented by the following Formula (C), the compound represented by Formula (E) is obtained as the compound represented by Formula (2)

(iii) By synthesizing the compound represented by Formula (1) from the compound represented by the following Formula (A) through the compound represented by the following Formula (C'), the compound represented by Formula (E') is obtained as the compound represented by Formula (2)

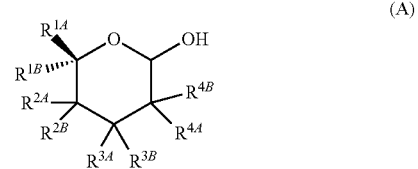

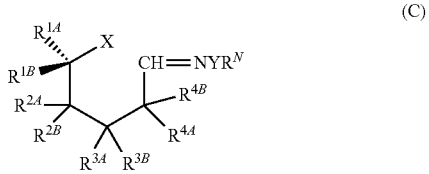

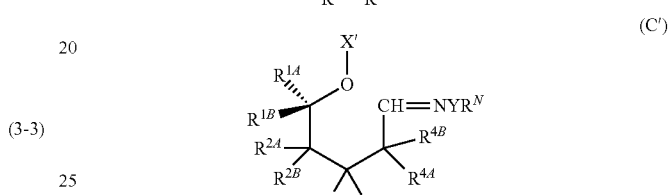

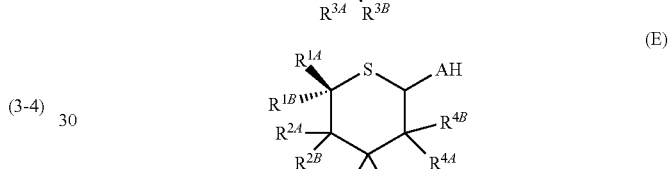

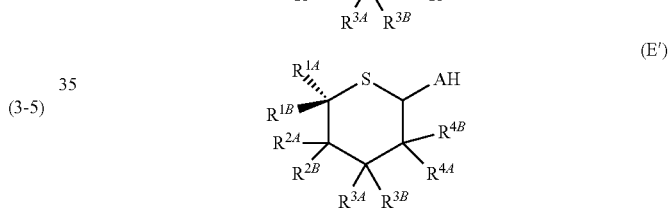

$R^{1A}$ to $R^{4A}$, $R^{1B}$ to $R^{4B}$, and A have the same meanings as those in Formula (1). Here, X is a halogen atom. X' is a $C_{1-6}$ alkylsulfonyl group or a $C_{6-20}$ arylsulfonyl group. Y represents an oxygen atom or $NR^N$. $R^N$'s are the same as or different from each other, and $R^N$ represents a hydrogen atom, a $C_{1-6}$ alkyl group, a $C_{6-20}$ aryl $C_{1-6}$ alkyl group, or a $C_{6-20}$ aryl group.

[21] A compound represented by the following Formula (1).

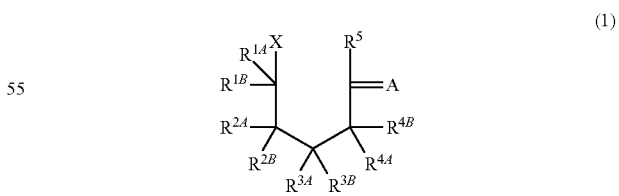

X represents a leaving group.
A represents an oxygen atom or a sulfur atom.
$R^{1A}$, $R^{1B}$, and $R^5$ are the same as or different from each other, and each of $R^{1A}$, $R^{1B}$, and $R^5$ represents a hydrogen atom, a hydroxyl group, a carboxyl group, a $C_{1-6}$ alkyl group, a $C_{2-6}$ alkenyl group, a $C_{2-6}$ alkynyl group, a $C_{6-20}$ aryl group, or a $C_{2-20}$ heterocyclic group.

$R^{2A}$ to $R^{4A}$ and $R^{2B}$ to $R^{4B}$ are the same as or different from each other, and each of $R^{2A}$ to $R^{4A}$ and $R^{2B}$ to $R^{4B}$ represents a hydrogen atom, a hydroxyl group, a halogen atom, a cyano group, an azido group, an amino group, a carboxyl group, —$OR^{OH}$, a $C_{1-6}$ alkyl group, a $C_{2-6}$ alkenyl group, a $C_{2-6}$ alkynyl group, a $C_{1-6}$ alkoxy group, a $C_{2-6}$ alkenyloxy group, a $C_{1-6}$ alkylthio group, a $C_{6-20}$ aryl group, a $C_{6-20}$ aryloxy group, a $C_{6-20}$ arylthio group, a $C_{1-20}$ acyloxy group, a $C_{1-20}$ acylimino group, a $C_{3-20}$ silyloxy group, a $C_{2-20}$ heterocyclic group, a $C_{2-20}$ heterocyclic oxy group, or a $C_{2-20}$ heterocyclic thio group.

Each pair of $R^{2A}$ and $R^{2B}$, $R^{3A}$ and $R^{3B}$, and $R^{4A}$ and $R^{4B}$ may be bonded to form a $C_{1-6}$ alkylidene group.

Two of $R^{1A}$ to $R^{4A}$ and $R^{1B}$ to $R^{4B}$ may be bonded to each other to form a group represented by —O—$Y^1$—O—.

Each of $R^{1A}$ to $R^{4A}$, $R^{1B}$ to $R^{4B}$, and $R^5$ may have a substituent or a protecting group.

$R^{OH}$ represents a hydroxyl protecting group.

$Y^1$ represents a $C_{1-6}$ alkylene group or a $C_{2-20}$ silylene group.

[22] The compound according to [21], in which at least one of $R^{1B}$ or $R^{1A}$, . . . , or $R^{4A}$ in the above formula is a $C_{6-20}$ aryl group-containing group.

[23] A compound represented by the following Formula (2).

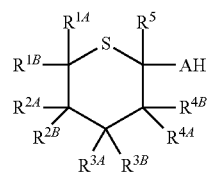

(2)

A represents an oxygen atom or a sulfur atom.

$R^{1A}$, $R^{1B}$, and $R^5$ are the same as or different from each other, and each of $R^{1A}$, $R^{1B}$, and $R^5$ represents a hydrogen atom, a hydroxyl group, a carboxyl group, a $C_{1-6}$ alkyl group, a $C_{2-6}$ alkenyl group, a $C_{2-6}$ alkynyl group, a $C_{6-20}$ aryl group, or a $C_{2-20}$ heterocyclic group.

$R^{2A}$ to $R^{4A}$ and $R^{2B}$ to $R^{4B}$ are the same as or different from each other, and each of $R^{2A}$ to $R^{4A}$ and $R^{2B}$ to $R^{4B}$ represents a hydrogen atom, a hydroxyl group, a halogen atom, a cyano group, an azido group, an amino group, a carboxyl group, —$OR^{OH}$, a $C_{1-6}$ alkyl group, a $C_{2-6}$ alkenyl group, a $C_{2-6}$ alkynyl group, a $C_{1-6}$ alkoxy group, a $C_{2-6}$ alkenyloxy group, a $C_{1-6}$ alkylthio group, a $C_{6-20}$ aryl group, a $C_{6-20}$ aryloxy group, a $C_{6-20}$ arylthio group, a $C_{1-20}$ acyloxy group, a $C_{1-20}$ acylimino group, a $C_{3-20}$ silyloxy group, a $C_{2-20}$ heterocyclic group, a $C_{2-20}$ heterocyclic oxy group, or a $C_{2-20}$ heterocyclic thio group.

Each pair of $R^{2A}$ and $R^{2B}$, $R^{3A}$ and $R^{3B}$, and $R^{4A}$ and $R^{4B}$ may be bonded to form a $C_{1-6}$ alkylidene group.

Two of $R^{1A}$ to $R^{4A}$ and $R^{1B}$ to $R^{4B}$ may be bonded to each other to form a group represented by —O—$Y^1$—O—.

Each of $R^{1A}$ to $R^{4A}$, $R^{1B}$ to $R^{4B}$, and $R^5$ may have a substituent or a protecting group.

$R^{OH}$ represents a hydroxyl protecting group.

$Y^1$ represents a $C_{1-6}$ alkylene group or a $C_{2-20}$ silylene group.

[24] The compound according to [23], in which at least one of $R^{1B}$ or $R^{1A}$, . . . , or $R^{4A}$ in the above formula is a $C_{6-20}$ aryl group-containing group.

[25] The compound according to any one of [21] to [24], which is a synthetic intermediate of an antidiabetic medicine.

[26] A compound represented by the following Formula (X-1) or (X-2), which, after a compound represented by Formula (2) is synthesized through the methods according to [1] to [20], is synthesized from the compound represented by Formula (2).

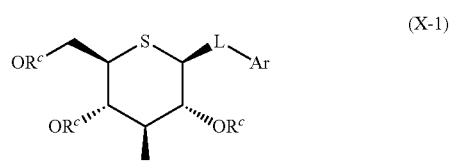

(X-1)

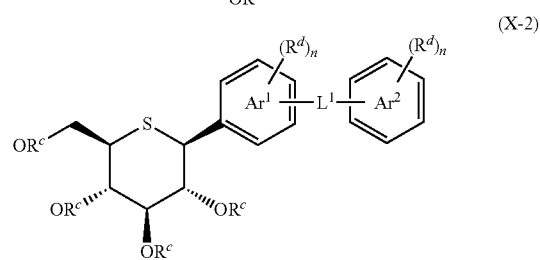

(X-2)

$R^c$ represents a hydrogen atom or a hydroxyl protecting group. L represents an oxygen atom or a sulfur atom. Ar is a $C_{6-20}$ aryl group.

$L^1$ represents a single bond or a linking group. $R^d$ is a substituent. n is an integer of 0 or greater.

Each of $Ar^1$ and $Ar^2$ is a $C_{6-20}$ aryl group.

[27] A production method of a thiopyranose compound, in which a compound represented by Formula (2) is synthesized through the methods according to [1] to [20], and a compound represented by the following Formula (X-1) or (X-2) is synthesized from the compound represented by Formula (2).

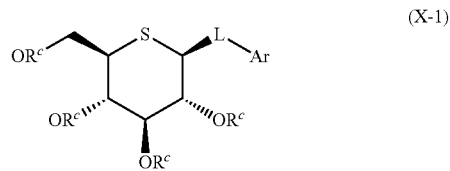

(X-1)

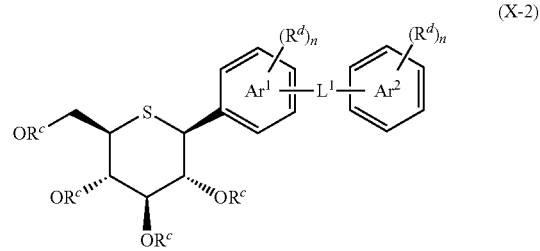

(X-2)

$R^c$ represents a hydrogen atom or a hydroxyl protecting group. L represents an oxygen atom or a sulfur atom. Ar is a $C_{6-20}$ aryl group.

$L^1$ represents a single bond or a linking group. $R^d$ is a substituent. n is an integer of 0 or greater.

Each of $Ar^1$ and $Ar^2$ is a $C_{6-20}$ aryl group.

The thiopyranose compound in the present invention means a carbohydrate of a six-membered ring in which five carbon atoms and one sulfur atom form vertexes, and specifically, represents the compound represented by Formula (2).

According to the present invention, it is possible to synthesize a thiopyranose compound without passing through an unstable synthetic intermediate and without performing a complicated reaction operation. In addition, if necessary, a thiopyranose compound can be obtained by controlling the steric conformation of a specific substituent of the product.

The above-described or other features and advantages of the present invention will become apparent from the following description.

DESCRIPTION OF THE PREFERRED EMBODIMENTS

In a production method of the present invention, a thiopyranose compound represented by the following Formula (2) is obtained by reacting a compound represented by the following Formula (1) with a sulfur compound.

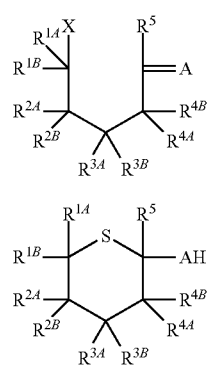

X represents a leaving group.

A represents an oxygen atom or a sulfur atom.

$R^{1A}$, $R^{1B}$, and $R^5$ are the same as or different from each other, and each of $R^{1A}$, $R^{1B}$, and $R^5$ represents a hydrogen atom, a hydroxyl group, a carboxyl group, a $C_{1-6}$ alkyl group, a $C_{2-6}$ alkenyl group, a $C_{2-6}$ alkynyl group, a $C_{6-20}$ aryl group, or a $C_{2-20}$ heterocyclic group.

$R^{2A}$ to $R^{4A}$ and $R^{2B}$ to $R^{4B}$ are the same as or different from each other, and each of $R^{2A}$ to $R^{4A}$ and $R^{2B}$ to $R^{4B}$ represents a hydrogen atom, a hydroxyl group, a halogen atom, a cyano group, an azido group, an amino group, a carboxyl group, —$OR^{OH}$, a $C_{1-6}$ alkyl group, a $C_{2-6}$ alkenyl group, a $C_{2-6}$ alkynyl group, a $C_{1-6}$ alkoxy group, a $C_{2-6}$ alkenyloxy group, a $C_{1-6}$ alkylthio group, a $C_{6-20}$ aryl group, a $C_{6-20}$ aryloxy group, a $C_{6-20}$ arylthio group, a $C_{1-20}$ acyloxy group, a $C_{1-20}$ acylimino group, a $C_{3-20}$ silyloxy group, a $C_{2-20}$ heterocyclic group, a $C_{2-20}$ heterocyclic oxy group, or a $C_{2-20}$ heterocyclic thio group.

Each pair of $R^{2A}$ and $R^{2B}$, $R^{3A}$ and $R^{3B}$, and $R^{4A}$ and $R^{4B}$ may be bonded to form a $C_{1-6}$ alkylidene group.

Two of $R^{1A}$ to $R^{4A}$ and $R^{1B}$ to $R^{4B}$ may be bonded to each other to form a group represented by —O—$Y^1$—O—.

Each of $R^{1A}$ to $R^{4A}$, $R^{1B}$ to $R^{4B}$, and $R^5$ may have a substituent or a protecting group.

$R^{OH}$ represents a hydroxyl protecting group.

$Y^1$ represents a $C_{1-6}$ alkylene group or a $C_{2-20}$ silylene group.

In the production method of the present invention, after a sulfur compound is added to the (C=A)$R^5$ group of the compound represented by Formula (1), a nucleophilic substitution reaction ($S_{N2}$ reaction) proceeds, and as a result, the ring is closed, and thus, it is thought that high reactivity and high selectivity of the reaction can be achieved. In addition, it is one of the new findings found in the present invention that even in the case of a pentose or hexose derivative which is a functional group such as a hydroxyl group, by effectively protecting the functional group, a high synthesis yield can be achieved. Moreover, the compound represented by Formula (1) may be a compound produced by a ring opening reaction of saccharide or the like, or may be a compound produced by other methods.

Each substituent in the above formula and a hydrogen atom are preferably selected from the following list.

TABLE 2

| | |
|---|---|
| $R^{1A}$ | Hydrogen atom, |
| $R^{1B}$ | $C_{1-6}$ alkyl group, $C_{2-6}$ alkenyl group, $C_{6-20}$ aryl group, $C_{2-20}$ heterocyclic group, $C_{1-6}$ alkoxy $C_{1-6}$ alkyl group, $C_{6-20}$ aryloxy $C_{1-6}$ alkyl group, $C_{6-20}$ aryl $C_{1-6}$ alkyloxy $C_{1-6}$ alkyl group, $C_{2-6}$ alkanoyloxy $C_{1-6}$ alkyl group, $C_{7-20}$ aroyloxy $C_{1-6}$ alkyl group, $C_{3-20}$ silyloxy $C_{1-6}$ alkyl group |
| $R^{2A}$ | Hydrogen atom, hydroxyl group, |
| $R^{2B}$ $R^{3A}$ $R^{3B}$ | $C_{1-6}$ alkyl group, $C_{2-6}$ alkenyl group, $C_{6-20}$ aryl group, $C_{2-20}$ heterocyclic group, $C_{1-6}$ alkoxy group, $C_{2-6}$ alkenyloxy group, $C_{6-20}$ aryloxy group, $C_{6-20}$ aryl $C_{1-6}$ alkyloxy group, $C_{2-6}$ alkanoyloxy group, |
| $R^{4A}$ | $C_{7-20}$ aroyloxy group, $C_{3-20}$ silyloxy group, azido group, halogen atom, |
| $R^{4B}$ | $C_{1-20}$ acylimino group |
| $R^5$ | Hydrogen atom, $C_{1-6}$ alkyl group, $C_{2-6}$ alkenyl group, $C_{6-20}$ aryl group, $C_{1-6}$ alkoxy $C_{1-6}$ alkyl group, $C_{6-20}$ aryloxy $C_{1-6}$ alkyl group, $C_{6-20}$ aryl $C_{1-6}$ alkyloxy $C_{1-6}$ alkyl group, $C_{2-6}$ alkanoyloxy $C_{1-6}$ alkyl group, $C_{7-20}$ aroyloxy $C_{1-6}$ alkyl group |
| X | Halogen atom, $C_{1-6}$ alkylsulfonyloxy group, $C_{6-20}$ arylsulfonyloxy group |

Two adjacent alkoxy groups of $R^{1A}$ to $R^{4A}$ may be linked to form —O—$Y^1$—O—. Each of $R^{1A}$ to $R^{4A}$, $R^{1B}$ to $R^{4B}$, and $R^5$ may have a substituent A or a substituent B described below.

Each substituent described above is more preferably selected from the following Table 2-1.

TABLE 2-1

| | |
|---|---|
| $R^{1A}$ | Hydrogen atom, |
| $R^{1B}$ | $C_{1-6}$ alkyl group, $C_{1-6}$ alkoxy $C_{1-6}$ alkyl group, $C_{6-20}$ aryl $C_{1-6}$ alkyloxy $C_{1-6}$ alkyl group, $C_{2-6}$ alkanoyloxy $C_{1-6}$ alkyl group, $C_{7-20}$ aroyloxy $C_{1-6}$ alkyl group, $C_{3-20}$ silyloxy $C_{1-6}$ alkyl group |
| $R^{2A}$ | Hydrogen atom, |
| $R^{2B}$ | $C_{1-6}$ alkyl group, $C_{1-6}$ alkoxy group, |
| $R^{3A}$ | $C_{6-20}$ aryl $C_{1-6}$ alkyloxy group, $C_{2-6}$ alkanoyloxy group, $C_{7-20}$ aroyloxy |
| $R^{3B}$ | group, $C_{3-20}$ silyloxy group, azido group, halogen atom, $C_{1-20}$ |
| $R^{4A}$ | acylimino group |
| $R^{4B}$ | |
| $R^5$ | Hydrogen atom, $C_{1-6}$ alkyl group, $C_{1-6}$ alkoxy $C_{1-6}$ alkyl group, $C_{2-6}$ alkanoyloxy $C_{1-6}$ alkyl group, $C_{7-20}$ aroyloxy $C_{1-6}$ alkyl group |
| X | Halogen atom, $C_{1-6}$ alkylsulfonyloxy group, $C_{6-20}$ arylsulfonyloxy group |

Each substituent described above is particularly preferably selected from the following Table 2-2.

TABLE 2-2

| | |
|---|---|
| $R^{1A}$ | $C_{1-6}$ alkyl group, $C_{1-6}$ alkoxy $C_{1-6}$ alkyl group, $C_{6-20}$ aryl $C_{1-6}$ alkyloxy $C_{1-6}$ alkyl group, $C_{2-6}$ alkanoyloxy $C_{1-6}$ alkyl group, $C_{7-20}$ aroyloxy $C_{1-6}$ alkyl group, $C_{3-20}$ silyloxy $C_{1-6}$ alkyl group |
| $R^{1B}$ | Hydrogen atom, $C_{1-6}$ alkyl group, $C_{1-6}$ alkoxy $C_{1-6}$ alkyl group, $C_{6-20}$ aryl $C_{1-6}$ alkyloxy $C_{1-6}$ alkyl group, $C_{2-6}$ alkanoyloxy $C_{1-6}$ alkyl group, $C_{7-20}$ aroyloxy $C_{1-6}$ alkyl group, $C_{3-20}$ silyloxy $C_{1-6}$ alkyl group |
| $R^{2A}$ | $C_{1-6}$ alkyl group, $C_{1-6}$ alkoxy group, |
| $R^{3A}$ | $C_{6-20}$ aryl $C_{1-6}$ alkyloxy group, $C_{2-6}$ alkanoyloxy group, $C_{7-20}$ aroyloxy |
| $R^{4A}$ | group, $C_{3-20}$ silyloxy group, azido group, halogen atom, $C_{1-20}$ acylimino group |
| $R^{2B}$ | Hydrogen atom, $C_{1-6}$ alkyl group, azido group, halogen atom, $C_{1-20}$ |
| $R^{3B}$ | acylimino group |
| $R^{4B}$ | |
| $R^5$ | Hydrogen atom |
| X | Halogen atom, $C_{1-6}$ alkylsulfonyloxy group, $C_{6-20}$ arylsulfonyloxy group |

Furthermore, in a case where each group is defined separately, the following is preferable.

A in the above formula is preferably an oxygen atom.

$R^5$ in the above formula is preferably a hydrogen atom.

Each of $R^{2A}$ to $R^{4A}$ and $R^{2B}$ to $R^{4B}$ is independently preferably a hydrogen atom or $OR^{OH}$.

Each of $R^{1B}$, $R^{2B}$, $R^{3B}$, and $R^{4B}$ is preferably a hydrogen atom.

Each of $R^{2A}$, $R^{3A}$, and $R^{4A}$ is preferably $OR^{OH}$.

$R^{1A}$ is preferably a hydrogen atom, a methyl group, or $CH_2OR^{OH}$.

X is preferably a $C_{1-6}$ alkylsulfonyloxy group or a $C_{6-20}$ arylsulfonyloxy group. These groups may be substituted with, for example, a halogen atom, a hydroxyl group, or one or more groups selected from the substituent group A.

For example, as the $C_{1-6}$ alkylsulfonyloxy group, a methanesulfonyloxy group, a trifluoromethanesulfonyloxy group, or a nonafluorobutanesulfonyloxy group is preferable, a methanesulfonyloxy group or trifluoromethanesulfonyloxy group is more preferable, and a methanesulfonyloxy group is particularly preferable.

As the $C_{6-20}$ arylsulfonyloxy group, a nitrobenzenesulfonyloxy group, a chlorobenzenesulfonyloxy group, a dichlorobenzenesulfonyloxy group, a trichlorobenzenesulfonyloxy group, or a pentafluorobenzenesulfonyloxy group is preferable, a 2-nitrobenzenesulfonyloxy group, a 3-nitrobenzenesulfonyloxy group, a 4-nitrobenzenesulfonyloxy group, a 4-chlorobenzenesulfonyloxy group, a 2-chlorobenzenesulfonyloxy group, a 2,4-dichlorobenzenesulfonyloxy group, a 3,5-dichlorobenzenesulfonyloxy group, a 2,4,6-trichlorobenzenesulfonyloxy group, a 2,4,5-trichlorobenzenesulfonyloxy group, or a pentafluorobenzenesulfonyloxy group is more preferable, and a 4-chlorobenzenesulfonyloxy group or 2,4,5-trichlorobenzenesulfonyloxy group is particularly preferable.

Alternatively, X is preferably a halogen atom. Among the halogen atom, a chlorine atom, a bromine atom, or an iodine atom is preferable. From the viewpoint of reactivity, a bromine atom or an iodine atom is preferable, and from the viewpoint of stability, a chlorine atom or a bromine atom is preferable.

$R^{1A}$ is preferably a hydrogen atom, a methyl group, or $CH_2OR^{OH}$, and $R^{2A}$ is preferably a hydrogen atom.

In the present invention, as $R^{OH}$, a protecting group having a $C_{6-20}$ aryl group is preferably used. For the relationship of Formulas (1) and (2), any one of $R^{1B}$ and $R^{1A}$ to $R^{4A}$ in the above formulas is preferably a $C_{6-20}$ aryl group-containing group. Thus, it is possible to promote crystallization of a compound, and the production suitability of a target compound is increased, and therefore, it is preferable that any one of $R^{1B}$ and $R^{1A}$ to $R^{4A}$ is a $C_{6-20}$ aryl group-containing group. Specific examples thereof include a $C_{6-20}$ aryl group, a $C_{6-20}$ aryloxy $C_{1-6}$ alkyl group, a $C_{7-20}$ aroyl group, a $C_{6-20}$ arylsulfonyl group, and a $C_{6-20}$ aryl $C_{1-20}$ silyl group, and, in particular, a $C_{7-20}$ aroyl group is preferable. The molecular weight of the $C_{7-20}$ aroyl group is preferably 106 or greater. Although the upper limit thereof is not particularly present, the molecular weight is practically 1,000 or less.

The $C_{6-20}$ aryl group included in $R^{OH}$ is preferably a $C_{6-20}$ aryl group in which two or more aromatic rings are linked or condensed, and specifically, a 1-naphthyl group, a 2-naphthyl group, a 9-anthracenyl group, and a 4-p-biphenyl group are exemplified.

Reaction Solvent

Examples of the solvent used in the above reaction include an aliphatic hydrocarbon compound, a halogenated hydrocarbon compound, an alcohol compound, an ether compound, an ester compound, a ketone compound, a nitrile compound, an amide compound, a sulfoxide compound, an aromatic hydrocarbon compound, a urea compound, and water, and these solvents may be used in combination. Respective specific examples will be shown in the section of abbreviations of substituents or the like described below. As preferable solvents, an alcohol compound, an ether compound, an ester compound, a nitrile compound, an amide compound, and a urea compound are exemplified, as more preferable solvents, an alcohol compound, a nitrile compound, an amide compound, and a urea compound are exemplified, and as particularly preferable solvents, an alcohol compound and an amide compound are exemplified.

Although the amount of solvent used is not particularly limited, the amount used is preferably 1-fold (v/w) or greater with respect to the compound represented by Formula (1). The upper limit thereof is preferably 50-fold (v/w) or less, and more preferably 15-fold (v/w) or less.

Sulfur Compound

Examples of the sulfur compound include hydrogen sulfide and a salt thereof. Examples of the salt of hydrogen sulfide include lithium sulfide, sodium sulfide, potassium sulfide, sodium hydrogen sulfide, potassium hydrogen sulfide, calcium hydrogen sulfide, and magnesium hydrogen sulfide, and sodium hydrogen sulfide or potassium hydrogen sulfide is preferable, and lithium hydrogen sulfide is more preferable. The amount of sulfur compound used is preferably 0.5-fold by mole or greater, more preferably 0.8-fold by mole or greater, and particularly preferably 1.0-fold by mole or greater, with respect to the compound represented by Formula (1). The upper limit thereof is preferably 5-fold by mole or less, more preferably 2-fold by mole or less, and particularly preferably 1.5-fold by mole or less. The form of the salt of hydrogen sulfide may be a solid or a solution, and the salt may be used in combination with a suitable solvent. In addition, the salt of hydrogen sulfide may be hydrate or anhydride.

Reaction Temperature

The reaction temperature is preferably −20° C. or higher, more preferably −10° C. or higher, and particularly preferably −5° C. or higher. The upper limit thereof is preferably 50° C. or lower, more preferably 30° C. or lower, and particularly preferably 10° C. or lower. The reaction time is preferably 5 minutes or longer. The upper limit thereof is preferably within 50 hours, more preferably within 3 hours, and particularly preferably within 1 hours.

Examples of the compounds represented by Formula (1) or (2) are shown below, but the present invention is not to be interpreted as being limited to this. Moreover, the table lists compounds corresponding to the following Formulas 1 to 4.

TABLE 3

Formula 1

$$\begin{array}{c} X \\ R^{1A} \\ R^{1B} \\ R^{2A} \\ R^{2B} \\ R^{3A} R^{3B} \end{array} \begin{array}{c} R^5 \\ =A \\ R^{4B} \\ R^{4A} \end{array}$$

Formula 2

$$\begin{array}{c} R^{1A} \\ R^{1B} \\ R^{2A} \\ R^{2B} \\ R^{3A} R^{3B} \end{array} \begin{array}{c} S \\ R^5 \\ -AH \\ R^{4B} \\ R^{4A} \end{array}$$

| Formula 1 | Formula 2 | R1A | R1B | R2A | R2B | R3A | R3B | R4A | R4B | R5 | A | X |
|---|---|---|---|---|---|---|---|---|---|---|---|---|
| 1-1 | 2-1 | H | H | H | H | H | H | H | H | H | O | Cl |
| 1-2 | 2-2 | H | H | H | H | H | H | H | H | H | O | Br |
| 1-3 | 2-3 | H | H | H | H | H | H | H | H | H | O | I |
| 1-4 | 2-4 | H | H | H | H | H | H | H | H | H | O | OMs |
| 1-5 | 2-5 | H | H | H | H | H | H | H | H | H | O | OTs |
| 1-6 | 2-6 | H | H | H | H | H | H | H | H | H | O | OCBS |
| 1-7 | 2-7 | H | H | H | H | H | H | H | H | H | O | OTCBS |
| 1-8 | 2-8 | H | H | H | H | H | H | H | H | H | O | OTf |
| 1-9 | 2-9 | H | H | H | H | H | H | H | H | H | O | ONf |
| 1-10 | 2-10 | H | H | H | H | H | H | H | H | H | S | Br |
| 1-11 | 2-11 | H | H | H | H | H | H | H | H | H | S | OMs |
| 1-12 | 2-12 | H | H | H | H | H | H | H | H | H | S | OTs |
| 1-13 | 2-13 | H | H | H | H | H | H | H | H | H | S | OTCBS |
| 1-14 | 2-14 | BzOCH$_2$ | H | H | H | H | H | H | H | H | O | OTCBS |
| 1-15 | 2-15 | Me | H | H | H | H | H | H | H | Ph | O | Br |
| 1-16 | 2-16 | Ph | H | H | H | H | H | H | H | Ph | O | Cl |
| 1-17 | 2-17 | H | H | H | H | H | H | H | H | Me | O | Cl |
| 1-18 | 2-18 | H | H | H | H | H | H | H | H | Ph | O | OMs |
| 1-19 | 2-19 | BzOCH$_2$ | H | BzO | H | BzO | H | BzO | H | H | O | Br |
| 1-20 | 2-20 | H | H | BzO | H | BzO | H | BzO | H | H | O | OMs |
| 1-21 | 2-21 | H | H | BzO | H | BzO | H | BzO | H | BzOCH$_2$ | O | OTs |
| 1-22 | 2-22 | Me | H | BzO | H | BzO | H | BzO | H | H | O | Cl |
| 1-23 | 2-23 | BzOCH$_2$ | H | BzO | H | BzO | H | BzO | H | H | O | Br |
| 1-24 | 2-24 | H | H | BzO | H | BzO | H | BzO | H | H | O | OMs |
| 1-25 | 2-25 | H | H | BzO | H | BzO | H | BzO | H | BzOCH$_2$ | O | OTs |
| 1-26 | 2-26 | Me | H | BzO | H | BzO | H | BzO | H | H | O | Cl |
| 1-27 | 2-27 | AcOCH$_2$ | H | AcO | H | AcO | H | AcO | H | H | O | Br |
| 1-28 | 2-28 | H | H | AcO | H | AcO | H | AcO | H | H | O | OMs |
| 1-29 | 2-29 | H | H | AcO | H | AcO | H | AcO | H | AcOCH$_2$ | O | OTs |
| 1-30 | 2-30 | Me | H | AcO | H | AcO | H | AcO | H | H | O | Cl |
| 1-31 | 2-31 | MeOCH$_2$ | H | MeO | H | MeO | H | MeO | H | H | O | Br |
| 1-32 | 2-32 | MeOBnOCH$_2$ | H | MeOBnO | H | MeOBnO | H | MeOBnO | H | H | O | Cl |
| 1-33 | 2-33 | Me$_2$COCH$_2$ | H | (R$^{1A}$)O | H | Me$_2$CO | H | (R$^{3A}$)O | H | H | O | Br |
| 1-34 | 2-34 | PivOCH$_2$ | H | PivO | H | PivO | H | PivO | H | H | O | Br |
| 1-35 | 2-35 | iPrCO$_2$CH$_2$ | H | iPrCO$_2$ | H | iPrCO$_2$ | H | iPrCO$_2$ | H | H | O | Br |
| 1-36 | 2-36 | BzOCH$_2$ | H | Me$_2$CO | H | (R$^{2A}$)O | H | MeOCH$_2$O | H | H | O | Br |
| 1-37 | 2-37 | BzOCH$_2$ | H | Me$_2$CO | H | (R$^{2A}$)O | H | BzO | H | H | O | Br |
| 1-38 | 2-38 | TrOCH$_2$ | H | MeOBnO | H | MeOBnO | H | MeOBnO | H | H | O | Br |
| 1-39 | 2-39 | MeOBnOCH$_2$ | H | AcO | H | MeOBnO | H | MeOBnO | H | H | O | Br |
| 1-40 | 2-40 | TBDPSOCH$_2$ | H | BzO | H | BzO | H | BzO | H | H | O | Br |
| 1-41 | 2-41 | AcOCH$_2$ | H | AcO | H | AcO | H | N3 | H | H | O | Br |
| 1-42 | 2-42 | BnOCH$_2$ | H | BnO | H | BnO | H | BnO | H | Ph | O | Cl |
| 1-43 | 2-43 | BzOCH$_2$ | H | BzO | H | F | H | BzO | H | H | O | Br |
| 1-44 | 2-44 | AcOCH$_2$ | H | AcO | H | F | H | AcO | H | H | O | Br |
| 1-45 | 2-45 | AcOCH$_2$ | H | AcO | H | AcO | H | AcNH | H | H | O | Br |
| 1-46 | 2-46 | H | H | BzO | H | Me$_2$CO | H | (R$^{3A}$)O | H | H | O | OMs |
| 1-47 | 2-47 | H | H | N3 | H | AcO | H | AcO | H | H | O | OTs |
| 1-48 | 2-48 | H | H | N3 | H | Me$_2$CO | H | (R$^{3A}$)O | H | H | O | OMs |
| 1-49 | 2-49 | H | H | BzO | H | F | H | BzO | H | H | O | OTs |
| 1-50 | 2-50 | H | H | BzO | H | Br | H | H | H | H | O | OMs |
| 1-51 | 2-51 | H | H | AcO | H | F | H | AcO | H | H | O | OTs |
| 1-52 | 2-52 | H | H | AcO | H | F | H | BzO | H | H | O | OMs |
| 1-53 | 2-53 | H | H | BzO | H | F | H | AcO | H | H | O | OTs |
| 1-55 | 2-55 | H | H | Me$_2$CO | H | (R$^{2A}$)O | H | AcO | H | BzOCH$_2$ | O | OTs |
| 1-56 | 2-56 | Me | H | AcO | H | AllylO | H | AcO | H | H | O | Br |

The compound represented by Formula (1) or (2) can be represented as a compound represented by the following Formula (3) or (4).

TABLE 4-1

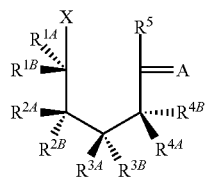

Formula 3

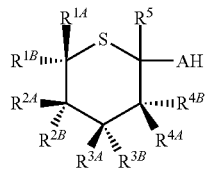

Formula 4

| Formula 3 | Formula 4 | R1A | R1B | R2A | R2B | R3A | R3B | R4A | R4B | R5 | A | X |
|---|---|---|---|---|---|---|---|---|---|---|---|---|
| 3-1 | 4-1 | H | H | H | BzO | H | BzO | H | BzO | H | O | OMs |
| 3-2 | 4-2 | H | H | BzO | H | BzO | H | BzO | H | H | O | OMs |
| 3-3 | 4-3 | H | H | H | BzO | H | BzO | BzO | H | H | O | OMs |
| 3-4 | 4-4 | H | H | BzO | H | BzO | H | H | BzO | H | O | OMs |
| 3-5 | 4-5 | H | H | H | BzO | BzO | H | H | BzO | H | O | OMs |
| 3-6 | 4-6 | H | H | BzO | H | H | BzO | BzO | H | H | O | OMs |
| 3-7 | 4-7 | H | H | H | BzO | BzO | H | BzO | H | H | O | OMs |
| 3-8 | 4-8 | H | H | BzO | H | H | BzO | H | BzO | H | O | OMs |
| 3-9 | 4-9 | BzOCH$_2$ | H | H | BzO | H | BzO | H | BzO | H | O | Br |
| 3-10 | 4-10 | H | BzOCH$_2$ | BzO | H | BzO | H | BzO | H | H | O | OMs |
| 3-11 | 4-11 | BzOCH$_2$ | H | H | BzO | H | BzO | BzO | H | H | O | Br |
| 3-12 | 4-12 | H | BzOCH$_2$ | BzO | H | BzO | H | H | BzO | H | O | OMs |
| 3-13 | 4-13 | BzOCH$_2$ | H | H | BzO | BzO | H | H | BzO | H | O | Br |
| 3-14 | 4-14 | H | BzOCH$_2$ | BzO | H | H | BzO | BzO | H | H | O | OMs |
| 3-15 | 4-15 | BzOCH$_2$ | H | H | BzO | BzO | H | BzO | H | H | O | Br |
| 3-16 | 4-16 | H | BzOCH$_2$ | BzO | H | H | BzO | H | BzO | H | O | OMs |
| 3-17 | 4-17 | BzOCH$_2$ | H | BzO | H | H | BzO | H | BzO | H | O | Br |
| 3-18 | 4-18 | H | BzOCH$_2$ | H | BzO | BzO | H | BzO | H | H | O | OMs |
| 3-19 | 4-19 | BzOCH$_2$ | H | BzO | H | H | BzO | BzO | H | H | O | Br |
| 3-20 | 4-20 | H | BzOCH$_2$ | H | BzO | BzO | H | H | BzO | H | O | OMs |
| 3-21 | 4-21 | BzOCH$_2$ | H | BzO | H | BzO | H | H | BzO | H | O | Br |
| 3-22 | 4-22 | H | BzOCH$_2$ | H | BzO | H | BzO | BzO | H | H | O | OMs |
| 3-23 | 4-23 | BzOCH$_2$ | H | BzO | H | BzO | H | BzO | H | H | O | Br |
| 3-24 | 4-24 | H | BzOCH$_2$ | H | BzO | H | BzO | H | BzO | H | O | OMs |
| 3-25 | 4-25 | H | H | H | BzO | H | BzO | BzO | H | BzOCH$_2$ | O | OMs |
| 3-26 | 4-26 | H | H | BzO | H | BzO | H | H | BzO | BzOCH$_2$ | O | OMs |
| 3-27 | 4-27 | H | Me | H | BzO | BzO | H | H | BzO | H | O | Br |
| 3-28 | 4-28 | Me | H | BzO | H | H | BzO | BzO | H | H | O | Br |
| 3-29 | 4-29 | H | H | H | AcO | H | AcO | H | AcO | H | O | OMs |
| 3-30 | 4-30 | H | H | H | AcO | AcO | H | H | AcO | H | O | OMs |
| 3-31 | 4-31 | AcOCH$_2$ | H | H | AcO | AcO | H | H | AcO | H | O | Br |
| 3-32 | 4-32 | AcOCH$_2$ | H | H | AcO | AcO | H | AcO | H | H | O | Br |
| 3-33 | 4-33 | H | H | H | AcO | AcO | AcO | H | H | AcOCH$_2$ | O | OMs |
| 3-34 | 4-34 | H | Me | H | AcO | AcO | H | H | AcO | H | O | Br |
| 3-35 | 4-35 | H | H | H | TolO | H | TolO | H | TolO | H | O | OMs |
| 3-36 | 4-36 | H | H | H | TolO | TolO | H | H | TolO | H | O | OMs |
| 3-37 | 4-37 | TolOCH$_2$ | H | H | TolO | TolO | H | H | TolO | H | O | Br |
| 3-38 | 4-38 | TolOCH$_2$ | H | H | TolO | TolO | H | TolO | H | H | O | Br |
| 3-39 | 4-39 | H | H | H | TolO | H | TolO | TolO | H | TolOCH$_2$ | O | OMs |
| 3-40 | 4-40 | H | Me | H | TolO | TolO | H | H | TolO | H | O | Br |
| 3-41 | 4-41 | H | H | H | PhBzO | H | PhBzO | H | PhBzO | H | O | OMs |
| 3-42 | 4-42 | H | H | H | PhBzO | PhBzO | H | H | PhBzO | H | O | OMs |
| 3-43 | 4-43 | PhBzOCH$_2$ | H | H | PhBzO | PhBzO | H | H | PhBzO | H | O | Br |
| 3-44 | 4-44 | PhBzOCH$_2$ | H | H | PhBzO | PhBzO | H | PhBzO | H | H | O | Br |
| 3-45 | 4-45 | H | H | H | PhBzO | H | PhBzO | PhBzO | H | PhBzOCH$_2$ | O | OMs |
| 3-46 | 4-46 | H | Me | H | PhBzO | PhBzO | H | H | PhBzO | H | O | Br |

TABLE 4-2

Formula 3

Formula 4

| Formula 3 | Formula 4 | R1A | R1B | R2A | R2B | R3A | R3B | R4A | R4B | R5 | A | X |
|---|---|---|---|---|---|---|---|---|---|---|---|---|
| 3-47 | 4-47 | H | H | H | BnO | H | BnO | H | BnO | H | O | OMs |
| 3-48 | 4-48 | H | H | BnO | H | BnO | H | BnO | H | H | O | OMs |
| 3-49 | 4-49 | H | H | H | BnO | BnO | H | H | BnO | H | O | OMs |
| 3-50 | 4-50 | H | H | BnO | H | H | BnO | BnO | H | H | O | OMs |
| 3-51 | 4-51 | BzOCH$_2$ | H | H | BnO | BnO | H | H | BnO | H | O | Cl |
| 3-52 | 4-52 | H | BzOCH$_2$ | BnO | H | H | BnO | BnO | H | H | O | Cl |
| 3-53 | 4-53 | BzOCH$_2$ | H | H | BnO | BnO | H | BnO | H | H | O | Cl |
| 3-54 | 4-54 | H | BzOCH$_2$ | BnO | H | H | BnO | H | BnO | H | O | Cl |
| 3-55 | 4-55 | H | H | H | BnO | H | BnO | BnO | H | BnOCH$_2$ | O | OMs |
| 3-56 | 4-56 | H | H | BnO | H | BnO | H | H | BnO | BnOCH$_2$ | O | OMs |
| 3-57 | 4-57 | H | Me | H | BnO | BnO | H | H | BnO | H | O | Br |
| 3-58 | 4-58 | Me | H | BnO | H | H | BnO | BnO | H | H | O | Br |
| 3-59 | 4-59 | H | H | H | ClBnO | H | ClBnO | H | ClBnO | H | O | OMs |
| 3-60 | 4-60 | H | H | H | ClBnO | ClBnO | H | H | ClBnO | H | O | OMs |
| 3-61 | 4-61 | ClBzOCH$_2$ | H | H | ClBnO | ClBnO | H | H | ClBnO | H | O | Cl |
| 3-62 | 4-62 | ClBzOCH$_2$ | H | H | ClBnO | ClBnO | H | ClBnO | H | H | O | Cl |
| 3-63 | 4-63 | H | BzOCH$_2$ | H | BzO | H | BzO | H | BzO | H | O | OMs |
| 3-64 | 4-64 | BzOCH$_2$ | H | BzO | H | BzO | H | BzO | H | H | O | OMs |
| 3-65 | 4-65 | H | BzOCH$_2$ | H | BzO | H | BzO | BzO | H | H | O | OMs |
| 3-66 | 4-66 | BzOCH$_2$ | H | BzO | H | H | BzO | H | BzO | H | O | OMs |
| 3-67 | 4-67 | H | BzOCH$_2$ | BzO | H | BzO | H | H | BzO | H | O | OMs |
| 3-68 | 4-68 | BzOCH$_2$ | H | BzO | H | H | BzO | BzO | H | H | O | OMs |
| 3-69 | 4-69 | H | BzOCH$_2$ | H | BzO | BzO | H | BzO | H | H | O | OMs |
| 3-70 | 4-70 | BzOCH$_2$ | H | BzO | H | H | BzO | H | BzO | H | O | OMs |
| 3-71 | 4-71 | H | BzOCH$_2$ | BzO | H | H | BzO | BzO | H | H | O | OMs |
| 3-72 | 4-72 | BzOCH$_2$ | H | H | BzO | BzO | H | BzO | H | H | O | OMs |
| 3-73 | 4-73 | H | BzOCH$_2$ | BzO | H | H | BzO | H | BzO | H | O | OMs |
| 3-74 | 4-74 | BzOCH$_2$ | H | H | BzO | H | BzO | BzO | H | H | O | OMs |
| 3-75 | 4-75 | H | BzOCH$_2$ | BzO | H | BzO | H | H | BzO | H | O | OMs |
| 3-76 | 4-76 | BzOCH$_2$ | H | H | BzO | H | BzO | H | BzO | H | O | OMs |
| 3-77 | 4-77 | H | BzOCH$_2$ | BzO | H | BzO | H | BzO | H | H | O | OMs |
| 3-78 | 4-78 | BzOCH$_2$ | H | H | BzO | H | BzO | H | BzO | H | O | OMs |
| 3-79 | 4-79 | Me | H | H | BzO | BzO | H | H | BzO | H | O | OMs |
| 3-80 | 4-80 | H | Me | BzO | H | H | BzO | BzO | H | H | O | OMs |

Abbreviations of respective substituents mean the following.

Ac: acetyl
Bn: benzyl
Bz: benzoyl
Et: ethyl
Me: methyl
Ms: methylsulfonyl or mesyl
Ph: phenyl
$^i$Pr: isopropyl
TBDPS: tert-butyl(diphenyl)silyl
TIPS: tris(propan-2-yl)silyl
Tol: (4-methylphenyl)carbonyl or toluoyl
RT (min): retention time (min)
Ts: (4-methylphenyl)sulfonyl or tosyl
Piv: pivaloyl
Tr: trityl Ph$_3$C
Nf: nonafluorobutanesulfonyl
CBS: 4-chlorobenzenesulfonyl
TCBS: 2,4,5-trichlorobenzenesulfonyl
Tf: trifluoromethanesulfonyl
N3: azide
ClBn: 4-chlorobenzyl Compounds 1-33, 2-33, 1-36, 2-36, 1-37, 2-37, 1-46, 2-46, 1-48, 2-48, 1-55, and 2-55 mean compounds having an acetonide protecting group. Each of the chemical structures thereof is as follows.

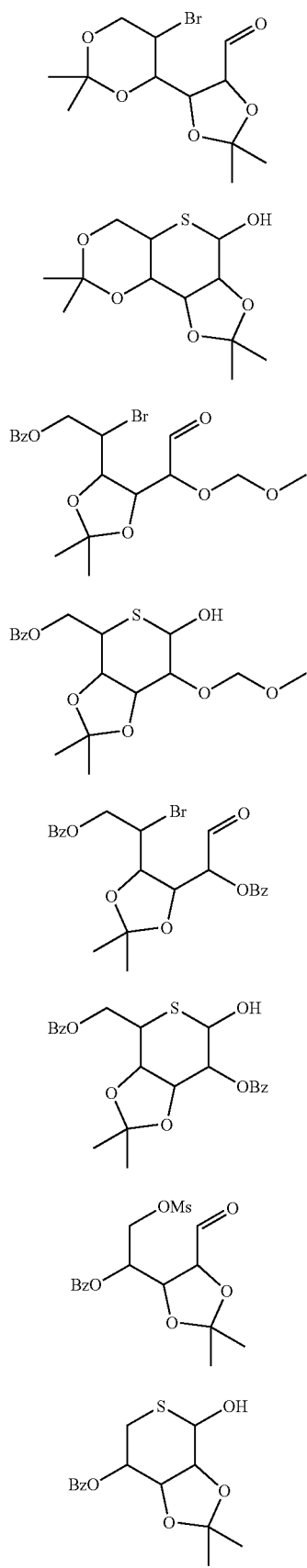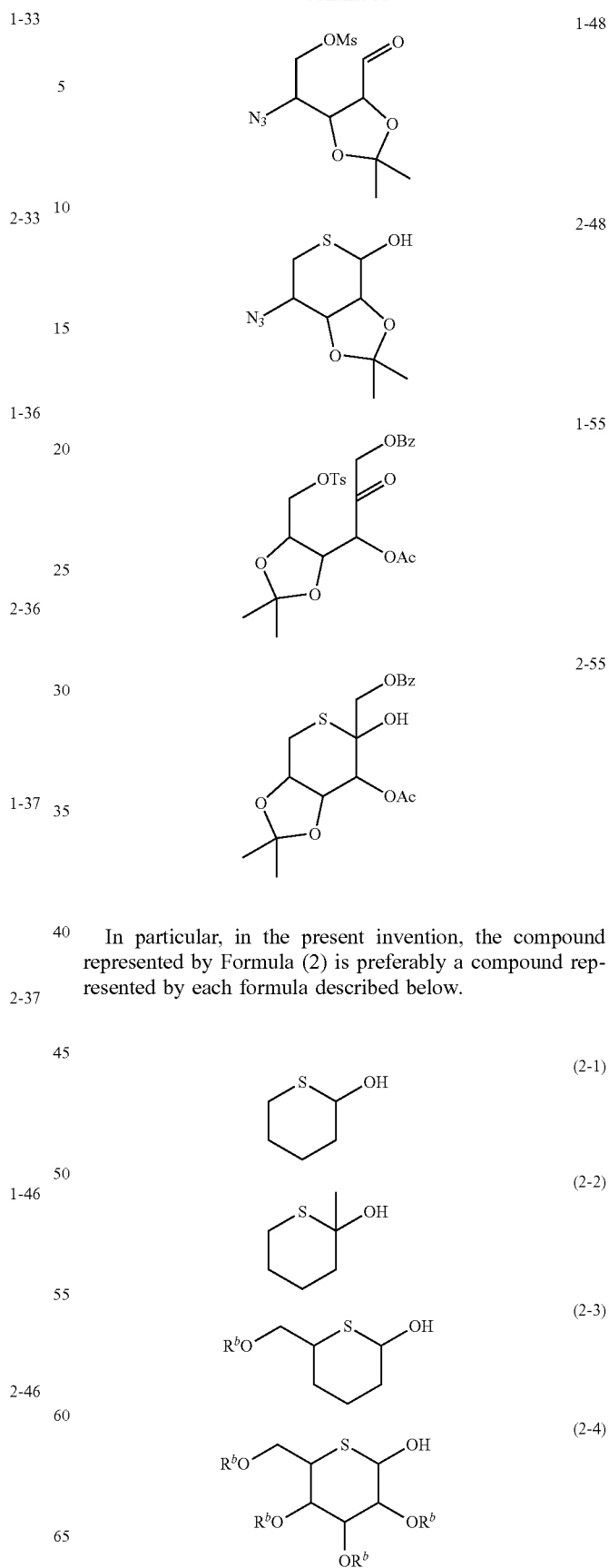
In particular, in the present invention, the compound represented by Formula (2) is preferably a compound represented by each formula described below.
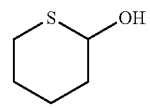 (2-1)
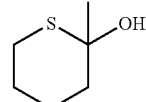 (2-2)
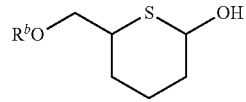 (2-3)
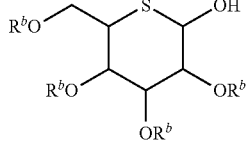 (2-4)

-continued

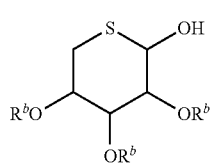
(2-5)

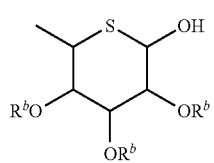
(2-6)

$R^b$ represents a $C_{2-6}$ alkanoyl group, a $C_{7-20}$ aroyl group, or a $C_{6-20}$ aryl $C_{1-6}$ alkyl group.

Furthermore, in the present invention, compounds represented by the following formulas are more preferable.

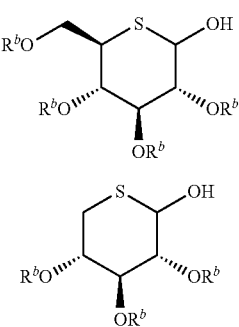

(3-1)

(3-2)

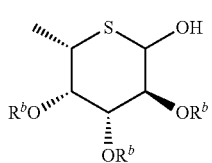
(3-3)

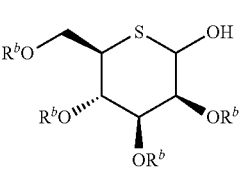
(3-4)

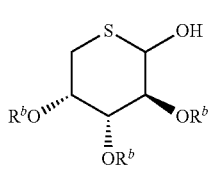
(3-5)

$R^b$ represents a benzoyl group.

Moreover, the OH group at the 1-position corresponds to the anomeric position of pyranose may be a conformation which is positioned on the front side, may be a conformation which is positioned on the back side, with respect to the thiopyranose skeleton, or may be a mixture including these two at an arbitrary ratio.

As the preferable embodiment of the production method of the present invention, the example of a process of deriving a thiopyranose compound from a pyranose compound is described below. Here, the present invention is not to be interpreted as being limited to the example.

Scheme A

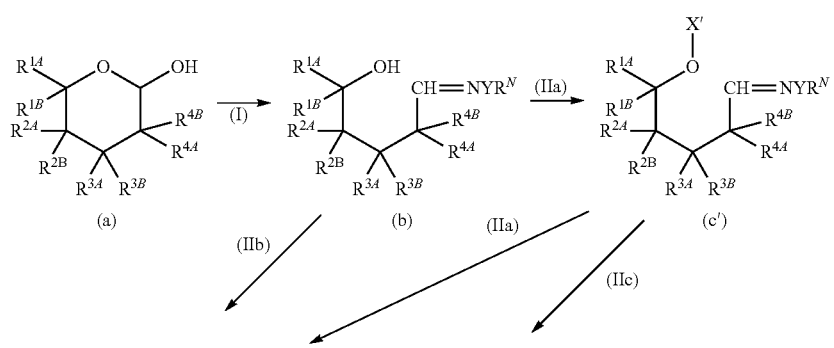

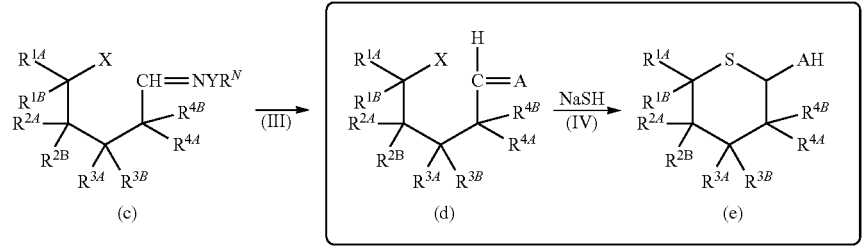

Moreover, each substituent in the above scheme A has the same meaning as that in Formula (1) or (2). $R^N$ is a hydrogen atom, a $C_{1-6}$ alkyl group, or a $C_{6-20}$ aryl group. X' is a group having the same meaning as X, but is different from X. In the examples, X is a halogen atom, and X' is $R^S SO_2$. $R^S$ is a $C_{1-6}$ alkyl group or a $C_{6-20}$ aryl group which may be substituted with one or more groups selected from the substituent group A. Y represents an oxygen atom or $NR^N$. $R^N$'s are the same as or different from each other, and $R^N$ represents a hydrogen atom, a $C_{1-6}$ alkyl group, a $C_{6-20}$ aryl $C_{1-6}$ alkyl group, or a $C_{6-20}$ aryl group.

Step (I)

As the compound represented by (a), for example, a commonly used pyranose compound can be used. Examples of the reactant used to obtain the compound (b) include a hydroxylamine compound. As the hydroxylamine compound, $H_2NOR^A$ or a salt thereof is preferable. $R^A$ is preferably a $C_{1-6}$ alkyl group, a $C_{6-20}$ aryl $C_{1-6}$ alkyl group, or a $C_{6-20}$ aryl group. Specifically, for example, O-methylhydroxylamine, O-tritylhydroxylamine, or O-benzylhydroxylamine can be used. Examples of a salt of $H_2NOR^A$ include hydrochloride. The ring at the position of the oxygen atom in the ring of the compound (a) is opened through this reaction, and an oxime compound (b, Y=O) in which the hydroxyl group of the 1-position has been substituted is obtained. In the present invention, it is preferable that an aldehyde compound (d) is derived by using this oxime compound, and this is used as a raw material, from the viewpoint of being stable to the subsequent reaction conditions and being possible to obtain an aldehyde compound (c) under mild conditions.

Examples of the solvent used in this reaction include an aliphatic hydrocarbon compound, a halogenated hydrocarbon compound, an alcohol compound, an ether compound, an ester compound, a nitrile compound, an amide compound, a sulfoxide compound, an aromatic hydrocarbon compound, a heteroaromatic compound, and water. These solvents may be used in combination. Although the amount of solvent used is not particularly limited, the amount used may be 1-fold to 50-fold (v/w), and preferably 1-fold to 15-fold (v/w), with respect to the compound (a).

The amount of reaction substrate (hydroxylamine compound) used in this reaction is preferably 0.5-fold by mole or greater, more preferably 0.8-fold by mole or greater, and particularly preferably 1-fold by mole or greater, with respect to the compound (a). The upper limit thereof is preferably 10-fold by mole or less, more preferably 5-fold by mole or less, and particularly preferably 2-fold by mole or less. In a case where a salt of the hydroxylamine compound which is a reaction substrate is used, a base is preferably added. Examples of the base include an organic base and an inorganic base, and triethylamine or sodium hydrogen carbonate is preferable. The amount of base used is preferably 0.1-fold by mole or greater, more preferably 0.2-fold by mole or greater, and particularly preferably 0.5-fold by mole or greater, with respect to the hydroxylamine compound. The upper limit thereof is preferably 10-fold by mole or less, more preferably 2-fold by mole or less, and particularly preferably 1.5-fold by mole or less.

The reaction temperature is preferably −10° C. or higher, more preferably −5° C. or higher, and particularly preferably 0° C. or higher. The upper limit thereof is preferably 100° C. or lower, more preferably 80° C. or lower, and particularly preferably 60° C. or lower. The reaction time is preferably 5 minutes or longer. The upper limit thereof is preferably within 50 hours, more preferably within 24 hours, and particularly preferably within 6 hours.

Examples of the usable reaction substrate other than the hydroxylamine compound include a primary amine compound and a hydrazine compound, and these give an imine compound and a hydrazone compound, respectively.

Step (II)

In the step, the hydroxyl group of the 5-position of the compound (b) is converted to X (or OX'). In this reaction, the following $R^S SO_2 X^S$, halide of an alkali metal, a halogenating agent, and the like are used. This reaction may be performed in one step, or may be performed in plural steps. A step (IIa) of performing halogenation in two steps and a step (IIb) of performing in one step are shown below. A step (IIc) of introducing $R^S SO_2$ and deriving this as it is to an aldehyde compound (d) is shown.

In a compound in which substituents $R^{1A}$ and $R^{1B}$ of the carbon atom of the 5-position are different, the portion becomes a asymmetric carbon. For the compound, by passing through the steps IIa and IIb in the above synthesis scheme A, it is possible to obtain a thiopyranose compound having the same steric conformation as the pyranose compound which is a raw material on the 5-position carbon atom. On the other hand, by passing through the step IIc, it is possible to obtain a thiopyranose compound having a steric conformation different from that of the raw material. In this manner, by suitably using the synthesis route, it is possible to control and synthesize a desired isomer.

Step (IIa)

A compound (c') can be produced by reacting the compound (b) with a compound represented by $X'X^S$ (preferably, $R^S SO_2 X^S$) in the presence of a base. $X^S$ is a bromine atom, a chlorine atom, or a fluorine atom. Examples of the solvent used in this reaction include an aliphatic hydrocarbon compound, a halogenated hydrocarbon compound, an ether compound, an ester compound, a ketone compound, a nitrile compound, an amide compound, a sulfoxide compound, and an aromatic hydrocarbon compound, and these solvents may be used in combination. Although the amount of solvent used is not particularly limited, the amount used may be 1-fold to 50-fold (v/w), and preferably 1-fold to 15-fold (v/w), with respect to the compound (b).

X' is preferably a $C_{1-6}$ alkylsulfonyl group or a $C_{6-20}$ arylsulfonyl group. Furthermore, X' is more preferably a methylsulfonyl group, a trifluoromethanesulfonyl group, a 2-nitrobenzenesulfonyl group, a 3-nitrobenzenesulfonyl group, a 4-nitrobenzenesulfonyl group, a 2,4,5-trichlorobenzenesulfonyl group, or a pentafluorobenzenesulfonyl group, and still more preferably a methylsulfonyl group or a 2,4,5-trichlorobenzenesulfonyl group. These group may be substituted with, for example, a halogen atom, a hydroxyl group, or one or more groups selected from the substituent group A.

Examples of the base used in this reaction include an organic base and an inorganic base, and triethylamine, pyridine, or N-methylimidazole is preferable. The amount of base used may be 0.5-fold by mole to 10-fold by mole, preferably 0.8-fold by mole to 4.0-fold by mole, and more preferably 1.0-fold by mole to 3.0-fold by mole, with respect to the compound (b). The amount of compound represented by $R^S SO_2 X^1$ used in this reaction is preferably 0.5-fold by mole or greater, more preferably 0.8-fold by mole or greater, and particularly preferably 1-fold by mole or greater, with respect to the compound (b). The upper limit thereof is preferably 10-fold by mole or less, more preferably 4-fold by mole or less, and particularly preferably 2-fold by mole or less.

The reaction temperature is preferably −10° C. or higher, more preferably −5° C. or higher, and particularly preferably 0° C. or higher. The upper limit thereof is preferably 100° C. or lower, more preferably 80° C. or lower, and particularly preferably 60° C. or lower. The reaction time is preferably 5 minutes or longer. The upper limit thereof is preferably within 50 hours, more preferably within 24 hours, and particularly preferably within 6 hours.

The compound (c) in which X is halogen can be produced by reacting the compound (c') with halide of an alkali metal. Examples of the solvent used in this reaction include an aliphatic hydrocarbon compound, a halogenated hydrocarbon compound, an ether compound, an ester compound, a ketone compound, a nitrile compound, an amide compound, a sulfoxide compound, an aromatic hydrocarbon compound, and a urea compound. These solvents may be used in combination. Although the amount of solvent used is not particularly limited, the amount used may be 1-fold to 50-fold (v/w), and preferably 1-fold to 15-fold (v/w), with respect to the compound (c).

Examples of the halide of an alkali metal used in this reaction include lithium fluoride, sodium fluoride, potassium fluoride, lithium bromide, sodium bromide, potassium bromide, lithium chloride, sodium chloride, potassium chloride, lithium iodide, sodium iodide, and potassium iodide, and lithium bromide is preferable. The amount of halide of an alkali metal used is preferably 0.5-fold by mole or greater, more preferably 0.8-fold by mole or greater, and particularly preferably 1-fold by mole or greater, with respect to the compound (c). The upper limit thereof is preferably 20-fold by mole or less, more preferably 8-fold by mole or less, and particularly preferably 5-fold by mole or less.

The reaction temperature is preferably −10° C. or higher, more preferably 0° C. or higher, and particularly preferably 20° C. or higher. The upper limit thereof is preferably 150° C. or lower, more preferably 100° C. or lower, and particularly preferably 80° C. or lower. The reaction time is preferably 5 minutes or longer. The upper limit thereof is preferably within 50 hours, more preferably within 24 hours, and particularly preferably within 6 hours.

Step (IIb)

To obtain the compound (c) in which X is halogen from the compound (b), the compound (b) is reacted with a halogenating agent in the presence of a base. Examples of the solvent used in this reaction include an aliphatic hydrocarbon compound, a halogenated hydrocarbon compound, an ether compound, an ester compound, a ketone compound, a nitrile compound, an amide compound, a sulfoxide compound, an aromatic hydrocarbon compound, a urea compound, and water, and these solvents may be used in combination. Although the amount of solvent used is not particularly limited, the amount used may be 1-fold to 50-fold (v/w), and preferably 1-fold to 15-fold (v/w), with respect to the compound (b).

Examples of the halogenating agent include a chlorinating agent and a brominating agent. Examples of the chlorinating agent include phosphoryl chloride, phosphorus trichloride, phosphorus pentachloride, Vilsmeier reagents (N,N-dimethylformamide-phosphorus pentachloride, N,N-dimethylformamide-phosphorus oxychloride, and the like), Rydon reagents ($Ph_3PCl_2$ and triphenylphosphine-carbon tetrachloride), thionyl chloride, and sulfuryl chloride, and sulfuryl chloride is preferable. Examples of the brominating agent include phosphorus tribromide, N,N-dimethylformamide-phosphorus tribromide, triphenylphosphine-carbon tetrabromide, and triphenylphosphine dibromide. The amount of halogenating agent used is preferably 0.1-fold by mole or greater, more preferably 0.8-fold by mole or greater, and particularly preferably 1-fold by mole or greater, with respect to the compound (b). The upper limit thereof is preferably 10-fold by mole or less, more preferably 5-fold by mole or less, and particularly preferably 2-fold by mole or less.

Examples of the base used in this reaction include an organic base and an inorganic base, and triethylamine or pyridine is preferable. The amount of base used is preferably 0.5-fold by mole or greater, more preferably 0.8-fold by mole or greater, and particularly preferably 1-fold by mole or greater, with respect to the compound (b). The upper limit thereof is preferably 50-fold by mole or less, more preferably 20-fold by mole or less, and particularly preferably 10-fold by mole or less.

In this reaction, a salt is preferably added. Examples of the salt include lithium chloride, lithium bromide, sodium bromide, calcium bromide, and pyridine hydrochloride. In the halogenation reaction, typically, an epimer mixture is obtained. To improve the purity of the compound (c), sulfuryl chloride and lithium chloride are preferably used in combination. The amount of salt used is preferably 0.5-fold by mole or greater, more preferably 0.8-fold by mole or greater, and particularly preferably 1-fold by mole or greater, with respect to the compound (b). The upper limit thereof is preferably 20-fold by mole or less, more preferably 5-fold by mole or less, and particularly preferably 3-fold by mole or less.

The reaction temperature is preferably −50° C. or higher, more preferably −40° C. or higher, and particularly preferably −30° C. or higher. The upper limit thereof is preferably 80° C. or lower, more preferably 60° C. or lower, and particularly preferably 40° C. or lower. The reaction time is preferably 5 minutes or longer. The upper limit thereof is preferably within 50 hours, more preferably within 24 hours, and particularly preferably within 6 hours.

Step (IIc)

In a step IIc, the compound (d) is directly synthesized from the compound (c'). The reaction conditions and the procedure are the same as the following step (III). In the above scheme A, the functional group of the 5-position of the compound (d) is X, in the case of passing through the step IIc, the functional group is OX'. That is, in the next step, by reacting a compound having OX' at the 6-position with a sulfur compound described below, a compound (e) is obtained.

Step (III)

The compound (d) can be produced by hydrolyzing the compound (c) in the presence of an acid. Examples of the solvent used in this reaction include an aliphatic hydrocarbon compound, a halogenated hydrocarbon compound, an alcohol compound, an ether compound, an ester compound, a ketone compound, a nitrile compound, an amide compound, a sulfoxide compound, an aromatic hydrocarbon compound, a urea compound, and water. These solvents may be used in combination. Although the amount of solvent used is not particularly limited, the amount used may be 1-fold to 50-fold (v/w), and preferably 1-fold to 15-fold (v/w), with respect to the compound (c).

Examples of the acid used in the reaction include hydrochloric acid, sulfuric acid, toluenesulfonic acid, acetic acid, glyoxylic acid, and phosphoric acid, and glyoxylic acid is preferable. The amount of acid used is preferably 0.5-fold by mole or greater, more preferably 1-fold by mole or greater, and particularly preferably 1.5-fold by mole or greater, with respect to the compound (c). The upper limit thereof is preferably 100-fold by mole or less, more preferably 60-fold by mole or less, and particularly preferably 40-fold by mole or less.

In this reaction, a carbonyl compound is preferably added. Examples of the carbonyl compound include ketones such as acetone and 2-butanone and aldehydes such as formaldehyde, benzaldehyde, glyoxal, and glyoxylic acid, and aldehydes are preferable, and glyoxylic acid is more preferable. The amount of carbonyl compound used is preferably 0.5-fold by mole or greater, more preferably 1-fold by mole or greater, and particularly preferably 1.5-fold by mole or greater, with respect to the compound (c). The upper limit thereof is preferably 100-fold by mole or less, more preferably 60-fold by mole or less, and particularly preferably 40-fold by mole or less.

The reaction temperature is preferably −10° C. or higher, more preferably 0° C. or higher, and particularly preferably 20° C. or higher. The upper limit thereof is preferably 120° C. or lower, more preferably 100° C. or lower, and particularly preferably 80° C. or lower. The reaction time is preferably 5 minutes or longer. The upper limit thereof is preferably within 50 hours, more preferably within 24 hours, and particularly preferably within 6 hours.

Step (IV)

The compound (e) can be produced by reacting the compound (d) with a sulfur compound. This reaction may be performed according to the method described above. Additionally, the reaction from the substrate in which X in the compound (d) is chlorine can be referred to JP2006-335737A. Here, the substrate disclosed in the same publication is a derivative of toluene, and the relationship between the reactive substituent and the chirality thereof is not considered.

By using a different reaction route as described above, it is possible to synthesize the compound represented by Formula (2) in any one of the synthesis routes (i) to (iii) described below, and obtain a predetermined isomer.

(i) By synthesizing the compound represented by Formula (1) from a compound represented by the following Formula (A) through a compound represented by the following Formula (C), a compound represented by Formula (E) is obtained as the compound represented by Formula (2)

(ii) By synthesizing the compound represented by Formula (1) from the compound represented by the following Formula (A) through a compound represented by the following Formula (C'), and through the compound represented by the following Formula (C), the compound represented by Formula (E) is obtained as the compound represented by Formula (2)

(iii) By synthesizing the compound represented by Formula (1) from the compound represented by the following Formula (A) through the compound represented by the following Formula (C'), the compound represented by Formula (E') is obtained as the compound represented by Formula (2).

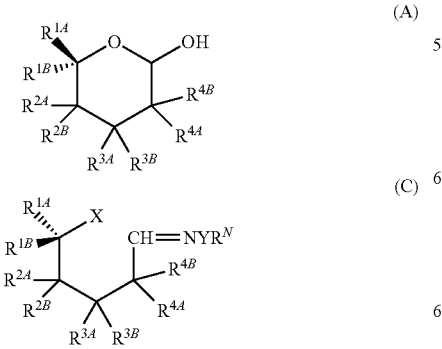

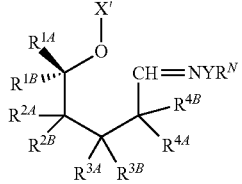

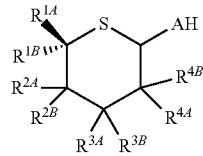

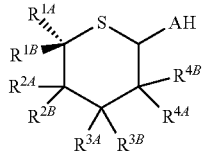

$R^{1A}$ to $R^{4A}$, $R^{1B}$ to $R^{4B}$, and A have the same meanings as those in Formula (1). Here, X is a halogen atom. X' is a $C_{1-6}$ alkylsulfonyl group or a $C_{6-20}$ arylsulfonyl group. Y represents an oxygen atom or a nitrogen atom. $R^N$ represents a hydrogen atom, a $C_{1-6}$ alkyl group, a $C_{6-20}$ aryl $C_{1-6}$ alkyl group, or a $C_{6-20}$ aryl group.

To substitute the hydrogen atom of AH in the compound (e) with an arbitrary substituent, a typical substrate can be used. For example, acetyl chloride, benzoyl chloride, benzenesulfonyl chloride, or methanesulfonyl chloride can be used. Alternatively, for example, acetic anhydride, propionic anhydride, or the like can be used.

Examples of the solvent used in this reaction include an aliphatic hydrocarbon compound, a halogenated hydrocarbon compound, an ether compound, an ester compound, a ketone compound, a nitrile compound, an amide compound, a sulfoxide compound, and an aromatic hydrocarbon compound. These solvents may be used in combination. Although the amount of solvent used is not particularly limited, the amount used may be 1-fold to 50-fold (v/w), and preferably 1-fold to 15-fold (v/w), with respect to the compound (e).

The amount of substitution compound used in this reaction is preferably 0.5-fold by mole or greater, more preferably 0.8-fold by mole or greater, and particularly preferably 1-fold by mole or greater, with respect to the compound (e). The upper limit thereof is preferably 50-fold by mole or less, more preferably 20-fold by mole or less, and particularly preferably 10-fold by mole or less.

In this reaction, a base is preferably added. Examples of the base include an organic base and an inorganic base, and triethylamine is preferable. The amount of base used is preferably 0.5-fold by mole or greater, more preferably 0.8-fold by mole or greater, and particularly preferably 1-fold by mole or greater, with respect to the compound (e). The upper limit thereof is preferably 50-fold by mole or less, more preferably 20-fold by mole or less, and particularly preferably 15-fold by mole or less.

The reaction temperature is preferably −10° C. or higher, more preferably −5° C. or higher, and particularly preferably 0° C. or higher. The upper limit thereof is preferably 100° C. or lower, more preferably 80° C. or lower, and particularly preferably 60° C. or lower. The reaction time is preferably 5 minutes or longer. The upper limit thereof is preferably within 50 hours, more preferably within 24 hours, and particularly preferably within 6 hours.

In addition to the above, the compound (the compound (d) in the scheme) represented by Formula (1) can be synthesized by a suitable ordinary method. For example, a linear alcohol compound having 4 or 5 carbon atoms, having a hydroxyl group (or a thiol group) at the 1-position is prepared. A substituent X is introduced at the terminal of the opposite side to the hydroxyl group. Alternatively, such a compound may be supplied. By oxidizing the portion of the hydroxyl group by an ordinary method, a (thio)aldehyde compound corresponding to Formula (1) can be obtained.

By another method, an unsaturated fatty acid having a vinyl group at the terminal is prepared. By cyclizing this by an ordinary method, a lactone having a hydroxymethyl group is obtained. The hydroxyl group (or a thiol group) is further substituted with a protecting group by an ordinary method. Next, by ring-opening the lactone ring, a diol is obtained. Thereafter, by modifying the hydroxyl group at one terminal with X and oxidizing the hydroxyl group at the other terminal, an aldehyde compound can be obtained.

The compound obtained by the production method described above can be isolated and purified by a typical method such as extraction, crystallization, distillation, or column chromatography. In addition, the compound obtained by the production method described above may be used in the next reaction as it is without isolation.

In the compound having a formyl group (or a thioformyl group) obtained by the production method described above, a hydrate or an alcohol adduct is present in some cases. The present invention includes all of these. In addition, in a case where tautomers or enantiomers are present, the present invention includes these isomers. Furthermore, in a case where a crystal polymorphism substance, a salt, a hydrate, or a solvate is present, the present invention includes all of the crystal form substance, the salt, the hydrate, and the solvate.

Applications

The thiopyranose compound obtained by the production method of the present invention can be applied to various applications. For example, the compound is useful as a raw material of the resin as described in U.S. Pat. No. 3,243,425A or an additive. In addition, according to the recent report, the compound is also useful as a substrate of a therapeutic medicine for diabetes as described in WO2004/014931A, WO2004/106352A, and JP2010-059173A.

More specific examples of use as an active ingredient of medicine include the compound represented by the following Formula X-1 disclosed in WO2004/014931A.

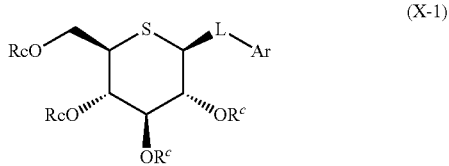

(X-1)

$R^c$ represents a hydrogen atom or a hydroxyl protecting group. L represents an oxygen atom or a sulfur atom. Ar is a $C_{6-20}$ aryl group.

This compound can be synthesized according to, for example, the method described in pp. 34-36 of WO2004/014931A.

In the method according to the above publication, a bisaryl compound which becomes aglycone can be synthesized, for example, by condensing a phenol compound and a benzyl alcohol compound under acidic conditions. A thiopyranose compound having a hydroxyl group at the 1-position is synthesized from pentaacetyl thioglucose. Next, by condensing the thiopyranose compound having a hydroxyl group at the 1-position and the bisaryl compound having a hydroxyl group under conditions of a Mitsunobu reaction using an azo reagent and phosphines, the compound represented by Formula (X-1) can be obtained.

Alternatively, a compound represented by the following Formula (X-2) is also preferably synthesized according to the procedure in paragraphs [0165] to [0176] of JP2010-059173A.

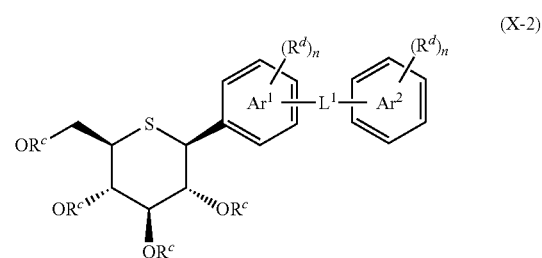

(X-2)

$R^c$ represents a hydrogen atom or a hydroxyl protecting group. $L^1$ represents a single bond or a linking group. $R^d$ is a substituent. n is an integer of 0 or greater.

Each of $Ar^1$ and $Ar^2$ is a $C_{6-20}$ aryl group.

Roughly speaking, for a substituent portion (aglycone) to be introduced to a thiopyranose compound, an example using a predetermined bisaryl compound (which includes a heteroaryl compound) is exemplified. In a case where the aryl compound which is a raw material has an alkoxy group, by performing halogenation in a first step, a Friedel-Crafts reaction, and reduction in the order, a halogenated bisaryl compound can be obtained.

On the other hand, in a case where, in Formula (2), A is an oxygen atom, $R^5$ is a hydrogen atom, and the hydroxy protecting group is an aralkyl group such as a benzyl group, by treating this compound with a suitable oxidant, a thiolactone compound is produced. When the hydroxyl group at the 1-position is protected with an acetyl group or the like, for example, by the method disclosed in JP2010-059173A, a desired compound can be obtained through a plurality of steps including 1-position selective deacetylation of pentaacetyl thioglucose. By reacting the thiolactone compound having a hydroxyl group at the 1-position described above with the halogenated bisaryl compound described above and a Grignard reagent prepared from magnesium, the compound represented by Formula X-2 can be obtained.

The compound represented by Formula (X-2) is more preferably a compound represented by the following Formula (X-2a).

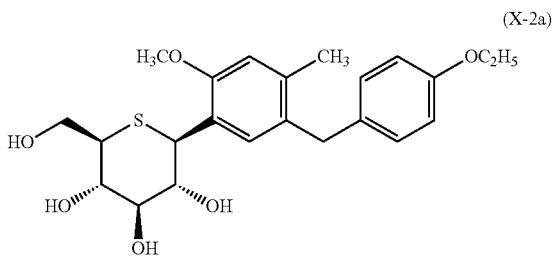 [SMILES: CCOc1ccc(Cc2cc([C@@H]3S[C@H](CO)[C@@H](O)[C@H](O)[C@H]3O)c(OC)cc2C)cc1]

(X-2a)

<Definition of Compounds and Substituents>

In the specification, the substituent of each compound may be have a group in a substituent group A described below unless specified otherwise. In addition, a hydroxyl group, an amino group, and a carboxyl group may be protected with protecting groups listed as abbreviations such as substituents described below. This is the same for all of the substituents and compounds listed as abbreviations of the substituents described below.

In the present specification, when a plurality of substituents or linking groups indicated by specific signs are present, or when a plurality of substituents or the like (definition of the number of substituents is also the same) are defined simultaneously or alternatively, respective substituents or the like may be the same as or different from each other. In addition, when a plurality of substituents or the like are adjacent, these may be bonded to each other or condensed to form a ring.

The alkyl group.the alkylene group, the alkenyl group.the alkenylene group, and the alkynyl group.the alkynylene group included in each substituent may be branched, linear, or cyclic. In addition, when a $C_{6-20}$ aryl group, a heterocyclic group, or the like is included, this may be a monocycle or a condensed ring.

In the present specification, respective technical matters such as a temperature and a thickness, including a choice of substituents or linking groups of the compound do not interfere the combination with each other, even in a case where each of the lists is independently described.

<Abbreviation of Substituents or the Like>

When written as $C_{X-Y}$, it is meant that the substituent thereof has X to Y carbon atoms.

A halogen atom is a fluorine atom, a chlorine atom, a bromine atom, or an iodine atom.

A $C_{1-6}$ alkyl group means a methyl group, an ethyl group, a propyl group, an isopropyl group, a butyl group, a sec-butyl group, an isobutyl group, a tert-butyl group, a pentyl group, a hexyl group, or the like.

A $C_{2-6}$ alkenyl group means a vinyl group, an allyl group, a propenyl group, an isopropenyl group, a butenyl group, an isobutenyl group, a 1,3-butadienyl group, a pentenyl group, a hexenyl group, or the like.

A $C_{2-6}$ alkynyl group means an ethynyl group, a propynyl group, a butynyl group, a pentynyl group, a hexynyl group, or the like.

A $C_{3-8}$ cycloalkyl group means a cyclopropyl group, a cyclobutyl group, a cyclopentyl group, a cyclohexyl group, or the like.

A $C_{6-20}$ aryl group means a phenyl group, a naphthyl group, or the like.

A $C_{6-20}$ aryl $C_{1-6}$ alkyl group means a benzyl group, a diphenylmethyl group, a trityl group, a phenethyl group, a naphthylmethyl group, or the like. In addition, an aryl $C_{1-6}$ alkyl group which may have a substituent means a methylbenzyl group, a chlorobenzyl group, a methoxybenzyl group, or the like.

A $C_{1-3}$ alkylene group means a methylene group, an ethylene group, a propylene group, or the like.

A $C_{1-6}$ alkylidene group means a methylidene group, an ethylidene group, a propylidene group, a butylidene group, a pentylidene group, a hexylidene group, or the like.

A $C_{1-6}$ alkoxy group means a methoxy group, an ethoxy group, a propoxy group, an isopropoxy group, a butoxy group, an isobutoxy group, a sec-butoxy group, a tert-butoxy group, a pentyloxy group, a hexyloxy group, or the like.

A $C_{6-20}$ aryloxy group means a phenoxy group, a naphthyloxy group, or the like.

A $C_{1-6}$ alkoxy $C_{1-6}$ alkyl group means a methoxymethyl group, a 1-ethoxyethyl group, or the like.

A $C_{2-6}$ alkanoyl group means an acetyl group, a propionyl group, a valeryl group, an isovaleryl group, a pivaloyl group, or the like.

A $C_{7-20}$ aroyl group means a benzoyl group, a p-toluoyl group, a 4-phenylbenzoyl group, a naphthoyl group, or the like.

A $C_{2-20}$ heterocyclic carbonyl group means a nicotinoyl group, a thenoyl group, a pyrrolidinocarbonyl group, a furoyl group, or the like.

An (α-substituted) aminoacetyl group means an (α-substituted) aminoacetyl group in which the N-terminal, which is derived from an amino acid (glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline, hydroxyproline, or the like), may be protected.

A $C_{1-20}$ acyl group means a formyl group, a succinyl group, a glutaryl group, a maleoyl group, a phthaloyl group, a $C_{2-6}$ alkanoyl group, a $C_{7-20}$ aroyl group, a $C_{2-20}$ heterocyclic carbonyl group, an (α-substituted) aminoacetyl group, or the like.

A $C_{2-6}$ alkanoyloxy group means an acetyloxy group, a propionyloxy group, or the like.

A $C_{7-20}$ aroyloxy group means a benzoyloxy group, a p-toluoyloxy group, a 4-phenylbenzoyloxy group, a naphthoyloxy group, or the like.

A $C_{1-20}$ acyloxy group means a $C_{2-6}$ alkanoyloxy group, a $C_{7-20}$ aroyloxy group, or the like.

A $C_{1-6}$ alkoxycarbonyl group means a methoxycarbonyl group, an ethoxycarbonyl group, an isopropoxycarbonyl group, a tert-butoxycarbonyl group, a 1,1-dimethylpropoxycarbonyl group, or the like.

A $C_{6-20}$ aryloxycarbonyl group means a phenyloxycarbonyl group, a naphthyloxycarbonyl group, or the like.

A $C_{6-20}$ aryl $C_{1-6}$ alkoxycarbonyl group means a benzyloxycarbonyl group, a phenethyloxycarbonyl group, a naphthylmethyloxycarbonyl group, or the like.

A $C_{1-6}$ alkoxycarbonyloxy group means a methoxycarbonyloxy group, an ethoxycarbonyloxy group, an isopropoxycarbonyloxy group, a tert-butoxycarbonyloxy group, a 1,1-dimethylpropoxycarbonyloxy group, or the like.

A $C_{1-6}$ alkylamino group means a methylamino group, an ethylamino group, a propylamino group, an isopropylamino group, a butylamino group, a sec-butylamino group, a tert-butylamino group, a pentylamino group, a hexylamino group, or the like.

A di($C_{1-6}$ alkyl)amino group means a dimethylamino group, a diethylamino group, a dipropylamino group, a diisopropylamino group, a dibutylamino group, a di(tert-butyl)amino group, a dipentylamino group, a dihexylamino group, an (ethyl)(methyl)amino group, a (methyl)(propyl) amino group, or the like.

A $C_{2-6}$ alkanoylamino group represents an acetylamino group, a propionylamino group, a valerylamino group, an isovalerylamino group, a pivaloylamino group, or the like.

A $C_{7-20}$ aroylamino group means a benzoylamino group or the like.

A $C_{1-20}$ acylamino group means a $C_{2-6}$ alkanoylamino group, a $C_{7-20}$ aroylamino group, or the like.

A $C_{1-6}$ alkylthio group means a methylthio group, an ethylthio group, a propylthio group, or the like.

A $C_{1-6}$ alkylsulfonyl group means a methylsulfonyl group, an ethylsulfonyl group, a propylsulfonyl group, or the like.

A $C_{6-20}$ arylsulfonyl group means a benzenesulfonyl group, a p-toluenesulfonyl group, a naphthalenesulfonyl group, or the like.

A $C_{1-6}$ alkylsulfonyloxy group means a methanesulfonyloxy group, an ethylsulfonyloxy group, a propylsulfonyloxy group, or the like.

A $C_{6-20}$ arylsulfonyloxy group means a phenylsulfonyloxy group, a naphthylsulfonyloxy group, or the like.

An aromatic ring means a benzene ring, a naphthalene ring, or the like.

A siloxane group means a disiloxane group, a trisiloxane groups, or the like.

A monocyclic nitrogen-containing $C_{2-20}$ heterocyclic group means an azetidinyl group, a pyrrolidinyl group, a pyrrolinyl group, a pyrrolyl group, a piperidyl group, a tetrahydropyridyl group, a pyridyl group, a homopiperidinyl group, an octahydroazocinyl group, an imidazolidinyl group, an imidazolinyl group, an imidazolyl group, a pyrazolidinyl group, a pyrazolinyl group, a pyrazolyl group, a piperazinyl group, a pyrazinyl group, a pyridazinyl group, a pyrimidinyl group, a homopiperazinyl group, a triazolyl group, a tetrazolyl group, or the like.

The monocyclic oxygen-containing $C_{2-20}$ heterocyclic group means a tetrahydrofuranyl group, a furanyl group, a tetrahydropyranyl group, a pyranyl group, or the like.

A monocyclic sulfur-containing $C_{2-20}$ heterocyclic group means a thienyl group or the like.

A monocyclic nitrogen- and oxygen-containing $C_{2-20}$ heterocyclic group means an oxazolyl group, an isoxazolyl group, an oxadiazolyl group, a morpholinyl group, or the like.

A monocyclic nitrogen- and sulfur-containing $C_{2-20}$ heterocyclic group means a thiazolyl group, an isothiazolyl group, a thiadiazolyl group, a thiomorpholinyl group, a 1-oxidethiomorpholinyl group, a 1,1-dioxidethiomorpholinyl group, or the like.

A monocyclic $C_{2-20}$ heterocyclic group means a monocyclic nitrogen-containing $C_{2-20}$ heterocyclic group, a monocyclic oxygen-containing $C_{2-20}$ heterocyclic group, a monocyclic sulfur-containing $C_{2-20}$ heterocyclic group, a monocyclic nitrogen- and oxygen-containing $C_{2-20}$ heterocyclic group, a monocyclic nitrogen- and sulfur-containing $C_{2-20}$ heterocyclic group, or the like.

A bicyclic nitrogen-containing $C_{2-20}$ heterocyclic group means an indolinyl group, an indolyl group, an isoindolinyl group, an isoindolyl group, a benzimidazolyl group, an indazolyl group, a benzotriazolyl group, a quinolyl group, a tetrahydroquinolinyl group, a tetrahydroisoquinolinyl group, an isoquinolinyl group, a quinolizinyl group, a cinnolinyl group, a phthalazinyl group, a quinazolinyl group, a dihydroquinoxalinyl group, a quinoxalinyl group, a naphthyridinyl group, a purinyl group, a pteridinyl group, a quinuclidinyl group, or the like.

A bicyclic oxygen-containing $C_{2-20}$ heterocyclic group means a 2,3-dihydrobenzofuranyl group, a benzofuranyl group, an isobenzofuranyl group, a chromanyl group, a chromenyl group, an isochromanyl group, a 1,3-benzodioxolyl group, a 1,3-benzodioxanyl group, a 1,4-benzodioxanyl group, or the like.

The bicyclic sulfur-containing $C_{2-20}$ heterocyclic group means a 2,3 dihydrobenzothienyl, a benzothienyl group, or the like.

A bicyclic nitrogen- and oxygen-containing $C_{2-20}$ heterocyclic group means a benzoxazolyl group, a benzisoxazolyl group, a benzoxadiazolyl group, a benzomorpholinyl group, a dihydropyranopyridyl group, a dihydrodioxinopyridyl group, a dihydropyridoxadinyl group, or the like.

A bicyclic nitrogen- and sulfur-containing $C_{2-20}$ heterocyclic group means a benzothiazolyl group, a benzisothiazolyl group, a benzothiadiazolyl group, or the like.

A bicyclic $C_{2-20}$ heterocyclic group means a bicyclic nitrogen-containing $C_{2-20}$ heterocyclic group, a bicyclic oxygen-containing $C_{2-20}$ heterocyclic group, a bicyclic sulfur-containing $C_{2-20}$ heterocyclic group, a bicyclic nitrogen- and oxygen-containing $C_{2-20}$ heterocyclic group, a bicyclic nitrogen- and sulfur-containing $C_{2-20}$ heterocyclic group, or the like.

A $C_{2-20}$ heterocyclic group means a monocyclic $C_{2-20}$ heterocyclic group or a bicyclic $C_{2-20}$ heterocyclic group.

A $C_{2-20}$ heterocyclic oxy group means a group in which a hydrogen atom (—H) bonded to a carbon atom forming a ring of a $C_{2-20}$ heterocyclic group has been substituted with an oxygen atom (—O—).

A $C_{2-20}$ heterocyclic thio group means a group in which a hydrogen atom (—H) bonded to a carbon atom forming a ring of a $C_{2-20}$ heterocyclic group has been substituted with a sulfur atom (—S—).

A $C_{1-18}$ silyl group means a trimethylsilyl group, a triethylsilyl group, a triisopropylsilyl group, a tributylsilyl group, a tert-butyldimethylsilyl group, a tert-butyldiphenylsilyl group, or the like.

Silylation means that a hydrogen atom of a hydroxyl group, an amino group, a carboxyl group, an amide group, or a mercapto group is substituted with a silyl group.

The $N^4$-acyl cytosine means cytosine protected with a $C_{1-20}$ acyl group which may be substituted an amino group, such as $N^4$-formyl cytosine, $N^4$-acetyl cytosine, $N^4$-propionyl cytosine, $N^4$-pivaloyl cytosine, $N^4$-benzoyl cytosine, $N^4$-(4-methylbenzoyl) cytosine, $N^4$-(4-bromobenzoyl) cytosine, $N^4$-(4-nitrobenzoyl) cytosine, or $N^4$-(4-methoxybenzoyl) cytosine.

The cytosine protected means a cytosine protected with a silyl group such as $N^4$,O-bis(trimethylsilyl)-4-amino-2-hydroxypyrimidine or $N^4$,O-bis(triethylsilyl)-4-amino-2-hydroxypyrimidine.

$N^4$-acyl cytosine protected means $N^4$-acyl cytosine protected with a silyl group such as 2-trimethylsilyloxy-4-acetylaminopyrimidine, $N^4$,O-bis(trimethylsilyl)-4-acetylamino-2-hydroxypyrimidine, 2-triethylsilyloxy-4-acetylaminopyrimidine, $N^4$,O-bis(triethylsilyl)-4-acetylamino-2-hydroxypyrimidine, 2-trimethylsilyloxy-4-benzoylaminopyrimidine, or $N^4$,O-bis(trimethylsilyl)-4-benzoylamino-2-hydroxypyrimidine.

A nucleic acid base means adenine which may be substituted, guanine which may be substituted, cytosine which may be substituted, thymine which may be substituted, or uracil which may be substituted.

A nucleic acid base protected means a nucleic acid base in which an amino group and/or a hydroxyl group is protected with a silyl group.

A leaving group means a halogen atom, a $C_{1-6}$ alkylsulfonyloxy group, a $C_{6-20}$ arylsulfonyloxy group, or the like. Each of the $C_{1-6}$ alkylsulfonyloxy group and the $C_{6-20}$ arylsulfonyloxy group may be substituted with one or more groups selected from the substituent group A.

Examples of the hydroxyl protecting group $R^{OH}$ include all groups that can be used as a protecting group of a typical hydroxyl group, and the groups described in "Protective Groups in Organic Synthesis" written by W. Greene et al., 4th edition, pp. 16-366, 2007, published by John Wiley & Sons, INC. are exemplified.

Specific examples thereof include a $C_{1-6}$ alkyl group, a $C_{2-6}$ alkenyl group, a $C_{6-20}$ aryl $C_{1-6}$ alkyl group, a $C_{1-6}$ alkoxy $C_{1-6}$ alkyl group, a $C_{1-20}$ acyl group, a $C_{1-6}$ alkoxycarbonyl group, a $C_{1-6}$ alkylsulfonyl group, a $C_{6-20}$ arylsulfonyl group, a tetrahydrofuranyl group, a tetrahydropyranyl group, and a silyl group. These groups may be substituted with one or more groups selected from the substituent group A.

Examples of the amino protecting group $R^{AM}$ include all groups that can be used as a protecting group of a typical amino group, and the groups described in "Protective Groups in Organic Synthesis" written by W. Greene et al., 4th edition, pp. 696-926, 2007, published by John Wiley & Sons, INC. are exemplified.

Specific examples thereof include a $C_{6-20}$ aryl $C_{1-6}$ alkyl group, a $C_{1-6}$ alkoxy $C_{1-6}$ alkyl group, a $C_{1-20}$ acyl group, a $C_{1-6}$ alkoxycarbonyl group, a $C_{6-20}$ aryloxycarbonyl group, a $C_{1-6}$ alkylsulfonyl group, a $C_{6-20}$ arylsulfonyl group, and a silyl group. These groups may be substituted with one or more groups selected from the substituent group A.

Examples of the carboxyl protecting group $R^{CA}$ include all groups that can be used as a protecting group of a typical carboxyl group, and the groups described in "Protective Groups in Organic Synthesis" written by W. Greene et al., 4th edition, pp. 533-646, 2007, published by John Wiley & Sons, INC. are exemplified.

Specific examples thereof include a $C_{1-6}$ alkyl group, a $C_{2-6}$ alkenyl group, a $C_{6-20}$ aryl group, a $C_{6-20}$ aryl $C_{1-6}$ alkyl group, a $C_{1-6}$ alkoxy $C_{1-6}$ alkyl group, and a silyl group. These groups may be substituted with one or more groups selected from the substituent group A.

Substituent group A: a halogen atom, a cyano group, a nitro group, an amino group, a hydroxyl group, a carboxyl group, a carbamoyl group, a sulfamoyl group, a $C_{1-6}$ alkyl group, a $C_{2-6}$ alkenyl group, a $C_{2-6}$ alkynyl group, a $C_{3-8}$ cycloalkyl group, a $C_{6-20}$ aryl group, a $C_{1-6}$ alkoxy group, a $C_{6-20}$ aryloxy group, a $C_{1-20}$ acyl group, a $C_{1-20}$ acyloxy group, a $C_{1-20}$ acylamino group, a $C_{1-6}$ alkoxycarbonyl group, a $C_{6-20}$ aryloxycarbonyl group, a $C_{1-6}$ alkoxycarbonyloxy group, a $C_{1-6}$ alkylamino group, a di($C_{1-6}$ alkyl) amino group, a $C_{1-6}$ alkylthio group, a $C_{1-6}$ alkylsulfonyl group, a $C_{6-20}$ arylsulfonyl group, a $C_{1-6}$ alkylsulfonyloxy group, a $C_{6-20}$ arylsulfonyloxy group, a $C_{1-18}$ silyl group, a $C_{2-20}$ heterocyclic group, and an oxo group.

The substituent group A may be substituted with the following substituent group B.

The hydroxyl group, the amino group, and the carboxyl group in the substituent group A may be protected.

Substituent group B: a halogen atom, a cyano group, a nitro group, an amino group, a hydroxyl group, a carboxyl group, a $C_{1-6}$ alkyl group, a $C_{6-20}$ aryl group, a $C_{1-6}$ alkoxy group, a $C_{2-20}$ heterocyclic group, and an oxo group.

The above-described substituents may be further substituted with a group in the substituent group B.

The hydroxyl group, the amino group, and the carboxyl group in the substituent group A may be protected.

Examples of the aliphatic hydrocarbon compound include pentane, hexane, and cyclohexane.

Examples of the halogenated hydrocarbon compound include methylene chloride, chloroform, and 1,2-dichloroethane.

Examples of the alcohol compound include methanol, ethanol, propanol, 2-propanol, butanol, and 2-methyl-2-propanol.

Examples of the ether compound include diethyl ether, diisopropyl ether, dioxane, tetrahydrofuran, anisole, ethylene glycol dimethyl ether, diethylene glycol dimethyl ether, and diethylene glycol diethyl ether.

Examples of the ester compound include methyl acetate, ethyl acetate, propyl acetate, isopropyl acetate, and butyl acetate.

Examples of the ketone compound include acetone, 2-butanone, and 4-methyl-2-pentanone.

Examples of the nitrile compound include acetonitrile.

Examples of the amide compound include N,N-dimethylformamide, N,N-dimethylacetamide, and N-methylpyrrolidone.

Examples of the sulfoxide compound include dimethyl sulfoxide and sulfolane.

Examples of carboxylic acid include acetic acid.

Examples of the aromatic hydrocarbon compound include benzene, chlorobenzene, dichlorobenzene, nitrobenzene, toluene, and xylene.

Examples of the urea compound include 1,3-dimethyl-2-imidazolidinone.

Examples of the organic base include triethylamine, pyridine, and N-methyl imidazole.

Examples of the inorganic base include sodium hydroxide, potassium hydroxide, sodium carbonate, potassium carbonate, sodium hydrogen carbonate, and sodium phosphate.

Abbreviations of respective substituents mean the following.

Ac: acetyl
Bn: benzyl
Bz: benzoyl
Et: ethyl
Me: methyl
Ms: methylsulfonyl or mesyl
Ph: phenyl
$^i$Pr: isopropyl
TBDPS: tert-butyl(diphenyl)silyl
TIPS: tris(propan-2-yl)silyl
Tol: (4-methylphenyl)carbonyl or toluoyl
RT (min): retention time (min)
Ts: (4-methylphenyl)sulfonyl or tosyl
Piv: pivaloyl
Tr: trityl $Ph_3C$
Nf: nonafluorobutanesulfonyl
CBS: 4-chlorobenzenesulfonyl
TCBS: 2,4,5-trichlorobenzenesulfonyl
Tf: trifluoromethanesulfonyl
N3: azide
ClBn: 4-chlorobenzyl
DMI: 1,3-dimethyl-2-imidazolidinone
DMF: N,N-dimethylformamide

EXAMPLES

Unless otherwise specified, in silica gel column chromatography, an SNAP KP-Sil Cartridge manufactured by Biotage Japan Ltd., or an FR-260 Hi-Flash™ Column or Wakogel C-200 manufactured by YAMAZEN corporation was used. The mixing ratio in the eluent was a volume ratio. For example, "hexane/ethyl acetate=90/10 to 50/50" means that an eluent of "hexane/ethyl acetate=90/10" was changed to an eluent of "hexane/ethyl acetate=50:50".

In the measurement of a $^1$H-NMR spectrum, tetramethylsilane was used as an internal standard, Bruker AV400N (manufactured by Bruker Corporation) or Bruker AV300 (manufactured by Bruker Corporation) was used, and all δ values were shown in ppm.

In the measurement of an $^{19}$F-NMR spectrum, Bruker AV400N (manufactured by Bruker Corporation) was used, and all δ values were shown in ppm.

LC/MS analysis was performed under the following conditions.
  Measuring instrument: SQD manufactured by WATERS
  Column: BEH C18 1.7 μm, 2.1×30 mm manufactured by WATERS
  Solvent: liquid A: 0.1% formic acid/water
    liquid B: 0.1% formic acid/acetonitrile
  Gradient cycle: 0.00 min (liquid A/liquid B=95/5), 2.00 min (liquid A/liquid B=5/95), 3.00 min (liquid A/liquid B=5/95), 3.01 min (liquid A/liquid B=100/0), 3.80 min (liquid A/liquid B=100/0)
  Flow rate: 0.5 mL/min
  Column temperature: room temperature
  Ionization method: electron spray ionization method (Electron Spray Ionization: ESI positive and negative ion peaks are detected)
  Detection wavelength: 254 nm Example 1

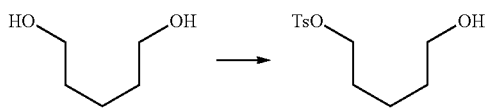 [SMILES: OCCCCCO ; Cc1ccc(S(=O)(=O)OCCCCCO)cc1]

5.7 g of p-toluenesulfonyl chloride was added to a solution of 9.4 g of pentane-1,5-diol in 100 mL of ethyl acetate at 0° C. to 10° C., and 8.4 mL of triethylamine was added dropwise thereto. After the reaction mixture was stirred at room temperature for 100 minutes, ethyl acetate and water were added thereto, then, the organic layer was collected by separation, and washed with a saturated sodium chloride aqueous solution. The solvent was distilled off under reduced pressure, and the obtained residue was purified by silica gel column chromatography (ethyl acetate/hexane=1/4→4/1), whereby 3.8 g of 5-(((4-methylphenyl)sulfonyl)oxy)pentan-1-ol was obtained as a colorless oily material.
$^1$H-NMR(CDCl$_3$) δ value: 7.79(2H,d,J=8.4 Hz),7.35(2H,d,J=8.4 Hz),4.04(2H,t,J=6.5 Hz),3.60(2H,t,J=6.3 Hz),2.45(3H,s),1. 73-1.33(7H,m).

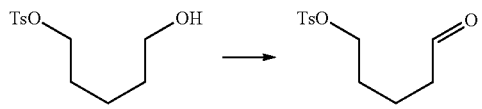 [SMILES: Cc1ccc(S(=O)(=O)OCCCCCO)cc1 ; Cc1ccc(S(=O)(=O)OCCCCC=O)cc1]

3.05 g of 1,1,1-triacetoxy-1,1-dihydro-1,2-benziodoxol-3 (1H)-one (Dess-Martin periodinane) was added to a solution of 1.55 g of 5-(((4-methylphenyl)sulfonyl)oxy)pentan-1-ol in 15 mL of dichloromethane at 0° C. to 10° C., and the resultant product was stirred for 1 hour. Ethyl acetate, a saturated sodium hydrogen carbonate aqueous solution, and a sodium thiosulfate aqueous solution were added to the reaction mixture, and the resultant product was stirred at room temperature for 10 minutes. The organic layer was collected by separation, washed sequentially with a saturated sodium hydrogen carbonate aqueous solution, a sodium thiosulfate aqueous solution, pure water, and a saturated sodium chloride aqueous solution, and dried over anhydrous magnesium sulfate. The solvent was distilled off under reduced pressure, whereby 1.30 g of 5-(((4-methylphenyl)sulfonyl)oxy)pentanal was obtained as a colorless oily material.

$^1$H-NMR(CDCl$_3$) δ value: 9.73(1H,t,J=1.4 Hz),7.78(2H,d J=8.4 Hz),7.35(2H,d,J=8.4 Hz),4.09-3.99(2H,m),2.46-2.41 (5H,m), 1.72-1.30(4H,m).

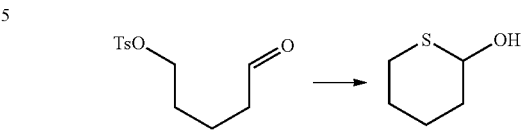

240 mg of sodium hydrogen sulfide n-hydrate was added to a solution of 1.30 g of 5-(((4-methylphenyl)sulfonyl)oxy)pentanal in 15 mL of N,N-dimethylformamide at 0° C. to 10° C., and the resultant product was stirred at 0° C. to 10° C. for 1 hour. Ethyl acetate and water were added to the reaction mixture, and the organic layer was collected by separation. The organic layer was washed three times with a saturated sodium chloride aqueous solution, and dried over anhydrous magnesium sulfate. The solvent was distilled off under reduced pressure, and the obtained residue was purified by silica gel column chromatography (ethyl acetate/hexane=1/19→ethyl acetate), whereby 0.18 g of thian-2-ol was obtained as a colorless oily material.
$^1$H-NMR(CDCl$_3$) δ value: 4.97(1H,m),3.07-2.98(1H,m), 2.48-2.39(1H,m),2.10-1.52(7H,m).

Example 2

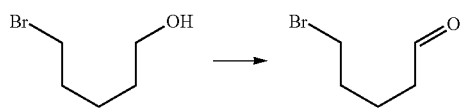 [SMILES: OCCCCCBr ; O=CCCCCBr]

1.90 g of 1,1,1-triacetoxy-1,1-dihydro-1,2-benziodoxol-3 (1H)-one (Dess-Martin periodinane) was added to a solution of 0.50 g of 5-bromopentan-1-ol in 10 mL of dichloromethane at 0° C. to 10° C., and the resultant product was stirred at room temperature for 3 hours. Ethyl acetate, a saturated sodium hydrogen carbonate aqueous solution, and a sodium thiosulfate aqueous solution were added to the reaction mixture, and the resultant product was stirred at room temperature for 10 minutes. The organic layer was collected by separation, washed sequentially with a saturated sodium hydrogen carbonate aqueous solution, a sodium thiosulfate aqueous solution, pure water, and a saturated sodium chloride aqueous solution, and dried over anhydrous magnesium sulfate. The solvent was distilled off under reduced pressure, whereby 0.34 g of 5-bromopentanal was obtained as a colorless oily material.
$^1$H-NMR(CDCl$_3$) δ value: 9.79(1H,s),3.45-3.36(2H,m), 2.52-2.43(2H,m),1.97-1.72(4H,m).

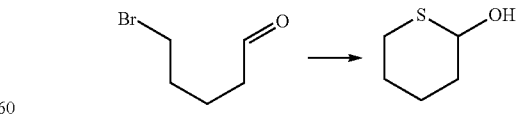

0.29 g of sodium hydrogen sulfide n-hydrate was added to a solution of 0.20 g of 5-bromopentanal in 2 mL of N,N-dimethylformamide at 0° C. to 10° C., and the resultant product was stirred at 0° C. to 10° C. for 1 hour. Ethyl acetate and water were added to the reaction mixture, and the organic layer was collected by separation. The organic layer was washed three times with a saturated sodium chloride aqueous solution, and dried over anhydrous magnesium sulfate. The solvent was distilled off under reduced pressure, and the obtained residue was purified by silica gel column chromatography (ethyl acetate/hexane=1/19→ethyl acetate), whereby 27 mg of thian-2-ol was obtained as a colorless oily material.

Example 3

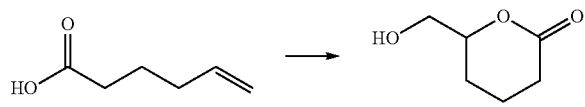

47.4 g of 3-chloroperbenzoic acid was added to a solution of 18.3 g of 5-hexenoic acid in 320 mL of dichloromethane at room temperature, the resultant product was stirred at room temperature for 12 hours. The precipitated white precipitate was removed by filtration using Celite, then, 3.7 g of 10-camphorsulfonic acid was added to this filtration solution at 0° C. to 10° C., and the resultant product was stirred at room temperature for 1 hour. After 20 g of sodium hydrogen carbonate was added thereto, 200 mL of the solvent was distilled off under reduced pressure, then, the precipitate was separated by filtration, and the solvent was distilled off under reduced pressure. The obtained residue was purified by silica gel column chromatography, whereby 14.4 g of 6-(hydroxymethyl)-oxan-2-one was obtained as a colorless oily material.

$^1$H-NMR(CDCl$_3$) δ value: 4.45-4.38(1H,m),3.84-3.61(2H,m),2.70-2.39(2H,m),2.05-1.40(5H,m).

7.7 mL of benzoyl chloride was added to a solution of 7.2 g of 6-(hydroxymethyl)-oxan-2-one in 50 mL of pyridine at 0° C. to 10° C., and the resultant product was stirred at room temperature overnight. Ethyl acetate and water were added to the reaction mixture, and the organic layer was collected by separation. The organic layer was washed two times with dilute hydrochloric acid and once with a saturated sodium chloride aqueous solution, and dried over anhydrous magnesium sulfate. The solvent was distilled off under reduced pressure, then, the obtained residue was combined with the composition synthesized in the same manner, and the resultant product was purified by silica gel column chromatography, whereby 15.7 g of (6-oxan-2-yl)methyl benzoate was obtained as a white solid.

$^1$H-NMR(CDCl$_3$) δ value: 8.08-8.00(2H,m),7.60-7.53(1H,m),7.49-7.41(2H,m),4.72-4.62(1H,m),4.53-4.41(2H,m),2.72-2.44(2H,m),2.09-1.65(4H,m).

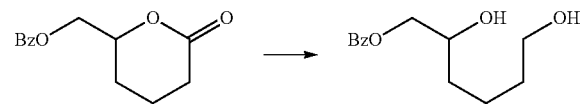

After 1.55 g of sodium tetrahydroborate was added to a solution of 8.0 g of (6-oxan-2-yl)methyl benzoate in 34 mL of methanol and 68 mL of tetrahydrofuran at 0° C. to 10° C. in a nitrogen atmosphere, the resultant product was stirred for 15 minutes, then, 0.1 g of sodium tetrahydroborate was added thereto, and the resultant product was stirred for 10 minutes. Ice, ammonium chloride, and ethyl acetate were added to the reaction mixture, and the organic layer was collected by separation. The organic layer was washed sequentially with water and a saturated sodium hydrogen carbonate aqueous solution, and dried over anhydrous magnesium sulfate. The solvent was distilled off under reduced pressure, whereby 7.8 g of 2,6-dihydroxyl benzoate was obtained as a colorless oily material.

$^1$H-NMR(CDCl$_3$) δ value: 8.08-8.03(2H,m),7.62-7.54(1H,m),7.49-7.41(2H,m),4.40 (1H,dd,J=3.3,11.4 Hz),4.24(1H,dd,J=7.1,11.6Hz),4.01(1H,m),3.73-3.62(2H,m),1.71-1.40(8H,m).

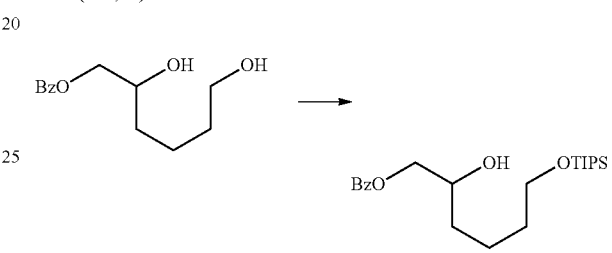

7.7 mL of triisopropylsilyl chloride was added dropwise to a solution of 7.8 g of 2,6-dihydroxyl benzoate and 2.92 g of imidazole in 100 mL of N,N-dimethylformamide at 5° C. to 10° C. in a nitrogen atmosphere. After the reaction mixture was stirred at room temperature for 14 hours, ethyl acetate and water were added thereto, and the organic layer was collected by separation, washed sequentially four times with water and once with a saturated sodium chloride aqueous solution, and dried over anhydrous magnesium sulfate. The solvent was distilled off under reduced pressure, and the obtained residue was purified by silica gel column chromatography, whereby 10.3 g of 2-hydroxy-6-((tris(propan-2-yl)silyl)oxy)hexyl benzoate was obtained as a colorless oily material.

$^1$H-NMR(CDCl$_3$) δ value: 8.08-8.02(2H,m),7.61-7.53(1H,m),7.49-7.40(2H,m),4.43-4.36(1H,m),4.28-4.19(1H,m),4.08-3.98(1H,m),3.75-3.67(2H,m),2.17-2.12(1H,m),1.65-1.45(6H,m),1.16-0.98(21H,m).

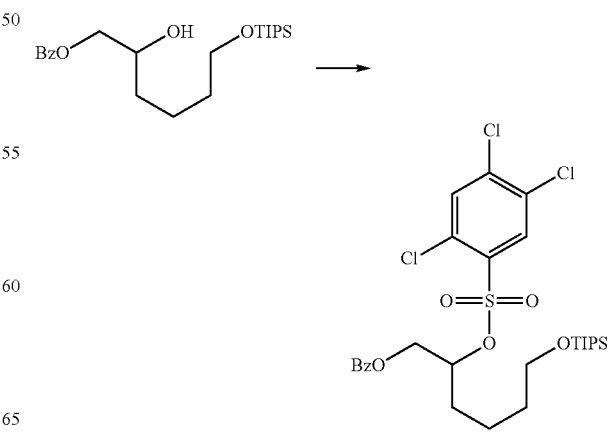

0.46 g of 2,4,5-trichlorobenzenesulfonyl chloride and 0.18 mL of N-methylimidazole were added to a solution of 0.59 g of 2-hydroxy-6-((tris(propan-2-yl)silyl)oxy)hexyl benzoate in 10 mL of acetonitrile at 0° C. to 10° C., and the resultant product was stirred at room temperature for 20 hours. Next, 0.09 mL of N-methylimidazole and 0.23 g of 2,4,5-trichlorobenzenesulfonyl chloride were added thereto, and the resultant product was stirred for 105 minutes. Next, 0.09 mL of N-methylimidazole and 0.20 g of 2,4,5-trichlorobenzenesulfonyl chloride were added thereto, and the resultant product was stirred for 75 minutes. After ethyl acetate and water were added to the reaction mixture, the organic layer was collected by separation, washed with a saturated sodium chloride aqueous solution, and dried over anhydrous magnesium sulfate. The solvent was distilled off under reduced pressure, and the obtained residue was purified by silica gel column chromatography, whereby 0.66 g of 2-(((2,4,5-trichlorophenyl)sulfonyl)oxy)-6-((tris(propan-2-yl)silyl)oxy)hexyl benzoate was obtained as a colorless oily material.

$^1$H-NMR(CDCl$_3$) δ value: 8.08(1H,s),7.87-7.81(2H,m),7.60-7.54(1H,m),7.47-7.39 (3H,m),5.10-5.00(1H,m),4.49-4.32(2H, m),3.72-3.62(2H,m),1.97-1.74(2H,m),1.63-1.49 (4H,m),1.13-0.98(21H,m).

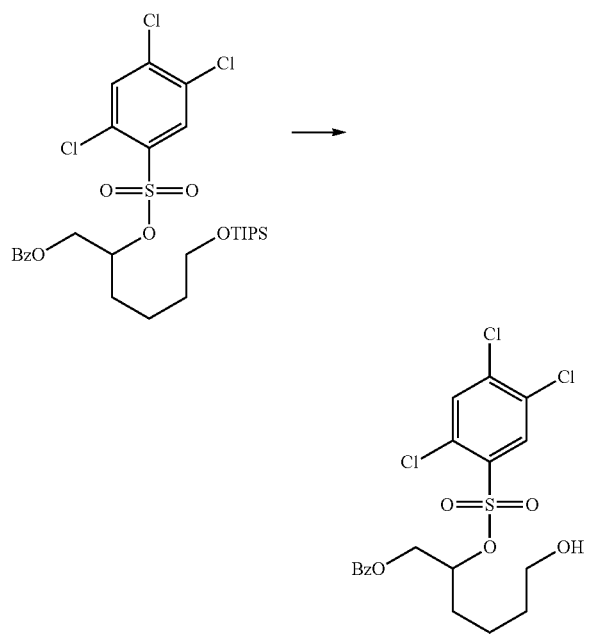

0.1 g of p-toluenesulfonic acid monohydrate was added to a solution of 0.66 g of 2-(((2,4,5-trichlorophenyl)sulfonyl)oxy)-6-((tris(propan-2-yl)silyl)oxy)hexyl benzoate in 10 mL of methanol and 5 mL of tetrahydrofuran, and the resultant product was stirred at room temperature for 2 hours. Next, 0.1 g of p-toluenesulfonic acid monohydrate was added thereto, and the resultant was stirred at room temperature for 1 hour. Ethyl acetate and a saturated sodium hydrogen carbonate aqueous solution were added to the reaction mixture. The organic layer was collected by separation, washed with a saturated sodium chloride aqueous solution, and dried over anhydrous magnesium sulfate. The solvent was distilled off under reduced pressure, whereby 0.48 g of 6-hydroxy-2-(((2,4,5-trichlorophenyl)sulfonyl)oxy)hexyl benzoate was obtained as a colorless oily material.

$^1$H-NMR(CDCl$_3$) δ value: 8.08(1H,s),7.87-7.80(2H,m),7.60-7.53(1H,m),7.44-7.36 (3H,m),5.10-5.00(1H,m),4.48-4.34(2H,m),3.70-3.61(2H,m),1.98-1.79(2H,m),1.68-1.51 (4H,m).

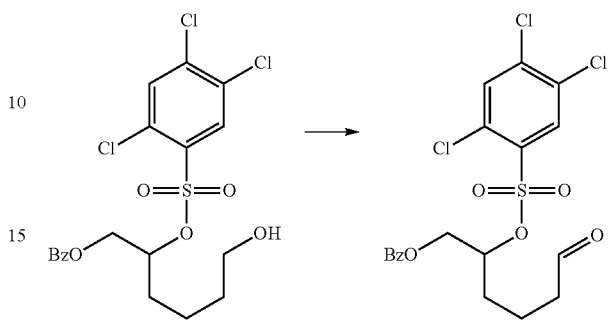

0.64 g of 1,1,1-triacetoxy-1,1-dihydro-1,2-benziodoxol-3 (1H)-one (Dess-Martin periodinane) was added to a solution of 0.48 g of 6-hydroxy-2-(((2,4,5-trichlorophenyl)sulfonyl)oxy)hexyl benzoate in 10 mL of dichloromethane at 0° C. to 10° C., and the resultant product was stirred at room temperature for 1 hour. Next, 0.21 g of 1,1,1-triacetoxy-1, 1-dihydro-1,2-benziodoxol-3 (1H)-one (Dess-Martin periodinane) was added thereto, and the resultant product was stirred at room temperature for 30 minutes. Ethyl acetate, a saturated sodium hydrogen carbonate aqueous solution, and a sodium thiosulfate aqueous solution were added to the reaction mixture, and the resultant product was stirred at room temperature for 10 minutes. The organic layer was collected by separation, washed sequentially with sodium thiosulfate and a saturated sodium chloride aqueous solution, and dried over anhydrous magnesium sulfate. The solvent was distilled off under reduced pressure, and the obtained residue was purified by silica gel column chromatography, whereby 0.26 g of 6-oxo-2-(((2,4,5-trichlorophenyl)sulfonyl)oxy)hexyl benzoate was obtained as a colorless oily material.

$^1$H-NMR(CDCl$_3$) δ value: 9.73(1H,t,J=1.4 Hz),8.08(1H, s),7.86-7.80(2H,m),7.62-7.54(1H,m),7.46-7.37(3H,m),5.10-5.00(1H,m),4.48-4.36(2H,m),2.60-2.51(2H,m),1.95-1.73(4H,m).

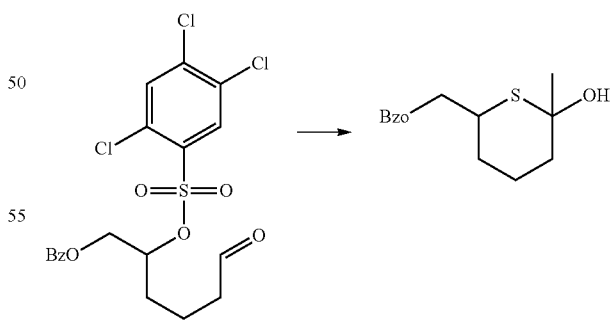

A solution of 45 mg of anhydrous sodium hydrogen sulfide in 0.5 mL of N,N-dimethylformamide was added to a solution of 0.26 g of 6-oxo-2-(((2,4,5-trichlorophenyl)sulfonyl)oxy)hexyl benzoate in 5 mL of N,N-dimethylformamide, and the resultant product was stirred at room temperature (about 25° C.) for 3 hours. Next, 30 mg of anhydrous sodium hydrogen sulfide was added thereto, and the resultant product was stirred at room temperature for 1 hour. Ethyl acetate and a saturated sodium chloride aqueous solution were added to the reaction mixture, and the organic layer was collected by separation. The organic layer was washed with a saturated sodium chloride aqueous solution, and dried over anhydrous magnesium sulfate. The solvent was distilled off under reduced pressure, and the obtained residue was purified by silica gel column chromatography, whereby 26 mg of (6-hydroxythian-2-yl)methyl benzoate was obtained as a colorless oily material.

As a result of $^1$H-NMR measurement, the above-obtained material was a mixture of an isomer A and an isomer B, and the ratio (A:B) thereof was 2:1.

$^1$H-NMR(CDCl$_3$) δ value: 8.09-8.02(2H,m),7.60-7.53 (1H,m),7.48-7.40(2H,m),5.16-5.06(0.67H,m),4.99-4.91 (0.33H,m),4.74-4.57(0.66H,m),4.40-4.24(1.34H,m),3.70-3.59(0.67H,m),3.23-3.13(0.33H,m),2.27-1.42(6H, m).

Example 4

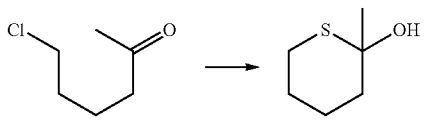

7.21 g of sodium hydrogen sulfide n-hydrate was added to a solution of 4.04 g of 6-chlorohexan-2-one in 100 mL of N,N-dimethylformamide at 0° C. to 10° C., and the resultant product was stirred at 0° C. to 10° C. for 4 hours. Ethyl acetate and water were added to the reaction mixture, and the organic layer was collected by separation. The organic layer was washed sequentially with water and a saturated sodium chloride aqueous solution, and dried over anhydrous magnesium sulfate. The solvent was distilled off under reduced pressure, and the obtained residue was purified by silica gel column chromatography, whereby 0.54 g of 2-methylthian-2-ol was obtained as a colorless oily material.

$^1$H-NMR(CDCl$_3$) δ value: 3.06-2.95(1H,m),2.53-2.41 (1H,m),2.02-1.49(10H,m).

Example 5

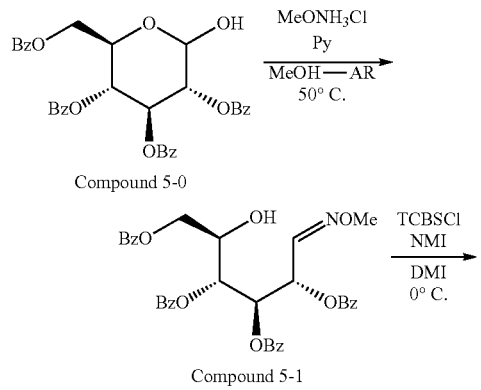

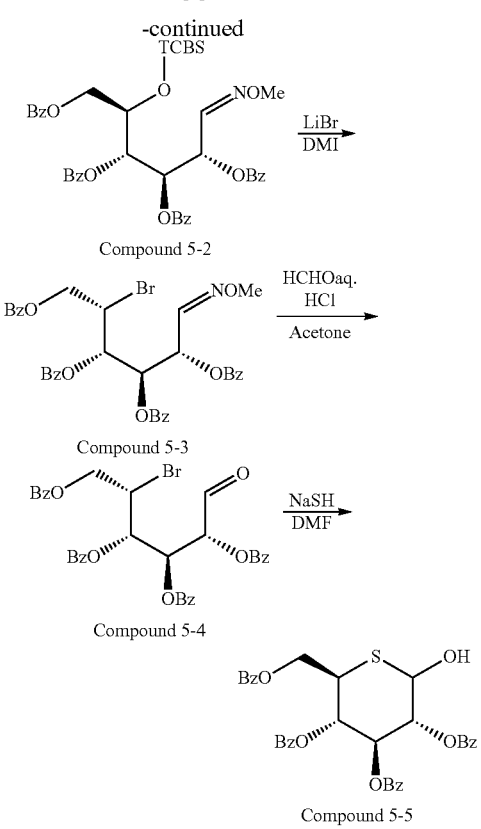

(1)
21.4 g of O-methylhydroxylamine hydrochloride was added to a solution of 2.1 g of a compound 5-0 in 20 mL of methanol, 4 mL of acetonitrile, and 1.4 mL of pyridine, and the resultant product was stirred at 50° C. for 1.5 hours. 20 mL of ethyl acetate and 20 mL of 1 mol/L hydrochloric acid were added to the reaction mixture, and the aqueous layer was removed. The organic layer was washed with water and saturated saline in this order and dried over anhydrous sodium sulfate, and the solvent was distilled off under reduced pressure, whereby 2.38 g of a compound 5-1 was obtained.

As a result of $^1$H-NMR measurement, the above-obtained compound was a mixture of an isomer A and an isomer B, and the ratio (A:B) thereof was 3:1.

$^1$H-NMR(CDCl$_3$) δ value: 8.10-7.82(8H+8H,m,A+B), 7.63-7.30(13H+12H,m,A+B), 6.71(d,1H,J=6.0 Hz,B), 6.58 (t,1H,J=5.9 Hz,B), 6.21(dd,1H,J=2.1 Hz, 7.5 Hz,A), 6.23-6.19(m,1H,B), 6.02(dd,1H,J=5.7 Hz, 7.5 Hz,A), 5.76(dd, 1H,J=2.4 Hz, 9.0 Hz,A), 5.71(dd,1H,J=3.3 Hz, 8.4 Hz,B), 4.57-4.53(1H+1H,m,A+B), 4.42-4.34(1H+1H,m,A+B), 4.26-4.15(1H+1H,m,A+B), 3.77(3H,s,A), 3.76(3H,s,B), 3.60(d,1H,J=5.1 Hz,A), 3.42(d,1H,J=5.7 Hz,B), (2)
0.55 mL of 1-methylimidazole was added dropwise to a solution of 2.17 g of the compound 5-1 and 1.07 g of 2,4,5-trichlorobenzenesulfonyl chloride in 20 mL of acetonitrile at 0° C. to 4° C., and the resultant product was stirred at room temperature for 1 hour. The residue obtained by distilling off the solvent under reduced pressure was purified by silica gel column chromatography, whereby 2.77 g of a compound 5-2 was obtained.

As a result of $^1$H-NMR measurement, the above-obtained compound was a mixture of an isomer A and an isomer B, and the ratio (A:B) thereof was 3:1.

$^1$H-NMR(CDCl$_3$) δ value: 8.10-7.82(8H+8H,m,A+B), 7.63-7.30(14H+13H,m,A+B), 7.19(1H,s,A), 7.14(1H,s,B), 6.70(d,1H,J=5.7 Hz,B), 6.54(t,1H,J=5.7 Hz,B), 6.17(dd,1H, J=3.1 Hz, 7.3 Hz,A), 6.13(dd,1H,J=3.4 Hz,5.4 Hz, B), 6.06-6.01(m,2H,A), 5.94(t,1H,J=4.1 Hz,B), 5.50-5.43(1H+ 1H,m,A+B), 4.82-4.66(2H+2H,m,A+B), 3.76(3H,s,A), 3.75 (3H,s,B), (3)

0.54 g of lithium bromide was added to a solution of 2.69 g of the compound 5-2 in 15 mL of 1,3-dimethyl-2-imidazolidinone, and the resultant product was stirred at 50° C. for 9 hours. Ethyl acetate and water were added to the reaction mixture. The organic layer was collected by separation and washed with water and a saturated sodium chloride aqueous solution, and the solvent was distilled off under reduced pressure. The obtained residue was purified by silica gel column chromatography (hexane/ethyl acetate=87/13 to 66/34), whereby 0.91 g of a compound 5-3 was obtained as a white solid.

As a result of $^1$H-NMR measurement, the above-obtained compound was a mixture of an isomer A and an isomer B, and the ratio (A:B) thereof was 3:1.

$^1$H-NMR(CDCl$_3$) δ value: 8.10-7.85(8H+8H,m,A+B), 7.60-7.44(5H+4H,m,A+B), 7.40-7.23(8H+8H,m,A+B), 6.70(d,1H,J=4.8 Hz,B), 6.49(dd, 1H,J=2.4 Hz,4.8 Hz,B), 6.44(dd,1H,J=2.5 Hz, 8.1 Hz,B), 6.21(dd,1H,J=3.9 Hz,7.2 Hz,A), 6.07-6.03(m,2H,A), 6.00(dd,1H,J=1.9 Hz, 8.4 Hz,A), 4.80-4.70(2H+2H,m,A+B), 4.49-4.37(1H+1H,m,A+ B), 3.97(3H,s,B), 3.76(3H,s,A)

(4)

0.35 mL of 1 mol/L hydrochloric acid was added to a mixture of 1.22 g of the compound 5-3, 1.4 mL of a 36% formalin aqueous solution, and 12 mL of acetone, followed by stirring at 50° C. for 3 hours, and 0.35 mL of 1 mol/L hydrochloric acid was added thereto, followed by stirring at 50° C. for 1 hour. 40 mL of ethyl acetate was added thereto, then, the organic layer was washed with water and a saturated sodium chloride aqueous solution and dried over anhydrous sodium sulfate, and the solvent was distilled off under reduced pressure, whereby 1.27 g of a compound 5-4 was obtained.

$^1$H-NMR(CDCl$_3$, only decipherable signal) δ value: 9.68 (1H,s), 8.07-7.85(8H,m), 7.60-7.44(4H,m), 7.40-7.28(8H, m), 6.39(dd,1H,J=2.4 Hz,7.8 Hz), 6.13(dd,1H,J=2.4 Hz, 7.8 Hz), 5.79(d,1H,J=2.7 Hz,B)

(5)

0.2 g of a 15% sodium hydrogen sulfide aqueous solution was added to a solution of 1.27 g of the compound 5-4 in 8.8 mL of N,N-dimethylformamide at 0° C. to 10° C., and the resultant product was stirred for 20 minutes. 30 mL of ethyl acetate and 10 mL of water were added to the reaction mixture, and the aqueous layer was removed. The organic layer was washed with water and a saturated sodium chloride aqueous solution and dried over anhydrous sodium sulfate, and the solvent was distilled off under reduced pressure. The obtained residue was purified by silica gel column chromatography (hexane/ethyl acetate=80/20 to 59/41), whereby 0.52 g of a compound 5-5 was obtained as a white solid.

$^1$H-NMR(CDCl$_3$) δ value: 8.07-7.75(8H,m), 7.60-7.18 (12H,m), 6.39(dd,1H,J=2.4 Hz,7.8 Hz), 6.25(t,1H,J=9.9 Hz), 5.97(t,1H,J=10.2 Hz), 5.62(dd,1H,J=2.6 Hz,9.9 Hz), 5.47(t,1H,J=2.7 Hz), 4.63(dd,1H,J=3.9 Hz,12 Hz), 4.55(dd, 1H,J=5.1 Hz,12 Hz), 4.17-4.08(m,1H), 2.55(d,1H,J=1.8 Hz)

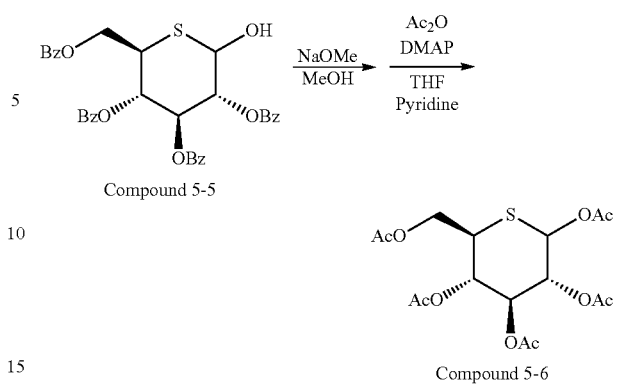

Compound 5-5

Compound 5-6

(6)

One drop of a 28% sodium methoxide methanol solution was added to a solution of 0.12 g of the compound 5-5 in 6 mL of methanol, and the resultant product was stirred at room temperature for 1 hour. 20 mL of ethyl acetate was added to the reaction mixture, and the solvent was distilled off under reduced pressure. After 20 mL of tetrahydrofuran was further added thereto, the solvent was distilled off under reduced pressure, 3 mL of tetrahydrofuran, 0.5 mL of acetic anhydride, and 1.0 mL of pyridine were added thereto, followed by stirring for 4 hours, 3 mg of N,N-dimethylaminopyridine was added thereto, and the resultant product was stirred for 2 hours. After ethyl acetate was added to the reaction mixture, the organic layer was washed with dilute hydrochloric acid, water, and a saturated sodium chloride aqueous solution, and dried over anhydrous sodium sulfate, and the solvent was distilled off under reduced pressure. The obtained residue was purified by silica gel column chromatography (hexane/ethyl acetate=60/40 to 39/61), whereby 0.06 g of a compound 5-6 was obtained as an oily material.

As a result of $^1$H-NMR measurement, the above-obtained compound was a mixture of an isomer A and an isomer B, and the ratio (A:B) thereof was 1:0.22.

$^1$H-NMR(CDCl$_3$) δ value: 6.16(1H,d,J=3.3 Hz,A), 5.89 (1H,d,J=8.7 Hz,B), 5.45(1H,t,J=9.8 Hz,A), 5.33(1H,t, J=10.1 Hz,A), 5.42-5.35(2H,m,B), 5.25(1H,dd,J=3.3 Hz,10.2 Hz,A), 5.12(1H,t,J=9.0 Hz,B), 4.39(1H,dd,J=4.8 Hz,12.0 Hz, A), 4.32(1H,dd,J=5.7 Hz,12.3 Hz,B), 4.17(1H, dd,J=3.9 Hz,12.3 Hz,B), 4.07(1H,dd,J=3.0 Hz,12.3 Hz,A), 3.59(1H,ddd,J=3.0 Hz,4.8 Hz,10.8 Hz,A), 3.32(1H,ddd, J=3.9 Hz,5.7 Hz,9.9 Hz,B), 2.19(3H,s,A), 2.09(3H,s,B), 2.08(3H,s,A), 2.08(3H,s,B), 2.05(3H,s,A), 2.04(3H,s,B), 2.03(3H,s,B), 2.02(3H,s,A), 2.01(3H,s,B), 2.00(3H,s,A)

It is possible to synthesize a compound effective as a medicine using the compound 5-6 as a starting material by the method described in WO2004/014931A, WO2004/106352A, or JP2010-059173A.

Example 6

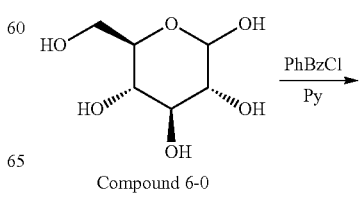

Compound 6-0

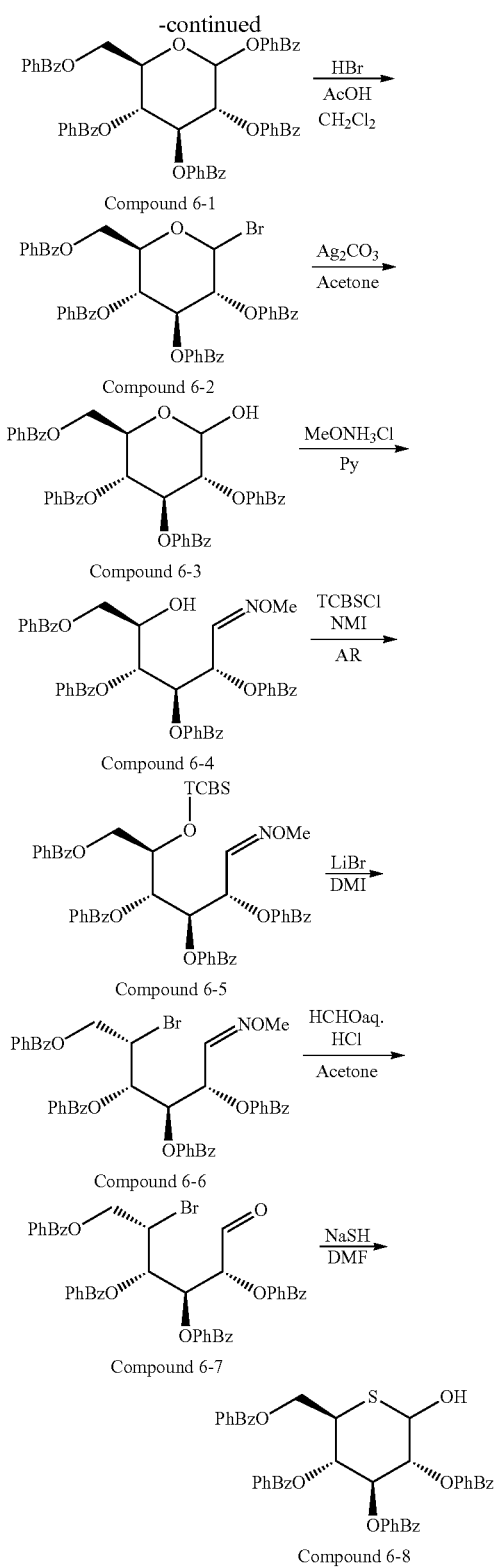

Compound 6-1
Compound 6-2
Compound 6-3
Compound 6-4
Compound 6-5
Compound 6-6
Compound 6-7
Compound 6-8

(1)
23.87 g of 4-phenylbenzoyl chloride was added to a solution of 3.6 g of a compound 6-0 and 0.12 g of N,N-dimethylaminopyridine in 200 mL of pyridine over a period of 10 minutes while maintaining the inner temperature at −5° C., and the resultant product was allowed to react at room temperature for 21 hours, followed by heating at 45° C. for 1 hour. 200 mL of water and 50 mL of a saturated sodium hydrogen carbonate aqueous solution were added to the reaction mixture, and the precipitated white solid was collected by filtration, washed with a sodium hydrogen carbonate aqueous solution, dilute hydrochloric acid, and water, and air-dried, whereby 17.07 g of a white solid was obtained. 4.77 g of 4-phenylbenzoyl chloride was added to a solution of 11.2 g of the obtained white solid in 100 mL of pyridine, and the same operation was repeated, whereby 10.8 g of a compound 6-1 was obtained as a white solid.

$^1$H-NMR(CDCl$_3$) δ value: 8.20-7.95(10H,m), 7.70-7.30 (35H,m), 6.93(1H,d,J=3.9 Hz), 6.41(1H,t,J=9.9 Hz), 5.94 (1H,t,J=9.9 Hz), 5.76(1H,dt,J=3.9 Hz,10.2 Hz), 4.75-4.64 (2H,m), 4.62-4.53(1H,m)

(2)
2 mL of a 30% hydrogen bromide/acetic acid solution was added to a solution of 5.40 g of the compound 6-1 in 50 mL of methylene chloride and 50 mL of acetic acid, and the resultant product was stirred at 50° C. for 3 hours. 2 mL of a 30% hydrogen bromide/acetic acid solution was additionally added, and the resultant product was stirred at 50° C. for 6.5 hours. After 50 mL of water was added to the reaction mixture, the aqueous layer was removed, 100 mL of ethyl acetate was added thereto, the organic layer was neutralized with a saturated sodium hydrogen carbonate aqueous solution and washed with water and saturated saline, and the solvent was distilled off under reduced pressure, whereby 4.47 g of a compound 6-2 was obtained as a white solid.

$^1$H-NMR (CDCl$_3$) δ value: 8.15-7.87 (8H, m), 7.65-7.30 (28H, m), 6.92 (1H, d, J=3.9 Hz), 6.34 (1H, t, J=9.9 Hz), 5.90 (1H, t, J=10.1 Hz), 5.40 (1H, dd, J=3.9 Hz, 9.9 Hz), 4.84-4.68 (2H, m), 4.58 (1H, dd, J=4.2 Hz, 12.3 Hz)

(3)
0.8 mL of water and 1.62 g of silver carbonate were added to a solution of 3.42 g of the compound 6-2 in 150 mL of acetone, and the resultant was stirred at 50° C. for 1 hour. The silver carbonate was separated from the reaction mixture by filtration, and the solvent was distilled off under reduced pressure. The obtained residue was washed with ethyl acetate and hexane, whereby 2.84 g of a compound 6-3 was obtained as a white solid.

$^1$H-NMR(CDCl$_3$) δ value: 8.18-7.96(8H,m), 7.60-7.35 (28H,m), 6.33(1H,t,J=9.9 Hz), 5.86-5.76(2H,m),5.39(1H, dd,J=3.6 Hz,6.6 Hz),4.80-4.50(3H,m)

(4)
27 mL of pyridine and 0.50 g of O-methylhydroxylamine hydrochloride were added to 2.74 g of the compound 6-3, and the resultant product was stirred at 50° C. for 4 hours. After 50 mL of ethyl acetate was added to the reaction mixture, the organic layer was washed with saline, 1 mol/L hydrochloric acid, and saturated saline, and dried over anhydrous sodium sulfate, and the residue obtained by distilling off the solvent under reduced pressure was purified by silica gel column chromatography, whereby 2.61 g of a compound 6-4 was obtained as a glassy solid.

As a result of $^1$H-NMR measurement, the above-obtained compound was a mixture of an isomer A and an isomer B, and the ratio (A:B) thereof was 2.5:1.

$^1$H-NMR(CDCl$_3$) δ value: 8.22-7.96(8H+8H,m,A+B), 7.70-7.35(29H+28H,m,A+B), 6.75(1H,d,J=5.7 Hz,B), 6.61 (1H,dd,J=4.5 Hz,6.0 Hz,B), 6.20-6.25(1H,m,B), 6.26(1H, dd,J=2.1 Hz,6.6 Hz,A), 6.15(1H,dd,J=5.4 Hz,6.6 Hz,A), 5.87-5.78(1H+1H,m,A+B), 4.67-4.58(1H+1H,m,A+B), 4.47-4.40(1H+1H,m,A+B), 4.30-4.20(1H+1H,m,A+B), 3.88(3H,s,B), 3.80(3H,s,A)

(5)

0.16 mL of 1-methylimidazole was added dropwise to a solution of 0.93 g of the compound 6-4 and 0.31 g of 2,4,5-trichlorobenzenesulfonyl chloride in 10 mL of acetonitrile at 0° C. to 5° C., and the resultant product was stirred at room temperature for 5 hours. 30 mL of ethyl acetate was added to the reaction mixture, and the resultant product was washed with water and saturated saline. After the white solid precipitated when washing was separated by filtration, the organic layer was dried over anhydrous sodium sulfate, and the residue obtained by distilling off the solvent under reduced pressure was purified by silica gel column chromatography, whereby 1.00 g of a compound 6-5 was obtained as a glassy solid.

As a result of $^1$H-NMR measurement, the above-obtained compound was a mixture of an isomer A and an isomer B, and the ratio (A:B) thereof was 2.5:1.

$^1$H-NMR(CDCl$_3$) δ value: 8.17-7.87(9H+9H,m,A+B), 7.69-7.35(29H+28H,m,A+B), 6.77(1H,d,J=5.4 Hz,B), 6.61 (1H,t,J=5.3 Hz,B), 6.25-6.17(1H+1H,m,A+B), 6.14-6.08 (2H,m,A), 6.03(1H,t,J=4.1 Hz,B), 5.58-5.50(1H+1H,m,A+B), 4.81(1H,brs,A) 4.79(3H,brs,B), 3.82(3H,s,B), 3.81(3H,s,A)

(6)

87 mg of lithium bromide was added to a solution of 0.59 g of the compound 6-5 in 2.5 mL of 1,3-dimethyl-2-imidazolidinone, and the resultant product was stirred at 50° C. for 11 hours. 50 mL of ethyl acetate was added to the reaction mixture, then, the resultant product was washed with water and saturated saline, and the organic layer was dried over anhydrous sodium sulfate. The residue obtained by distilling off the solvent under reduced pressure was purified by silica gel column chromatography, whereby 0.31 g of a compound 6-6 was obtained as a glassy solid.

As a result of $^1$H-NMR measurement, the above-obtained compound was a mixture of an isomer A and an isomer B, and the ratio (A:B) thereof was 2:1.

$^1$H-NMR(CDCl$_3$) δ value: 8.10-7.90(8H+8H,m,A+B), 7.69-7.30(29H+28H,m,A+B), 6.76(1H,d,J=4.8 Hz,B), 6.56 (1H,dd,J=2.4 Hz,4.5 Hz,B), 6.52(1H,dd,J=2.1 Hz,8.4 Hz,B), 6.26(1H,dd,J=2.4 Hz,4.5 Hz,A), 6.17-6.06(2H+1H,m,A+B), 4.87-4.78(2H+2H,m,A+B), 4.49-4.34(1H+1H,m,A+B), 4.03(3H,s,B), 3.80(3H,s,A)

(7)

0.092 mL of 1 mol/L hydrochloric acid was added to a mixture of 0.23 g of the compound 6-6, 0.18 mL of a 37% formalin aqueous solution, and 10 mL of acetone, and the resultant product was stirred at room temperature for 24 hours. 50 mL of ethyl acetate and water were added to the reaction mixture, and the organic layer was washed with a sodium hydrogen carbonate aqueous solution and saturated saline. After the organic layer was dried over anhydrous sodium sulfate, the solvent was distilled off under reduced pressure, and the obtained residue was purified by silica gel column chromatography, whereby 0.20 g of a compound 6-7 was obtained as a glassy material.

$^1$H-NMR(CDCl$_3$) δ value: 9.73(1H,s), 8.14-7.90(8H,m), 7.58-7.30(28H,m), 6.46(1H,dd,J=2.4 Hz,8.1 Hz), 6.22(1H,dd,J=2.4 Hz,8.1 Hz), 5.86(1H,d,J=2.7 Hz), 4.83(1H,dd,J=5.1 Hz,11.1 Hz), 4.76-4.67(1H,m), 4.45(1H,dd,J=9.0 Hz,11.1 Hz), (8)

0.032 mL of a 15% sodium hydrogen sulfide aqueous solution was added to a solution of 0.067 g of the compound 6-7 in 5 mL of N,N-dimethylformamide at 1° C. to 2° C., and the resultant product was stirred for 20 minutes. 50 mL of ethyl acetate was added to the reaction mixture, and the organic layer was washed with water and saturated saline. The residue obtained by distilling off the solvent under reduced pressure was washed with toluene and methanol, whereby 0.010 g of a compound 6-8 was obtained as a white solid.

$^1$H-NMR(CDCl$_3$) δ value: 8.10-7.86(8H,m), 7.60-7.30(28H,m), 6.34(1H,t,J=9.9 Hz), 6.03(1H,t,J=10.2 Hz), 5.68(1H,dd,J=2.7 Hz,10.2 Hz), 5.54(1H,t,J=2.7 Hz), 4.68(1H,dd,J=4.5 Hz,12.0 Hz), 4.61(1H,dd,J=4.8 Hz,12.0 Hz), 4.20(1H,ddd,J=4.5 Hz,4.8 Hz,10.8 Hz), 2.81(1H,d,J=2.1 Hz)

Example 7

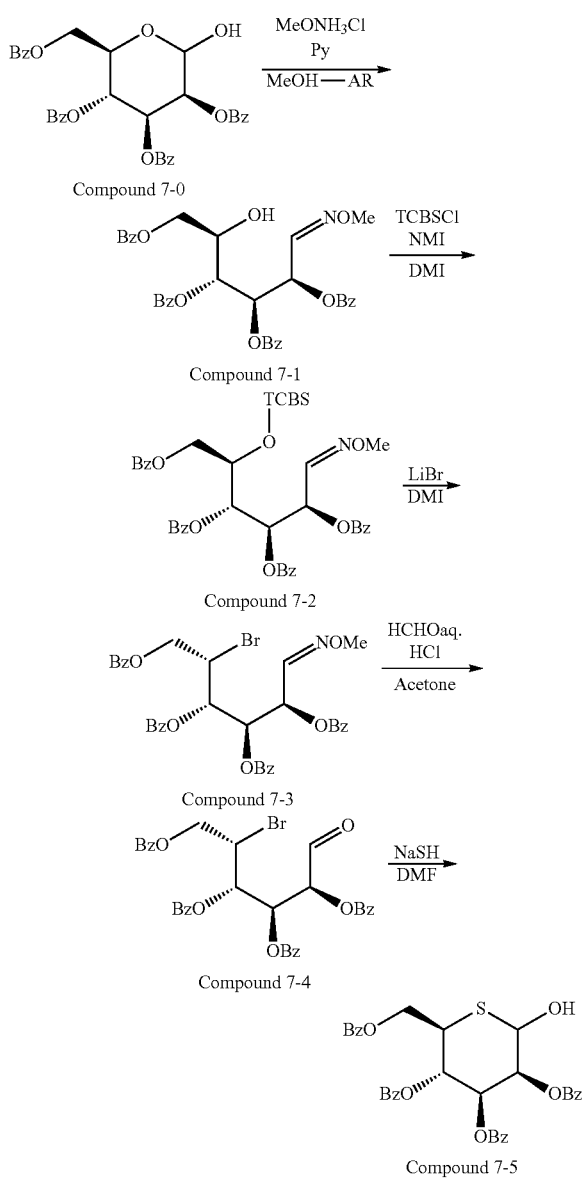

(1)

3.0 g of O-methylhydroxylamine hydrochloride was added to a solution of 10.6 g of a compound 7-0 in 50 mL of methanol, 10 mL of acetonitrile, and 7.2 mL of pyridine, and the resultant product was stirred at 50° C. for 3 hours. 100 mL of ethyl acetate and 100 mL of 1 mol/L hydrochloric acid were added to the reaction mixture, and the aqueous layer was removed. The organic layer was washed with 25% by mass saline and dried over anhydrous magnesium sulfate, and the solvent was distilled off under reduced pressure, whereby 11.07 g of a compound 7-1 was obtained. As a result of $^1$H-NMR measurement, the above-obtained compound was a mixture of an isomer A and an isomer B, and the ratio (A:B) thereof was 3:1.

$^1$H-NMR(CDCl$_3$) δ value: 8.14-7.95(m,8H+8H,A+B), 7.42-7.42(m,13H+13H,A+B), 6.94(d,1H,J=6.0 Hz,B), 6.52 (t,1H,J=6.0 Hz,B), 6.22-6.17(m,2H+1H,A+B), 5.93-5.76(m,2H+1H,A+B), 4.59-4.54(m,1H+1H,A+B), 4.37-4.31(m,1H+1H,A+B), 4.20-4.13(m,1H+1H,A+B), 3.84(S,1H,B), 3.67(d,1HJ=5.1 Hz,A), 3.58(S,1H,A), 3.51(d,1H,J=5.4 Hz,B)

(2)

3.48 mL of 1-methylimidazole was added dropwise to a solution of 11.07 g of the compound 7-1 and 7.41 g of 2,4,5-trichlorobenzenesulfonyl chloride in 110 mL of acetonitrile at 0° C. to 5° C., and the resultant product was stirred at room temperature for 6 hours. After allowing to stand at room temperature for 9 hours, 200 mL of ethyl acetate and 5 mL of concentrated hydrochloric acid were added to the reaction mixture, and the resultant product was washed with 150 mL of 10% by mass saline. After the white solid precipitated when washing was separated by filtration, the organic layer was washed four times with 150 mL of 10% by mass saline. The organic layer was dried over anhydrous magnesium sulfate, then, the residue obtained by distilling off the solvent under reduced pressure was purified by silica gel column chromatography (hexane/ethyl acetate=75/25), whereby 10.66 g of a compound 7-2 was obtained. As a result of $^1$H-NMR measurement, the above-obtained compound was a mixture of an isomer A and an isomer B, and the ratio (A:B) thereof was 3:1.

$^1$H-NMR(CDCl$_3$) δ value: 8.06-7.80(m,9H+9H,A+B), 7.62-7.23(m,14H+14H,A+B), 6.94(d,1H,J=6.0 Hz,B), 6.52 (t,1H,J=6.0 Hz,B), 6.15-5.92(m,2H+1H,A+B), 5.50-5.45(m,1H+1H,A+B), 4.86-4.78(m,1H+1H,A+B), 4.86-4.78(m,1H+1H,A+B), 3.85(s,1H,B), 3.68(s,1H,A)

(3)

2.12 g of lithium bromide was added to a solution of 10.60 g of the compound 7-2 in 80 mL of 1,3-dimethyl-2-imidazolidinone, and the resultant product was stirred at 50° C. for 5 hours. 200 mL of ethyl acetate, 180 mL of water, and 20 mL of a 25% by mass saline were added to the reaction mixture, and the resultant product was washed. The organic layer was washed with a 25% by mass saline, and dried over anhydrous magnesium sulfate. The solvent was distilled off under reduced pressure, and the obtained residue was purified by silica gel column chromatography (hexane/ethyl acetate=80/20), whereby 5.29 g of a compound 7-3 was obtained. As a result of $^1$H-NMR measurement, the above-obtained compound was a mixture of an isomer A and an isomer B, and the ratio (A:B) thereof was 3:1.

$^1$H-NMR(CDCl$_3$) δ value: 8.08-7.91(m,8H+8H,A+B), 7.62-7.29(m,13H+12H,A+B), 6.91(d,1H,J=6.0 Hz,B), 6.46-6.21(m,6H+6H,A+B), 4.82-4.74(m,2H+2H,A+B), 4.55-4.46(m,1H+1H,A+B), 3.87(s,1H,B), 3.69(s,1H,A), (4)

0.35 mL of 2 mol/L hydrochloric acid was added to a mixture of 1.9 g of the compound 7-3, 2.08 mL of a 37% formalin aqueous solution, and 17 mL of acetone, and the resultant product was stirred at 50° C. for 2.5 hours. 40 mL of ethyl acetate was added to the reaction mixture, and the organic layer was washed two times with a 25% by mass saline and dried over anhydrous magnesium sulfate. The solvent was distilled off under reduced pressure, and the obtained residue was purified by silica gel column chromatography (hexane/ethyl acetate=75/25), whereby 1.62 g of a compound 7-4 was obtained.

$^1$H-NMR(CDCl$_3$) δ value: 9.79(s,1H), 8.11-7.91(m,8H), 7.60-7.28(m,12H), 6.33-6.25(m, 2H), 5.70(dd,1H,J=0.6 Hz,3.3 Hz), 4.82-4.68(m,2H), 4.56-4.50(m,1H)

(5)

4.13 g of a 15% sodium hydrogen sulfide aqueous solution was added to a solution of 1.62 g of the compound 7-4 in 20 mL of N,N-dimethylformamide at 0° C. to 10° C., and the resultant product was stirred for 1 hour. 100 mL of ethyl acetate, 50 mL of water, and 50 mL of a 25% by mass saline were added to the reaction mixture, and the organic layer was washed. The organic layer was washed two times with a 7.5% by mass sodium hydrogen carbonate aqueous solution, washed once with a 25% by mass saline, and dried over anhydrous sodium sulfate. The solvent was distilled off under reduced pressure, and the obtained residue was purified by silica gel column chromatography (hexane/ethyl acetate=75/25), whereby 0.75 g of a compound 7-5 was obtained.

$^1$H-NMR(CDCl$_3$) δ value: 8.15-7.78(m,8H), 7.62-7.20 (m,12H), 6.29(t,1HJ=10.5 Hz), 6.02(dd,1H,J=3.0 Hz,10.5 Hz), 5.89(dd,1HJ=3.0 Hz,4.2 Hz), 5.29(t,1H,J=3.6 Hz), 4.67 (dd,1H,J=3.9 Hz,12.0 Hz), 4.57(dd,1H,J=4.8 Hz,12.0 Hz), 4.16(m,1H), 3.12(d,1HJ=3.3 Hz)

Example 8

Synthesis Route [IIc] of Scheme A

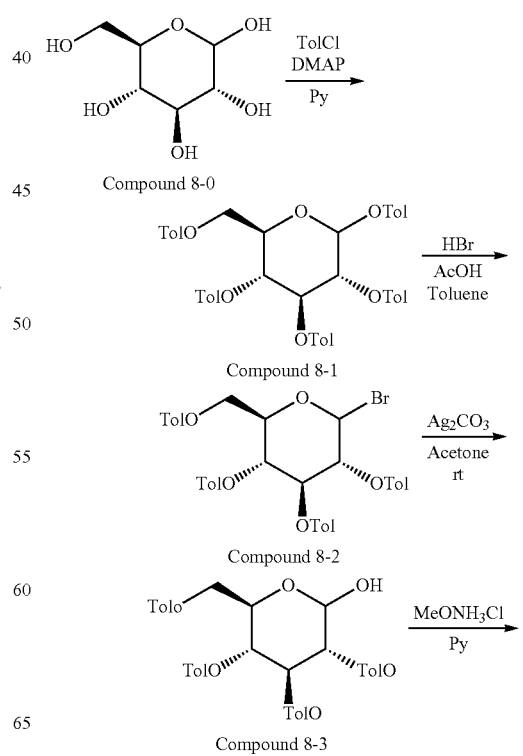

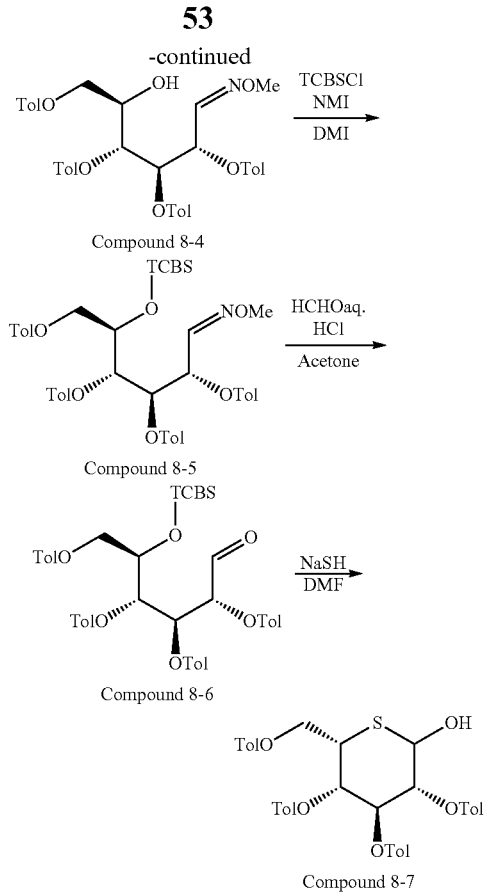

-continued

Compound 8-4

Compound 8-5

Compound 8-6

Compound 8-7

(1)

0.1 g of 4-dimethylaminopyridine was added to a solution of 15.0 g of a compound 8-0 in 200 mL of pyridine, then, 90.69 g of 4-methylbenzoyl chloride was added dropwise thereto at 0° C. to 10° C., and the resultant product was stirred at room temperature for 12 hours. After allowing to stand at room temperature for 9 hours, 400 mL of toluene was added to the reaction mixture, and the resultant product was mixed. After the organic layer was washed two times with 400 mL of water, the organic layer was washed once with 400 mL of 6 mol/L hydrochloric acid, and washed two times with 10% by mass saline. The organic layer was dried over anhydrous magnesium sulfate, then, the residue obtained by distilling off the solvent under reduced pressure was purified by silica gel column chromatography (hexane/ethyl acetate=75/25), whereby 60.0 g of a compound 8-1 was obtained.

$^1$H-NMR(CDCl$_3$) δ value: 8.07-7.73(m,10H), 7.39-7.09 (m,10H), 6.58(d,1H,J=1.8 Hz), 6.22(t,1H,J=10.2 Hz), 6.02 (dd,1H,J=3.3 Hz,6.3 Hz), 5.86(dd,1H,J=2.1 Hz,3.0 Hz), 4.66(dd,1H,J=2.4 Hz,12.3 Hz), 4.55-4.50(m,1H), 4.45(dd, 1H,J=3.9 Hz,12.0 Hz), 2.48(s,3H), 2.45(s,3H), 2.35(s,3H)

(2)

8 mL of a 30% hydrogen bromide/acetic acid solution was added to a solution of 13.8 g of the compound 8-1 in 60 mL of acetic acid, followed by stirring at room temperature for 3 hours and then at 40° C. for 2 hours, and 8 mL of a 30% hydrogen bromide/acetic acid solution was added thereto, followed by stirring at 50° C. for 1 hour. After 70 mL of water was added to the reaction mixture, 100 mL of toluene was added thereto, the aqueous layer was removed, the organic layer was washed with water, neutralized with a saturated sodium hydrogen carbonate aqueous solution, and washed with saturated saline, and the solvent was distilled off under reduced pressure, whereby 12.0 g of a compound 8-2 was obtained as a glassy material.

$^1$H-NMR(CDCl$_3$) δ value: 7.98(d,2H,J=8.1 Hz), 7.90(d, 2H,J=8.2 Hz), 7.87(d,2H,J=8.3 Hz), 7.73(d,2H,J=8.2 Hz), 7.26-7.15(m,6H), 7.07(d,2H,J=8.0 Hz), 6.57(d,1H,J=1.0 Hz), 6.25(dd,1H,J=3.0 Hz,10.1 Hz), 6.19(t,1H,J=10.2 Hz), 5.86(dd,1H,J=1.8 Hz,2.7 Hz), 4.72(dd,1H,J=2.3 Hz,12.4 Hz), 4.62(dt,1H,J=3.4 Hz,9.3 Hz), 4.46(dd,1H,J=3.9 Hz,12.4 Hz), 2.43(s,6H), 2.36(s,3H), 2.30(s,3H)

(3)

6.36 g of silver carbonate was added to a solution of 11.0 g of the compound 8-2 in 77 mL of acetone, and the resultant was stirred at room temperature for 1 hour. The silver carbonate was separated from the reaction mixture by filtration, and the solvent was distilled off under reduced pressure, whereby 10.24 g of a compound 8-3 was obtained as a glassy material.

As a result of $^1$H-NMR measurement, the above-obtained compound was a mixture of an isomer A and an isomer B, and the ratio (A:B) thereof was 0.55:0.45.

$^1$H-NMR(CDCl$_3$) δ value: 8.01-7.68(m,8H+8H,A+B), 7.23-7.05(m,8H+8H,A+B), 6.13(t,1H,J=10.1 Hz,B), 5.99(t, 1H,J=10.0 Hz,A), 5.96(dd,1H,J=3.2 Hz,10.1 Hz,B), 5.83(d, 1H,J=2.8 Hz,A), 5.69(dd,1H,J=2.0 Hz,3.1 Hz,B), 5.61(dd, 1H,J=3.1 Hz,10.1 Hz,A), 5.50(dd,1H,J=1.7 Hz,4.0 Hz,B), 5.27(d,1H,J=10.1 Hz,A), 4.75(dd,1H,J=2.6 Hz,6.0 Hz,B), 4.71(dd,1H,J=2.6 Hz,6.0 Hz,B), 4.63(dt,1H,J=3.2 Hz,9.9 Hz,B), 4.46(dd,1H,J=4.8 Hz,12.2 Hz,A), 4.40(dd,1H,J=4.0 Hz,12.2 Hz,B), 4.15(ddd,1H,J=2.7 Hz,4.7 Hz,9.9 Hz,A), 3.95-3.85(m,1H,A), 3.50(brs,1H,B), 2.42(s,6H+6H,A+B), 2.34(s,3H+3H,A+B), 2.29(s,3H+3H,A+B)

(4)

18 mL of pyridine and 2.34 g of O-methylhydroxylamine hydrochloride were added to 9.13 g of the compound 8-3, and the resultant product was stirred at 50° C. for 5 hours. After 45 mL of toluene was added to the reaction mixture, the organic layer was washed with water, 1 mol/L hydrochloric acid, and saturated saline, and dried over anhydrous sodium sulfate, and the residue obtained by distilling off the solvent under reduced pressure was purified by silica gel column chromatography, whereby 8.88 g of a compound 8-4 was obtained as a glassy material.

As a result of $^1$H-NMR measurement, the above-obtained compound was a mixture of an isomer A and an isomer B, and the ratio (A:B) thereof was 4:1.

$^1$H-NMR(CDCl$_3$) δ value: 8.05-7.82(m,8H+6H,A+B), 7.74 (d,2H,J=8.2 Hz,B), 7.49(d,1H,J=6.7 Hz,A), 7.32-7.10 (m,8H+6H,A+B), 7.04 (d,2H,J=8.0 Hz,B), 6.90(d,1H,J=6.1 Hz,B), 6.47(t,1H,J=10.1 Hz,B), 6.17-6.15(m,1H,B), 6.12 (dd,1H,J=1.9 Hz,6.8 Hz,A), 5.86(t,1H,J=6.9 Hz,A), 5.81(dd, 1H,J=1.9 Hz,9.1 Hz,A), 5.72(dd,1H,J=2.3 Hz,8.6 Hz,B), 4.51(dd,1H+1H,J=2.7 Hz,11.8 Hz,A+B), 4.37-4.22(m,1H+ 1H,A+B), 4.12-4.08(m,1H+1H,A+B), 3.83(s,1H,B), 3.69(d, 1H,J=5.1 Hz,A), 3.58(s,1H,A), 3.51(d,1H,J=5.4 Hz,B), 2.46-2.30(m,12H+12H,A+B)

(5)

0.8 mL of 1-methylimidazole was added dropwise to a solution of 3.41 g of the compound 8-4 and 1.68 g of 2,4,5-trichlorobenzenesulfonyl chloride in 34 mL of acetonitrile at 0° C. to 5° C., and the resultant product was stirred at room temperature for 3 hours. 68 mL of ethyl acetate was added to the reaction mixture, and the resultant product was washed with water and saturated saline. After the white solid precipitated when washing was separated by filtration, the organic layer was dried over anhydrous sodium sulfate, and the solvent was distilled off under reduced pressure, whereby 4.63 g of a compound 8-5 was obtained as a glassy solid.

As a result of ¹H-NMR measurement, the above-obtained compound was a mixture of an isomer A and an isomer B, and the ratio (A:B) thereof was 4:1.

¹H-NMR(CDCl₃) δ value: 7.95-7.70(m,8H+8H,A+B), 7.88 (s,1H+1H,A+B), 7.48(d,1H,J=6.7 Hz,A), 7.26 (s,1H+1H,A+B), 7.24-7.00(m,8H+8H,A+B), 6.87(d,2H,J=5.9 Hz,B), 6.47(t,1H,J=5.4 Hz,B), 6.21-6.07(m,1H,B), 6.08(dd,1H,J=3.1 Hz,5.7 Hz,A), 6.01(t,1H,J=3.5 Hz,A), 5.94(t,1H,J=3.6 Hz,B), 5.89(t,1H,J=6.2 Hz,A), 5.47-5.40(m,1H+1H,A+B), 4.80-4.65(m,2H+2H,A+B), 3.82(s,1H,B), 3.68(s,1H,A), 2.43-2.35(m,12H+12H,A+B)

(6)

0.25 mL of 1 mol/L hydrochloric acid was added to a mixture of 0.46 g of the compound 8-5, 0.40 mL of a 37% formalin aqueous solution, and 9.2 mL of acetone, and the resultant product was stirred at room temperature for 29 hours. 50 mL of ethyl acetate and water were added to the reaction mixture, and the organic layer was washed with a sodium hydrogen carbonate aqueous solution and saturated saline. After the organic layer was dried over anhydrous sodium sulfate, the solvent was distilled off under reduced pressure, whereby 0.42 g of a compound 8-6 was obtained as a glassy material.

¹H-NMR(CDCl₃) δ value: 9.67(s,1H), 7.95-7.70(m,8H), 7.91(s,1H), 7.30 (s,1H), 7.26-7.07(m,8H), 6.09(dd,1H,J=3.1 Hz,6.3 Hz), 6.02(dd,1H,J=3.1 Hz,4.5 Hz), 5.59(d,1H,J=6.2 Hz), 5.50-5.42(m,1H), 4.77(dd,1H,J=3.4 Hz,12.6 Hz), 4.65 (dd,1H,J=6.7 Hz,12.7 Hz), 2.42-2.35(m,12H)

(7)

0.09 mL of a 15% sodium hydrogen sulfide aqueous solution was added to a solution of 0.18 g of the compound 8-6 in 9 mL of N,N-dimethylformamide at 1° C. to 2° C., and the resultant product was stirred for 30 minutes. 50 mL of ethyl acetate was added to the reaction mixture, and the organic layer was washed with water, a sodium hydrogen carbonate aqueous solution, and saturated saline. After the organic layer was dried over anhydrous sodium sulfate, the solvent was distilled off under reduced pressure, and the obtained residue was purified by silica gel column chromatography, whereby 0.04 g of a compound 8-7 was obtained as a yellow oily material.

As a result of ¹H-NMR measurement, the above-obtained compound was a mixture of an isomer A and an isomer B, and the ratio (A:B) thereof was 7:1.

¹H-NMR(CDCl₃) δ value(isomer A): 8.13(d,2H,J=8.1 Hz), 7.84(d,2H,J=8.2 Hz), 7.83(d,2H,J=8.2 Hz), 7.56(d,2H,J=8.2 Hz), 7.24(d,2H,J=9.6 Hz), 7.15(d,2H,J=7.6 Hz), 7.13 (d,2H,J=7.9 Hz), 7.08(d,2H,J=8.1 Hz), 6.25(dd,1H,J=2.7 Hz,10.1 Hz), 6.10(dd,1H,J=4.9 Hz,10.1 Hz), 5.90(dd,1H,J=2.9 Hz,4.5 Hz), 5.34(t,1H,J=10.2 Hz), 5.17(brs,1H), 4.69-4.61(m,1H), 4.20-4.10(m,1H), 3.91-3.83(m,1H), 2.43(s,3H), 2.38(s,3H), 2.34(s,3H), 2.31(s,3H)

Example 9

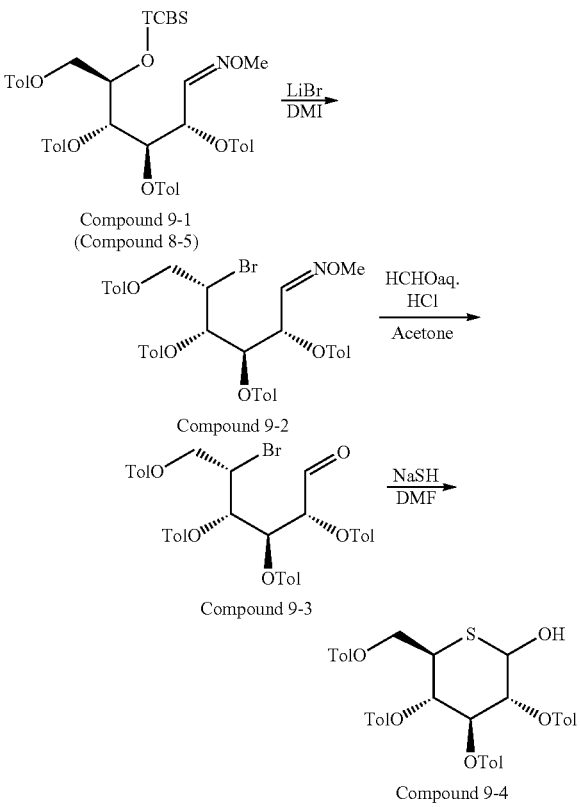

Compound 9-1 (Compound 8-5)

Compound 9-2

Compound 9-3

Compound 9-4

(1)

0.17 g of lithium bromide was added to a solution of 0.93 g of the compound 9-1 in 5.0 mL of 1,3-dimethyl-2-imidazolidinone, and the resultant product was stirred at 50° C. for 6 hours. 50 mL of ethyl acetate was added to the reaction mixture, then, the resultant product was washed with water and saturated saline, and the organic layer was dried over anhydrous sodium sulfate. The residue obtained by distilling off the solvent under reduced pressure was purified by silica gel column chromatography, whereby 0.85 g of a compound 9-2 was obtained as a glassy solid.

As a result of ¹H-NMR measurement, the above-obtained compound was a mixture of an isomer A and an isomer B, and the ratio (A:B) thereof was 3:1.

¹H-NMR(CDCl₃) δ value: 7.97-7.76(m,9H+9H,A+B), 7.53(d,1H,J=7.1 Hz,A), 7.26-7.07(m,9H+9H,A+B), 6.88 (d,2H,J=6.2 Hz,B), 6.40(dd,1H,J=3.0 Hz,6.2 Hz,B), 6.29 (dd,1H,J=3.0 Hz,7.6 Hz,B), 6.18(dd,1H,J=4.0 Hz,6.7 Hz,A), 5.98(dd,1H,J=2.8 Hz,6.7 Hz,A), 6.18(dd,1H,J=4.0 Hz,7.1 Hz,A), 5.90-5.86(m,1H,B), 4.78-4.69(m,2H+2H,A+B), 4.50-4.41(m,1H+1H,A+B), 3.85(s,1H,B), 3.69(s,1H,A), 2.42(s,3H+3H,A+B), 2.37(s,3H+3H,A+B), 2.36(s,6H+6H,A+B)

(2)

0.15 mL of 1 mol/L hydrochloric acid was added to a mixture of 0.22 g of the compound 9-2, 0.24 mL of a 37% formalin aqueous solution, and 4 mL of acetone, and the resultant product was allowed to react at room temperature for 15 hours and allowed to react at 50° C. for 2 hours. 30 mL of ethyl acetate and water were added to the reaction mixture, and the organic layer was washed with a sodium hydrogen carbonate aqueous solution and saturated saline. After the organic layer was dried over anhydrous sodium sulfate, the solvent was distilled off under reduced pressure, whereby 0.21 g of a compound 9-3 was obtained as a glassy material.

$^1$H-NMR(CDCl$_3$) δ value: 9.75(s,1H), 7.99(d,2H,J=8.2 Hz), 7.89(d,2H,J=8.3 Hz), 7.86(d,2H,J=8.2 Hz), 7.82(d,2H, J=8.2 Hz), 7.25(d,2H,J=7.3 Hz), 7.18(d,2H,J=7.9 Hz), 7.16 (d,2H,J=7.9 Hz), 7.05(d,2H,J=8.0 Hz), 6.25(dd,1H,J=3.2 Hz,7.1 Hz), 6.20(dd,1H,J=2.7 Hz,7.0 Hz), 5.64(d,1H,J=3.3 Hz), 4.76(dd,1H,J=5.5 Hz,11.2 Hz), 4.66(ddd,1H,J=2.8 Hz,5.7 Hz,7.5 Hz), 4.48(dd,1H,J=7.5 Hz,11.2 Hz), 2.43(s, 3H), 2.37(s,3H), 2.36(s,6H)

(3)

0.07 mL of a 15% sodium hydrogen sulfide aqueous solution was added to a solution of 0.11 g of the compound 9-3 in 5.5 mL of N,N-dimethylformamide at 1° C. to 2° C., and the resultant product was stirred for 45 minutes. 50 mL of ethyl acetate was added to the reaction mixture, and the organic layer was washed with water, a sodium hydrogen carbonate aqueous solution, and saturated saline. After the organic layer was dried over anhydrous sodium sulfate, the residue obtained by distilling off the solvent under reduced pressure was purified by silica gel column chromatography, whereby 0.07 g of a compound 9-4 was obtained as a yellow oily material.

As a result of $^1$H-NMR measurement, the above-obtained compound was a mixture of an isomer A and an isomer B, and the ratio (A:B) thereof was 7:1.

$^1$H-NMR(CDCl$_3$) δ value(isomer A): 8.01(d,2H,J=8.2 Hz), 7.94(d,2H,J=8.1 Hz), 7.79(d,2H,J=8.2 Hz), 7.69(d,2H, J=8.2 Hz), 7.21(d,2H,J=8.7 Hz), 7.18(d,2H,J=8.6 Hz), 7.08 (d,2H,J=8.1 Hz), 7.01(d,2H,J=8.1 Hz), 6.24(t,1H,J=10.4 Hz), 5.99(dd,1H,J=1.6 Hz,10.1 Hz), 5.86(t,1H,J=2.9 Hz), 5.26(t,1H,J=3.5 Hz), 4.65(dd,1H,J=3.8 Hz,11.9 Hz), 4.52 (dd,1H,J=4.9 Hz,11.9 Hz), 4.14-4.06(m,1H), 3.60(brs,1H), 2.43(s,3H), 2.41(s,3H), 2.30(s,3H), 2.25(s,3H)

Example 10

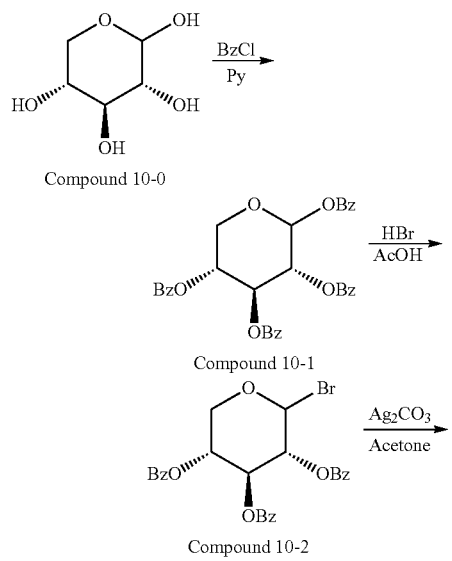

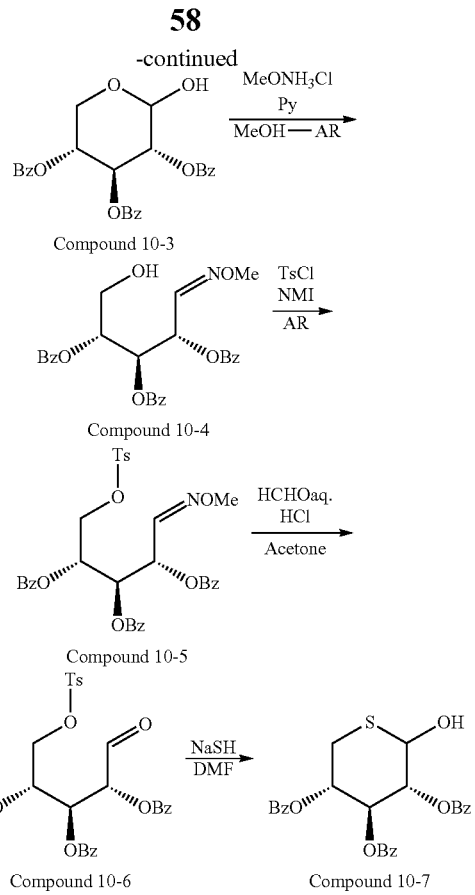

(1)

97.1 mL of benzoyl chloride was added to a solution of 25 g of a compound 10-0 in 100 mL of pyridine and 100 mL of tetrahydrofuran over a period of 45 minutes while maintaining the inner temperature at 15° C. to 35° C., and the resultant product was stirred at room temperature for 15 minutes and allowed to stand for 13 hours. After 100 mL of water, 40 mL of concentrated hydrochloric acid, and 150 mL of ethyl acetate were added to the reaction mixture, the aqueous layer was removed, then, the organic layer was neutralized with a saturated sodium hydrogen carbonate aqueous solution, washed with saturated saline, and dried over anhydrous sodium sulfate, and the solvent was distilled off under reduced pressure. 200 mL of methanol was added to the obtained oily material, followed by violently stirring, and the precipitated solid was collected by filtration, washed with methanol and hexane, and dried, whereby 65.4 g of a compound 10-1 was obtained.

As a result of $^1$H-NMR measurement, the above-obtained compound was a mixture of an isomer A and an isomer B, and the ratio (A:B) thereof was 2:1.

$^1$H-NMR(CDCl$_3$) δ value: 8.20-7.88(8H+8H,m,A+B), 7.77-7.29(12H+12H,m,A+B), 6.76(d,1H,J=3.6 Hz,B), 6.36 (d,1H,J=4.5 Hz,A), 6.28(t,1H,J=9.8 Hz,B), 5.83(t,1H,J=6.0 Hz,A), 5.66-5.60(1H+1H,m,A+B), 5.54(dt,1H,J=5.7 Hz,10.5 Hz,B), 5.40(dt,1H,J=3.9 Hz,5.7 Hz,B), 4.57(dd,1H, J=3.6 Hz,12.6 Hz,A), 4.30(dd,1H,J=5.7 Hz,11.1 Hz,B), 4.08-3.98(1H+1H,m,A+B)

(2)

4 mL of a 30% hydrogen bromide/acetic acid solution was added to a solution of 5.67 g of the compound 10-1 in 10 mL of toluene and 50 mL of acetic acid, and the resultant product was stirred for 3 hours. After 20 mL of water, 20 mL of toluene, and 10 mL of ethyl acetate were added to the reaction mixture, the aqueous layer was removed, then, the organic layer was neutralized with a saturated sodium hydrogen carbonate aqueous solution and washed with saturated saline, and the solvent was distilled off under reduced pressure, whereby 4.85 g of a compound 10-2 was obtained as a white solid.

$^1$H-NMR(CDCl$_3$) δ value: 8.25-7.90(8H,m), 7.67-7.29 (12H,m), 6.82(d,1H,J=4.2 Hz), 6.24(t,1H,J=9.9 Hz), 5.49 (ddd,1H,J=6.0 Hz,9.9 Hz,10.8 Hz), 5.28(dd,1H,J=4.2 Hz,9.9 Hz), 5.35(dd,1H,J=5.8 Hz,11.3 Hz), 4.13(t,1H, J=11.1 Hz), (3)

0.82 g of sodium hydrogen carbonate and 18.2 g of water were added to a solution of 4.68 g of the compound 10-2 in 10 mL of tetrahydrofuran and 10 mL of acetonitrile, and the resultant product was stirred at 40° C. for 30 minutes. After 50 mL of water and 50 mL of toluene were added to the reaction mixture, the aqueous layer was removed, then, the organic layer was washed with water and saturated saline and dried over anhydrous sodium sulfate, and the solvent was distilled off under reduced pressure, whereby 3.05 g of a compound 10-3 was obtained as a white solid.

As a result of $^1$H-NMR measurement, the above-obtained compound was a mixture of an isomer A and an isomer B, and the ratio (A:B) thereof was 1:0.3.

$^1$H-NMR(CDCl$_3$) δ value: 8.20-7.92(6H+6H,m,A+B), 7.57-7.30(9H+9H,m,A+B), 6.20(t,1H,J=9.6 Hz,A), 5.92 (t,1H,J=8.5 Hz,B), 5.68(t,1H,J=3.8 Hz,A), 5.46-5.36(1H+ 1H,m,A+B), 5.34-5.26(1H+1H,m,A+B), 4.99(dd,1H,J=7.2 Hz,8.1 Hz,B), 4.46(dd,1H,J=5.4 Hz,11.7 Hz,B), 4.13(d,2H, J=3.9 Hz,A), 3.77(d,1H,J=8.4 Hz,B), 3.65(dd,1H,J=9.3 Hz,11.7 Hz,B), 3.02(d,1H,J=8.4 Hz,B), (4)

2.56 mL of pyridine and 1.06 g of O-methylhydroxylamine hydrochloride were added to a solution of 2.94 g of the compound 10-3 in 40 mL of acetonitrile, and the resultant product was stirred at 50° C. for 1 hour. After 40 mL of toluene was added to the reaction mixture, the organic layer was washed with 1 mol/L hydrochloric acid, a saturated sodium hydrogen carbonate aqueous solution, water, and saturated saline in this order, and dried over anhydrous sodium sulfate, and the solvent was distilled off under reduced pressure, whereby 3.26 g of a compound 10-4 was obtained. As a result of $^1$H-NMR measurement, the above-obtained compound was a mixture of an isomer A and an isomer B, and the ratio (A:B) thereof was 4:1.

$^1$H-NMR(CDCl$_3$) δ value: 8.20-7.92(6H+6H,m,A+B), 7.60-7.34(10H+9H,m,A+B), 6.74(d,1H,J=6.0 Hz,B), 6.61(t, 1H,J=9.6 Hz,B), 6.14(dd,1H,J=6.0 Hz,7.2 Hz,A), 6.09-6.03 (1H,m, B), 6.05(dd,1H,J=3.3 Hz, 6.9 Hz,A), 5.59(dt,1H, J=3.3 Hz, 6.3 Hz,A), 5.47(dt,1H,J=3.9 Hz, 5.7 Hz,B), 4.00-3.79(2H+2H,m,A+B), 3.78(s,3H,A), 3.76(s,3H,B), 2.60(dd, 1H,J=5.7 Hz, 8.1 Hz,A), 2.52(dd,1H,J=6.0 Hz, 7.8 Hz,B)

(5)

0.30 mL of 1-methylimidazole was added dropwise to a solution of 0.94 g of the compound 10-4 and 0.40 g of p-toluenesulfonyl chloride in 20 mL of acetonitrile at 6° C. to 8° C., and the resultant product was stirred at room temperature for 3 hours. After 30 mL of ethyl acetate was added to the reaction mixture, the organic layer was washed with water and saturated saline in this order and dried over anhydrous sodium sulfate, and the solvent was distilled off under reduced pressure, whereby 1.25 g of a compound 10-5 was obtained.

As a result of $^1$H-NMR measurement, the above-obtained compound was a mixture of an isomer A and an isomer B, and the ratio (A:B) thereof was 0.7:0.3.

$^1$H-NMR(CDCl$_3$) δ value: 8.20-7.92(6H+6H,m,A+B), 7.70-7.66(2H+2H,m,A+B), 7.60-7.51(3H+3H,m,A+B), 7.46-7.36(7H+6H,m,A+B), 7.16-7.10(2H+2H,m,A+B), 6.65(1H,d, J=5.4 Hz,B), 6.41(1H,t, J=5.4 Hz,B), 6.05(1H,t, J=5.4 Hz,B), 6.00-5.92(2H,m,A), 5.71(1H,dd, J=5.4 Hz, 9.3 Hz,A), 5.60(1H,q, J=5.1 Hz,B), 4.45-4.26(2H+2H,m,A+B), 3.77(3H, s,B), 3.76(3H,s,A), 2.29(3H+3H,s,A+B)

(6)

0.39 mL of 1 mol/L hydrochloric acid was added to a mixture of 1.26 g of the compound 10-5, 1.55 mL of a 36% formalin aqueous solution, and 20 mL of acetone, followed by stirring at 50° C. for 0.5 hours, and 0.50 mL of 1 mol/L hydrochloric acid was added thereto, followed by stirring at 50° C. for 2 hours. After 1.55 mL of a 36% formalin aqueous solution was added thereto, followed by stirring for 1 hour, the solvent was distilled off under reduced pressure, ethyl acetate and water were added thereto, the organic layer was washed with water and a saturated sodium chloride aqueous solution, dried over anhydrous sodium sulfate, and the solvent was distilled off under reduced pressure. The obtained residue was purified by silica gel column chromatography (hexane/ethyl acetate=80/20 to 50/50), whereby 0.78 g of a compound 10-6 was obtained as a foamy material.

$^1$H-NMR(CDCl$_3$) δ value: 9.61(1H,s), 8.07-7.84(6H,m), 7.69(2H,d,J=8.4 Hz), 7.65-7.50(3H,m), 7.59-7.34(6H,m), 7.14(2H,d,J=8.1 Hz), 6.07(1H, dd,J=3.6 Hz, 5.4 Hz), 5.79 (1H, dd,J=4.8 Hz, 10.2 Hz), 5.64(1H,d,J=3.6 Hz), 4.40(2H, dt,J=4.8 Hz, 11.7 Hz), 2.30(3H,s)

(7)

0.32 g of a 15% sodium hydrogen sulfide aqueous solution was added to a solution of 0.36 g of the compound 10-6 in 3.5 mL of N,N-dimethylformamide at 1° C. to 6° C., and the resultant product was stirred for 20 minutes. 20 mL of ethyl acetate and 10 mL of water were added to the reaction mixture, and the aqueous layer was removed. The organic layer was washed with water and a saturated sodium chloride aqueous solution and dried over anhydrous sodium sulfate, and the solvent was distilled off under reduced pressure. The obtained residue was purified by silica gel column chromatography (hexane/ethyl acetate=75/25 to 54/46), whereby 0.20 g of a compound 10-7 was obtained as a white solid.

$^1$H-NMR(CDCl$_3$) δ value: 7.98-7.84(6H,m), 7.54-7.46 (3H,m), 7.44-7.24(6H,m), 6.22(1H,t,J=9.9 Hz), 5.62-5.50 (2H,m), 5.39(1H,t,J=2.3 Hz), 3.35(1H,dd,J=11.4 Hz, 12.9 Hz), 3.02(1H,ddd,J=0.9 Hz, 4.5 Hz, 12.9 Hz), 2.43(1H, dd,J=1.0 Hz, 2.5 Hz)

Moreover, in the synthesis reaction using a benzoyl group in Example 10, more stable synthesis was possible since a protecting group was less likely to be leaved, compared with the reaction using an acetyl group.

Example 11

SXyL(Ac)

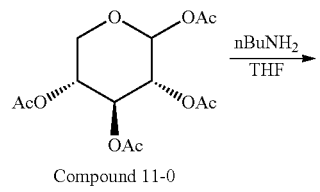

Compound 11-0

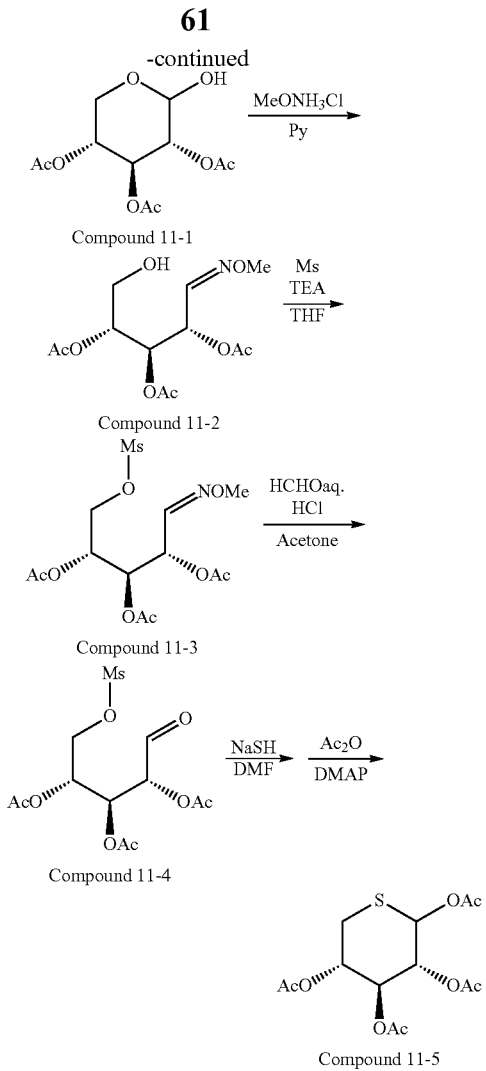

Compound 11-1

Compound 11-2

Compound 11-3

Compound 11-4

Compound 11-5

(1)
0.47 mL of n-butylamine was added to a solution of 1.0 g of a compound 11-0 in 6 mL of tetrahydrofuran, and the resultant product was stirred at room temperature for 1 hour and allowed to stand for 12 hours. The obtained compound 11-1 was used in the following step without purification.

(2)
1.21 mL of pyridine and 0.50 g of O-methylhydroxylamine hydrochloride were added to a solution of the reaction mixture including the compound 11-1, and the resultant product was stirred at 50° C. for 1.5 hours. After 50 mL of ethyl acetate was added to the reaction mixture, the organic layer was washed with 1 mol/L hydrochloric acid, water, and saturated saline in this order, then, the solvent was distilled off under reduced pressure, and the obtained residue was purified by silica gel column chromatography, whereby 0.60 g of a compound 11-2 was obtained.

As a result of $^1$H-NMR measurement, the above-obtained compound was a mixture of an isomer A and an isomer B, and the ratio (A:B) thereof was 3.7:1.

$^1$H-NMR(CDCl$_3$) δ value: 7.25(d,1H,J=5.4 Hz,A), 6.53 (d,1H,J=5.7 Hz,B), 6.08(t,1H,J=5.7 Hz,B), 5.62(dd,1H, J=6.3 Hz, 7.2 Hz,A), 5.56(dd,1H,J=4.8 Hz, 5.7 Hz,B), 5.49(dd,1H,J=3.3 Hz, 7.2 Hz,A), 5.09(dt,1H,J=3.6 Hz, 6.3 Hz,A), 5.02(dd,1H,J=5.4 Hz, 10.2 Hz,B), 3.90(3H,s,B), 3.85 (3H,s,A), 3.74-3.53(2H+2H,m,A+B), 2.32(dd,1H,J=5.4 Hz, 7.8 Hz,A), 2.27-2.20(1H,m,B), 2.15(3H,s,A), 2.12(3H+6H, s,A+B), 2.10(3H+3H,s,A+B)

(3)
0.53 mL of triethylamine was added to a solution of 0.60 g of the compound 11-2 in 4 mL of tetrahydrofuran, then, 0.16 mL of methanesulfonyl chloride was added thereto at 0° C. to 10° C., and the resultant product was stirred at 5° C. or lower for 30 minutes. Ethyl acetate and water were added to the reaction mixture, and then, the aqueous layer was removed. The organic layer was washed with water and a saturated sodium chloride aqueous solution, and the solvent was distilled off under reduced pressure. The obtained compound 11-3 was used in the following step without purification.

As a result of $^1$H-NMR measurement, the above-obtained compound was a mixture of an isomer A and an isomer B, and the ratio (A:B) thereof was 4:1.

$^1$H-NMR(CDCl$_3$) δ value: 7.26(1H,d, J=5.7 Hz,A), 6.53 (1H,d, J=5.7 Hz,B), 6.03(1H,dd,J=4.8 Hz, 5.4 Hz,B), 5.57 (1H,dd, J=6.0 Hz, 6.9 Hz,A), 5.60-5.55(1H,m,B), 5.45(1H, dd, J=3.9 Hz, 6.9 Hz,A), 5.33(1H,ddd,J=3.9 Hz,4.2 Hz,4.8 Hz,A), 5.25(1H,dt,J=4.5 Hz,5.7 Hz,B), 4.40-4.22(2H+2H, m,A+B), 3.92(3H,s,B), 3.86(3H,s,A), 3.05(3H,s,B), 3.04 (3H,s,A), 2.15(3H,s,B), 2.13(6H,s,A), 2.11(6H,s,B), 2.10 (3H,s,A)

(4)
After 0.20 mL of 1 mol/L hydrochloric acid was added to a mixture of the obtained compound 11-3, 1.59 mL of a 36% formalin aqueous solution, 20 mL of acetone, followed by stirring at 50° C. for 1 hour, ethyl acetate was added thereto, then, the organic layer was washed with water and a saturated sodium chloride aqueous solution and dried over anhydrous sodium sulfate, and the solvent was distilled off under reduced pressure, whereby 0.47 g of a compound 11-4 was obtained.

$^1$H-NMR(CDCl$_3$) δ value: 9.52(1H,s), 5.59(1H,t,J=4.5 Hz), 5.39(1H,q,J=5.1 Hz), 5.32(1H,d,J=4.5 Hz), 4.40(1H, dd,J=4.8 Hz, 11.1 Hz), 4.28(1H, dd,J=4.8 Hz, 11.1 Hz), 3.06(3H,s), 2.23(3H,s), 2.16(3H,s), 2.09(3H,s)

(5)
0.11 g of anhydrous sodium hydrogen sulfide was added to a solution of 0.47 g of the compound 11-4 in 5 mL of N,N-dimethylformamide at 0° C. to 10° C., and the resultant product was stirred for 2.5 hours. 1.22 mL of acetic anhydride and 5 mg of N,N-dimethylaminopyridine were added to the reaction liquid, followed by stirring for 0.5 hours, then, ethyl acetate and water were added thereto, and the aqueous layer was removed. The organic layer was washed with water and a saturated sodium chloride aqueous solution and dried over anhydrous sodium sulfate, and the solvent was distilled off under reduced pressure. The obtained residue was purified by silica gel column chromatography, whereby 0.15 g of a compound 11-5 was obtained.

$^1$H-NMR(CDCl$_3$) δ value: 6.09(1H, dd,J=0.9 Hz,3.0 Hz), 5.44(1H,t,J=10.1 Hz), 5.21(1H, dd,J=3.0 Hz,10.2 Hz), 5.12 (1H, ddd,J=4.5 Hz,9.9 Hz,11.4 Hz), 3.01(1H, dd,J=9.9 Hz,13.2 Hz), 2.79(1H,ddd,J=1.2 Hz,4.5 Hz,13.2 Hz),2.18 (3H,s),2.05(3H,s),2.04(3H,s),2.00(3H,s)

Example 12

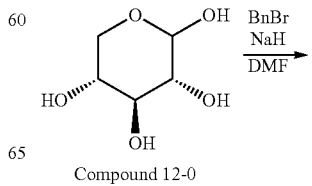

Compound 12-0

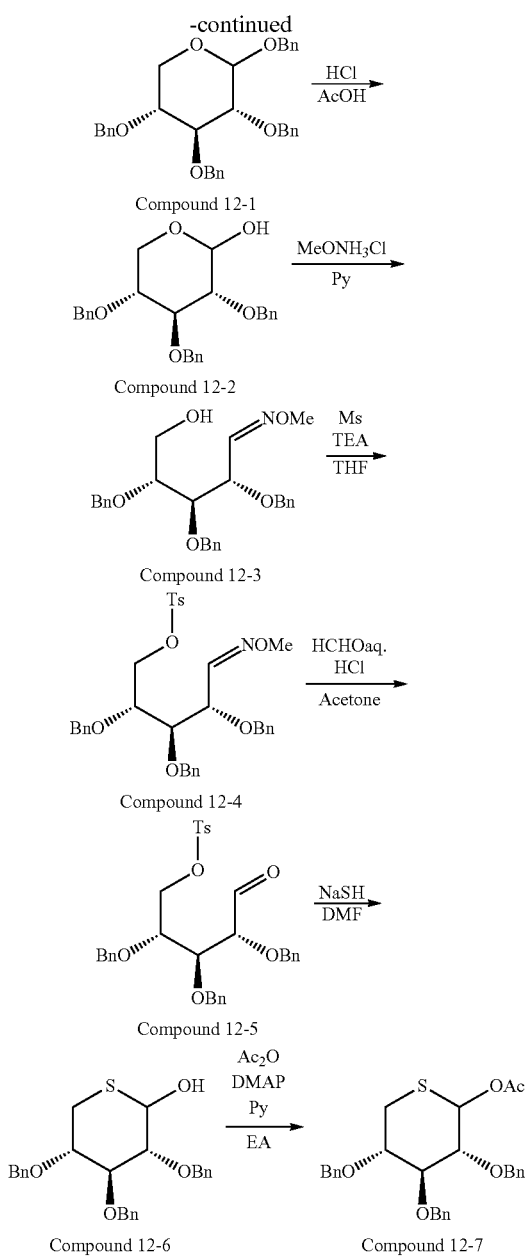

Compound 12-1

Compound 12-2

Compound 12-3

Compound 12-4

Compound 12-5

Compound 12-6

Compound 12-7

(1)
A compound 12-1 can be synthesized by the method described in Eur. J. Org. Chem. 2013, 1258-83.

(2)
A compound 12-2 can be synthesized by the method described in Eur. J. Org. Chem. 2013, 1258-83.

(3)
0.56 g of O-methylhydroxylamine hydrochloride was added to a solution of 1.65 g of the compound 12-2 in 5 mL of pyridine, and the resultant product was stirred at 50° C. for 1 hour. 50 mL of ethyl acetate and 20 mL of water were added to the reaction mixture, and the aqueous layer was removed. The organic layer was washed with 2 mol/L hydrochloric acid, water, and saturated saline in this order, and the solvent was distilled off under reduced pressure, whereby 1.3 g of a compound 13-3 was obtained. The obtained compound 12-3 was used in the following step without purification.

(4)
0.83 g of 4-methylbenzenesulfonyl chloride was added to a solution of 1.3 g of the compound 12-3 in 13 mL of acetonitrile at 25° C., then, 0.59 mL of N-methylimidazole was added dropwise hereto at 0° C. to 10° C., and the resultant product was stirred at 25° C. for 2 hours. 50 mL of ethyl acetate and 50 mL of 1 N hydrochloric acid were added to the reaction mixture, and the aqueous layer was removed. The organic layer was washed sequentially with a sodium hydrogen carbonate aqueous solution and a saturated sodium chloride aqueous solution and dried over anhydrous sodium sulfate, then, the solvent was distilled off under reduced pressure, and the resultant product was purified by silica gel column chromatography (eluent: ethyl acetate/hexane=¼→⅓), whereby 1.45 g of a compound 12-4 was obtained as a colorless oily material. As a result of $^1$H-NMR measurement, the above-obtained compound was an oxime isomer mixture of about 85:15.

$^1$H-NMR(CDCl$_3$) δ value: 2.40(3H,s), 3.62(0.85H,t,J=4.8 Hz), 3.81(0.45H,s), 3.85(2.55H,s), 3.86-3.88(0.15H,m), 4.02-4.37(5H,m), 4.47-4.59(4.85H,m), 4.84(0.15H,dd, J=4.3,7.3 Hz), 6.80(0.15H,d,J=4.3 Hz), 7.16-7.33(17.85H, m), 7.68(2H,d,J=8.3 Hz)

(5)
1.8 mL of a 30% formalin aqueous solution and 0.065 mL of 2N hydrochloric acid were added to a solution of 0.18 g of the compound 12-4 in 3 mL of acetone, and the resultant was stirred at 25° C. for 9 hours and stirred at 30° C. for 4 hours. 30 mL of ethyl acetate and 30 mL of a sodium hydrogen carbonate aqueous solution were added thereto, and the aqueous layer was removed. After the organic layer was washed sequentially with a sodium hydrogen carbonate aqueous solution, water, and a saturated sodium chloride aqueous solution, and dried over anhydrous sodium sulfate, the solvent was distilled off under reduced pressure. The obtained residue was purified by column chromatography (eluent: ethyl acetate/hexane=⅓→½), whereby 0.17 g of a compound 12-5 was obtained.

$^1$H-NMR(CDCl$_3$) δ value: 2.42(3H,s), 3.85-3.92(3H,m), 4.02(1H,dd,J=6.3,10.3), 4.18(1H,dd,J=4.7,9.9), 4.46-4.50 (5H,m), 4.73(1H,d,J=11.7 Hz), 7.29-7.38(17H,m), 7.68(2H, d,J=8.3 Hz), 9.61(1H,s)

(6)
0.14 mL of a 15% sodium hydrogen sulfide aqueous solution was added dropwise to a solution of 0.23 g of the compound 12-5 in 4.3 mL of N,N-dimethylformamide at 10° C. or lower, and the resultant product was stirred at 25° C. for 1.5 hours. 30 mL of ethyl acetate and 30 mL of a saturated sodium chloride aqueous solution were added to the reaction mixture, and then, the aqueous layer was removed. After the organic layer was washed sequentially three times with a sodium hydrogen carbonate aqueous solution and once with a saturated sodium chloride aqueous solution, the resultant product was dried over anhydrous sodium sulfate. The solvent was distilled off under reduced pressure, and the obtained residue was purified by column chromatography (eluent: ethyl acetate/hexane=1/3), whereby 40 mg of a compound 12-6 was obtained. As a result of $^1$H-NMR measurement, the above-obtained compound was a substantially single anomer.

$^1$H-NMR(CDCl$_3$) δ value: substantially single anomer
2.57(1H,dd,J=3.9,13.7 Hz),2.83(1H,brs),2.97(1H,dd, J=11.1,13.7 Hz),3.66-3.83(3H,m),4.63-4.73(4H,m),4.81-4.90(3H,m),7.25-7.36(15H,m)

(7)
After 13 mg of N,N-dimethyl-4-aminopyridine was added to a solution of 40 mg of the compound 12-6 in 10 mL of ethyl acetate, 0.2 mL of pyridine and 0.25 mL of acetic anhydride were added thereto at 10° C. or lower, and the resultant product was stirred at room temperature for 1 hour and allowed to stand overnight. 10 mL of ethyl acetate and 20 mL of 0.5 N hydrochloric acid were added to the reaction mixture, and the aqueous layer was removed. After the organic layer was washed sequentially four times with a sodium hydrogen carbonate aqueous solution and once with a saturated sodium chloride aqueous solution, and dried over anhydrous sodium sulfate, the solvent was distilled off under reduced pressure. The obtained residue was purified by column chromatography (eluent: ethyl acetate/hexane=1/3), whereby 28 mg of a compound 12-7 was obtained as a colorless oily material. As a result of $^1$H-NMR measurement, the above-obtained compound was a substantially single anomer.

$^1$H-NMR(CDCl$_3$) δ value: substantially single anomer
2.15(3H,s),2.63-2.68(1H,m),2.85-2.96(1H,m),3.67-3.82 (3H,m),4.58-4.77(4H,m),4.85(2H,s),6.09(1H,d,J=0.9 Hz), 7.27-7.35(15H,m)

Example 13

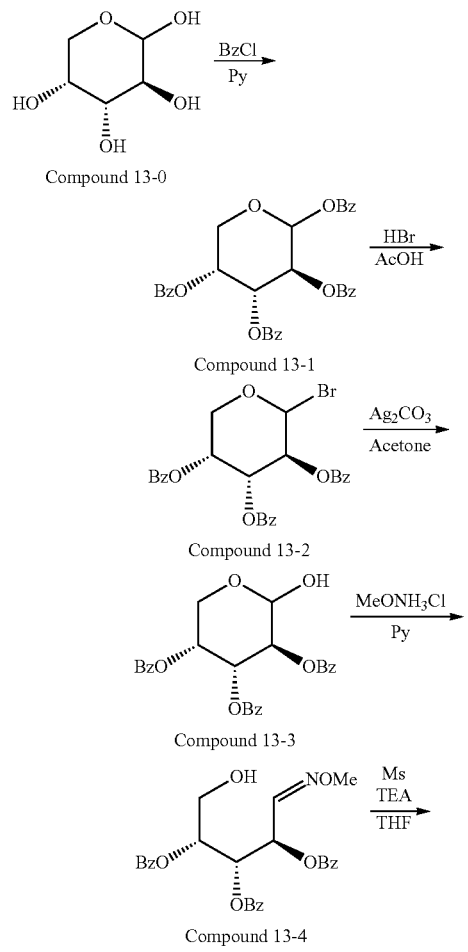

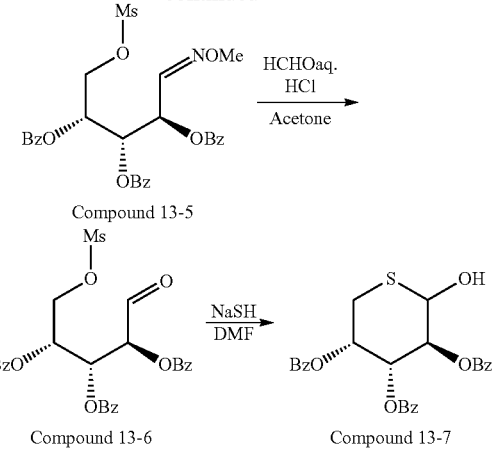

(1) to (3)

It is possible to synthesize compounds 13-1, 13-2, and 13-3 by the method described in Bioorganic and Medicinal Chemistry, 2006, vol. 14, #19 p. 6713-6725.

(4)

0.22 g of O-methylhydroxylamine hydrochloride was added to a solution of 0.6 g of the compound 13-3 in 6 mL of methanol, 1.5 mL of acetonitrile, and 0.52 mL of pyridine, and the resultant product was stirred at 50° C. for 1 hour. Ethyl acetate and 10 mL of 1 mol/L hydrochloric acid were added to the reaction mixture, and the aqueous layer was removed. The organic layer was washed with 1 mol/L hydrochloric acid, water, and saturated saline in this order, and dried over anhydrous sodium sulfate, then, the solvent was distilled off under reduced pressure, and the obtained residue was purified by silica gel column chromatography, whereby 0.52 g of a compound 13-4 was obtained.

As a result of $^1$H-NMR measurement, the above-obtained compound was a mixture of an isomer A and an isomer B, and the ratio (A:B) thereof was 3:1.

$^1$H-NMR(CDCl$_3$) δ value: 8.12-7.97(6H+6H,m,A+B), 7.66-7.38(10H+9H,m,A+B), 6.74(1H,d, J=5.1 Hz,B), 6.45 (1H,dd,J=3.3 Hz, 5.1 Hz,B), 6.15(1H,dd,J=3.3 Hz, 8.1 Hz,B), 6.09(dd,1H,J=4.2 Hz, 5.7 Hz,A), 6.02(dd,1H,J=4.2 Hz, 7.5 Hz,A), 5.54-5.45(1H+1H,m,A+B), 4.15-3.80(2H+ 2H,m,A+B), 3.98(3H,s,B), 3.75(3H,s,A), 2.62-2.54(1H+1H, m,A+B)

(5)

0.28 mL of triethylamine was added to a solution of 0.50 g of the compound 13-4 in 2 mL of tetrahydrofuran, then, 0.085 mL of methanesulfonyl chloride was added thereto at 0° C. to 10° C., and the resultant product was stirred at 5° C. or lower for 20 minutes. Ethyl acetate, n-hexane, and water were added to the reaction mixture, and the aqueous layer was removed. The solvent of the organic layer was distilled off under reduced pressure, and the obtained compound 13-5 was used in the following step without purification.

As a result of $^1$H-NMR measurement, the above-obtained compound was a mixture of an isomer A and an isomer B, and the ratio (A:B) thereof was 3:1.

$^1$H-NMR(CDCl$_3$) δ value: 8.08-7.94(6H+6H,m,A+B), 7.64-7.52(3H+3H,m,A+B), 7.50-7.36(7H+6H,m,A+B), 6.75(1H,d, J=5.7 Hz,B), 6.44(1H,dd,J=4.5 Hz, 5.4 Hz,B), 6.13(1H,dd,J=4.2 Hz, 6.9 Hz,B), 6.08-6.00(2H,m,A), 5.81-5.70(1H+1H,m,A+B), 4.69(dd,1H,J=2.7 Hz,11.7 Hz,B), 4.67(dd,1H,J=3.0 Hz,11.4 Hz,A), 4.55(dd,1H,J=5.7 Hz,11.7

Hz,B), 4.54(dd,1H,J=5.1 Hz,11.7 Hz,A),3.98(3H,s,B), 3.77 (3H,s,A), 3.00(3H,s,B), 2.98(3H,s,A)

(6)

After 0.10 mL of 1 mol/L hydrochloric acid was added to a mixture of the obtained compound 13-5, 0.79 mL of a 36% formalin aqueous solution, 10 mL of acetone, followed by stirring at 50° C. for 2 hour, 40 mL of ethyl acetate was added thereto, then, the organic layer was washed with water and a saturated sodium chloride aqueous solution and dried over anhydrous sodium sulfate, and the solvent was distilled off under reduced pressure, whereby 0.53 g of a compound 13-6 was obtained.

$^1$H-NMR(CDCl$_3$) δ value: 9.68(1H,s), 8.09-7.97(6H,m), 7.67-7.55(3H,m), 7.53-7.34(6H,m), 6.17(1H, dd,J=2.4 Hz, 8.1 Hz), 5.83(1H, ddd,J=2.7 Hz, 4.2 Hz,7.2 Hz), 5.72(1H, d,J=2.4 Hz), 4.69(1H, dd,J=2.7 Hz,11.7 Hz), 4.56(1H, dd,J=4.2 Hz, 11.7 Hz), 3.00(3H,s)

(7)

0.056 g of anhydrous sodium hydrogen sulfide was added to a solution of 0.53 g of the compound 13-6 in 5 mL of N,N-dimethylformamide at 0° C. to 10° C., followed by stirring for 40 minutes, then, ethyl acetate and water were added thereto, and the aqueous layer was removed. The organic layer was washed with water and a saturated sodium chloride aqueous solution and dried over anhydrous sodium sulfate, and the solvent was distilled off under reduced pressure. The obtained residue was purified by silica gel column chromatography, whereby 0.23 g of a compound 13-7 was obtained.

$^1$H-NMR(CDCl$_3$) δ value: 8.17-7.82(6H,m), 7.65-7.23 (9H,m), 6.22(1H,t,J=9.9 Hz), 6.03-6.00(2H,m), 5.96-5.91 (1H,m), 5.44(1H,brs), 3.62(1H,dd,J=1.5 Hz,14.7 Hz), 3.01 (1H, ddd,J=1.8 Hz,4.5 Hz,14.7 Hz), 2.43(1H,brs)

Example 14

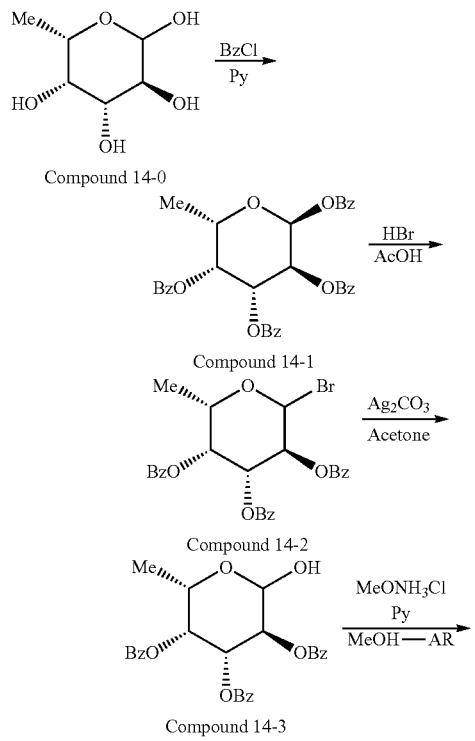

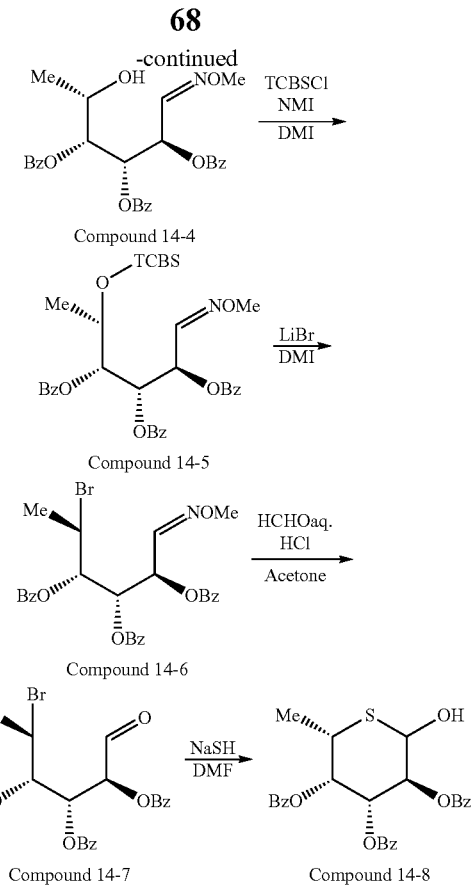

(1)

0.07 g of 4-dimethylaminopyridine was added to a solution of 9.16 g of a compound 14-0 in 90 mL of pyridine, then, 39.22 g of benzoyl chloride was added dropwise thereto at 0° C. to 10° C., and the resultant product was stirred at room temperature for 2.5 hours. 250 mL of ethyl acetate and 50 mL of water were added to the reaction mixture. 100 mL of 25% by mass saline and 70 mL of concentrated hydrochloric acid were added thereto, then, the organic layer was washed, and the organic layer was further washed two times with 150 mL of 25% by mass saline. The organic layer was dried over anhydrous magnesium sulfate, then, the residue obtained by distilling off the solvent under reduced pressure was purified by silica gel column chromatography (hexane/ethyl acetate=75/25), whereby 31 g of a compound 14-1 was obtained.

$^1$H-NMR(CDCl$_3$) δ value: 8.15-7.24(m,18H), 6.88(d,1H, J=3.6 Hz), 6.08(dd,1HJ=3.0 Hz,10.8 Hz), 6.02(dd,1H,J=6.0 Hz,10.8 Hz), 5.91(dd,1H,J=1.2 Hz,3.0 Hz), 5.91(dd,1H, J=1.2 Hz,3.0 Hz), 4.64(q,1H,J=6.3 Hz), 1.32(d,1H,J=6.6 Hz)

(2)

15.3 mL of a 30% hydrogen bromide/acetic acid solution was added to a solution of 15.12 g of the compound 14-1 in 15 mL of acetic acid, and the resultant product was stirred for 1.5 hours. 300 mL of toluene was added to the reaction mixture, and 211 g of a 36% by mass sodium hydroxide aqueous solution was added dropwise thereto at 0° C. to 10° C. 300 mL of cold water was added thereto, then, 200 mL of a 7.5% by mass sodium hydrogen carbonate aqueous solution was added dropwise thereto, followed by stirring, and the aqueous layer was removed. The organic layer was washed with 300 mL of a 7.5% by mass sodium hydrogen carbonate aqueous solution, and further washed with 300 mL of 25% by mass saline. The solvent was distilled off under reduced pressure, whereby 13.46 g of a compound 14-2 was obtained.

$^1$H-NMR(CDCl$_3$) δ value: 8.10-7.19(m,15H), 6.94(d,1H, J=3.9 Hz), 6.01(dd,1H,J=3.3 Hz,10.5 Hz), 5.84(dd,1H,J=0.9 Hz, 3.3 Hz), 5.62(dd,1H,J=3.9 Hz,10.5 Hz), 4.69(q,1H, J=6.6 Hz), 1.36(d,1H,J=6.6 Hz)

(3)

5.6 mL of water and 11.34 g of silver carbonate were added to a solution of 13.46 g of the compound 14-2 in 140 mL of acetone, and the resultant was stirred at room temperature for 1.5 hours. The silver carbonate was separated from the reaction mixture by filtration, and the solvent was distilled off under reduced pressure. The obtained residue was purified by silica gel chromatography (hexane/ethyl acetate=67/33), and as a result, the compound was a mixture of an isomer A and an isomer B, and the ratio (A:B) thereof was 4:1. 6.83 g of a compound 14-3 was obtained.

$^1$H-NMR(CDCl$_3$) δ value: 8.13-7.22(m,15H+15H,A+B), 6.02(dd,1H,J=303 Hz,105 Hz), 5.79-5.65(m,3H+4H,A+B), 4.99(t,1H,J=8.4 Hz,B), 4.68(q,1H,J=7.2 Hz,A), 3.89(d,1H, J=8.7 Hz,B), 2.99(dd,1H,J=1.2 Hz,3.3 Hz,A), 1.37(d,3H, J=6.3 Hz,B), 1.37(d,3H,J=6.3 Hz,B), 1.28(d,3H,J=6.6 Hz,A), (4)

7 mL of acetonitrile, 5.80 mL of pyridine, and 2.40 g of O-methylhydroxylamine hydrochloride were added to a solution of 6.83 g of the compound 14-3 in 35 mL of methanol, the resultant product was stirred at 50° C. for 3 hours. 100 mL of ethyl acetate was added to the reaction mixture, and the organic layer was washed with 10 mL of 6 mol/L hydrochloric acid and 90 mL of 25% by mass saline and further washed two times with 100 mL of 25% by mass saline. After the organic layer was dried over anhydrous magnesium sulfate, the solvent was distilled off under reduced pressure, whereby 7.25 g of a compound 14-4 was obtained. As a result of $^1$H-NMR measurement, the above-obtained compound was a mixture of an isomer A and an isomer B, and the ratio (A:B) thereof was 3:1.

$^1$H-NMR(CDCl$_3$) δ value: 8.13-7.21(m,16H,15H,A+B), 6.68(d,1H,J=4.8 Hz,B), 6.35-5.49(m,3H+3H,A+B), 4.15-4.03(m,1H+1H A+B), 3.94(s,1H,B), 3.67(s,1H,A), 1.35(d, 1H,J=6.6 Hz,B), 1.20(d,1H,J=6.3 Hz,A)

(5)

2.83 mL of 1-methylimidazole was added dropwise to a solution of 7.25 g of the compound 14-4 and 5.62 g of 2,4,5-trichlorobenzenesulfonyl chloride in 70 mL of acetonitrile at 0° C. to 5° C., and the resultant product was stirred at room temperature for 4 hours. 200 mL of ethyl acetate and 5 mL of concentrated hydrochloric acid were added to the reaction mixture, and the resultant product was washed with 200 mL of 10% by mass saline. After the white solid precipitated when washing was separated by filtration, the organic layer was washed three times with 150 mL of 10% by mass saline. The organic layer was dried over anhydrous magnesium sulfate, then, the residue obtained by distilling off the solvent under reduced pressure was purified by silica gel column chromatography (hexane/ethyl acetate=80/20), whereby 7.73 g of a compound 14-5 was obtained. As a result of $^1$H-NMR measurement, the above-obtained compound was a mixture of an isomer A and an isomer B, and the ratio (A:B) thereof was 2:1.

$^1$H-NMR(CDCl$_3$) δ value: 8.01-7.21(m,18H+17H,A+B), 6.71(d,1H,J=3.0 Hz,B), 6.43-6.40(m,1H,B), 5.98-5.27(m, 4H+3H,A+B), 3.91(s,3H,B), 3.37(s,3H,A), 1.63(d,3H,J=6.3 Hz,B), 1.56(d,3H,J=6.6 Hz,A)

(6)

1.85 g of lithium bromide was added to a solution of 7.73 g of the compound 14-5 in 50 mL of 1,3-dimethyl-2-imidazolidinone, and the resultant product was stirred at 50° C. for 3 hours. 200 mL of ethyl acetate, 200 mL of water, and 10 mL of 25% by mass saline were added to the reaction mixture, and the resultant product was washed. The organic layer was further washed with 200 mL of 25% by mass saline, and dried over anhydrous magnesium sulfate. The solvent was distilled off under reduced pressure, whereby 5.49 g of a compound 14-6 was obtained. As a result of $^1$H-NMR measurement, the above-obtained compound was a mixture of an isomer A and an isomer B, and the ratio (A:B) thereof was 3:1.

$^1$H-NMR(CDCl$_3$) δ value: 8.06-7.34(m,16H+15H,A+B), 6.72(d,1H,J=5.4 Hz,B), 6.47-5.32(m,3H+3H,A+B), 4.55-4.45(m,1H+1H,A+B), 3.97(s,3H,B), 3.75(s,3H,A), 1.86(d, 3H,J=6.6 Hz A), 1.71(d,3H,J=6.9 Hz,B)

(7)

1.10 mL of 2 mol/L hydrochloric acid was added to a mixture of 4.99 g of the compound 14-6, 6.60 mL of a 37% formalin aqueous solution, and 45 mL of acetone, and the resultant product was stirred at 50° C. for 2.5 hours. 150 mL of ethyl acetate and 150 mL of 25% by mass saline were added to the reaction mixture, and the organic layer was washed and further washed two times with 150 mL of 25% by mass saline. After the organic layer was dried over anhydrous sodium sulfate, the solvent was distilled off under reduced pressure, whereby 4.7 g of a compound 14-7 was obtained. A part of the obtained residue was purified by silica gel column chromatography (hexane/ethyl acetate=67/33), and as a result, the compound was a mixture of an isomer A and an isomer B, and the ratio (A:B) thereof was 2:1.

$^1$H-NMR(CDCl$_3$) δ value: 9.68(s,1H,B), 9.66(s,1H,A), 9.68-7.93(m,6H+6H,A+B), 7.65-7.4(m,9H+9H,A+B), 6.23 (dd,1H,J=2.1 Hz,6.6 Hz,A), 6.15(dd,1H,J=1.5 Hz,8.4 Hz,B), 5.98-5.94(m,1H+1H,A+B), 5.72(d,1H,J=2.1 Hz,A), 5.64(d, 1H,J=1.8 Hz,B), 5.71-4.44(m,1H+1H,A+B), 1.85(d,1H, J=6.9 Hz,A), 1.75(d, 1H,J=7.2 Hz,B)

(8)

7.33 g of a 15% sodium hydrogen sulfide aqueous solution was added to a solution of 2.35 g of the compound 14-7 in 25 mL of N,N-dimethylformamide at −5° C. to 0° C., and the resultant product was stirred for 1 hour. 150 mL of ethyl acetate and 100 mL of 10% by mass saline were added to the reaction mixture, followed by stirring, and the aqueous layer was removed. The organic layer was washed three times with 100 mL of a 7.5% by mass sodium hydrogen carbonate aqueous solution, and further washed with 25% by mass saline. After the organic layer was dried over anhydrous magnesium sulfate, the solvent was distilled off under reduced pressure. The obtained residue was purified by silica gel column chromatography (hexane/ethyl acetate=75/25), whereby 0.78 g of a compound 14-8 was obtained.

$^1$H-NMR(CDCl$_3$) δ value: 8.16-7.76(m,6H), 7.63-7.20 (m,9H), 6.05(dd,1H,J=1.8 Hz,10.5 Hz), 5.98(dd,1H,J=1.5 Hz,2.7 Hz), 5.76(dd,1H,J=2.7 Hz,10.5 Hz), 5.40(t,1H,J=2.1 Hz), 4.00(dq, 1H,J=1.2 Hz,7.2 Hz) 2.57(d,1H,J=1.5 Hz), 1.29(d,3H,J=7.2 Hz)

Although the present invention has been described with the embodiments thereof, unless otherwise particularly described, the present invention is not intended to be limited in any details of description of the present invention, and it is considered that the present invention must be broadly interpreted without departing from the spirit and the scope of the present invention shown in the appended claims.

What is claimed is:

1. A production method of a thiopyranose compound represented by the following Formula (2) by reacting a compound represented by the following Formula (1) with hydrogen sulfide or a salt thereof,

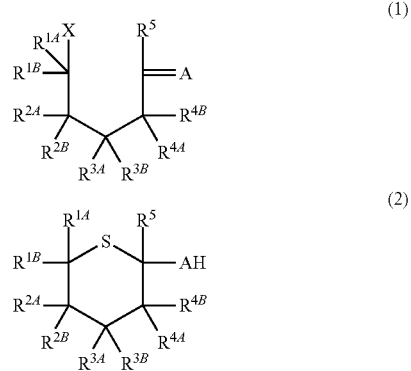

wherein X represents a leaving group selected from a group consisting of a halogen atom, a $C_{1-6}$ alkylsulfonyloxy group, and a $C_{6-20}$ arylsulfonyloxy group, A represents an oxygen atom or a sulfur atom, $R^{1A}$ and $R^{1B}$ are the same as or different from each other, and each of $R^{1A}$ and $R^{1B}$ represents a hydrogen atom, a hydroxyl group, a carboxyl group, a $C_{1-6}$ alkyl group, a $C_{2-6}$ alkenyl group, a $C_{2-6}$ alkynyl group, a $C_{6-20}$ aryl group, or a $C_{2-20}$ heterocyclic group, wherein at least one of $R^{1A}$ and $R^{1B}$ is a group other than a hydroxyl group, $R^5$ represents a hydrogen atom, $R^{2A}$ to $R^{4A}$ and $R^{2B}$ to $R^{4B}$ are the same as or different from each other, and each of $R^{2A}$ to $R^{4A}$ and $R^{2B}$ to $R^{4B}$ represents a hydrogen atom, a hydroxyl group, a halogen atom, a cyano group, an azido group, an amino group, a carboxyl group, $-OR^{OH}$, a $C_{1-6}$ alkyl group, a $C_{2-6}$ alkenyl group, a $C_{2-6}$ alkynyl group, a $C_{1-6}$ alkoxy group, a $C_{2-6}$ alkenyloxy group, a $C_{1-6}$ alkylthio group, a $C_{6-20}$ aryl group, a $C_{6-20}$ aryloxy group, a $C_{6-20}$ arylthio group, a $C_{1-20}$ acyloxy group, a $C_{1-20}$ acylimino group, a $C_{3-20}$ silyloxy group, a $C_{2-20}$ heterocyclic group, a $C_{2-20}$ heterocyclic oxy group, or a $C_{2-20}$ heterocyclic thio group, each pair of $R^{2A}$ and $R^{2B}$, $R^{3A}$ and $R^{3B}$, and $R^{4A}$ and $R^{4B}$ may be bonded to form a $C_{1-6}$ alkylidene group, two of $R^{1A}$ to $R^{4A}$ and $R^{1B}$ to $R^{4B}$ may be bonded to each other to form a group represented by $-O-Y^1-O-$, each of $R^{1A}$ to $R^{4A}$ and $R^{1B}$ to $R^{4B}$ may have a substituent or a protecting group selected from a group consisting of a hydroxyl protecting group, an amino protecting group, and a carboxyl protecting group, $R^{OH}$ represents a hydroxyl protecting group, and $Y^1$ represents a $C_{1-6}$ alkylene group or a $C_{2-20}$ silylene group, wherein the substituent is selected from the following substituent group A and substituent group B:

substituent group A: a halogen atom, a cyano group, a nitro group, an amino group, a hydroxyl group, a carboxyl group, a carbamoyl group, a sulfamoyl group, a $C_{1-6}$ alkyl group, a $C_{2-6}$ alkenyl group, a $C_{2-6}$ alkynyl group, a $C_{3-8}$ cycloalkyl group, a $C_{6-20}$ aryl group, a $C_{1-6}$ alkoxy group, a $C_{6-20}$ aryloxy group, a $C_{1-20}$ acyl group, a $C_{1-20}$ acyloxy group, a $C_{1-20}$ acylamino group, a $C_{1-6}$ alkoxycarbonyl group, a $C_{6-20}$ aryloxycarbonyl group, a $C_{1-6}$ alkoxycarbonyloxy group, a $C_{1-6}$ alkylamino group, a di($C_{1-6}$ alkyl)amino group, a $C_{1-6}$ alkylthio group, a $C_{1-6}$ alkylsulfonyl group, a $C_{6-20}$ arylsulfonyl group, a $C_{1-6}$ alkylsulfonyloxy group, a $C_{6-20}$ arylsulfonyloxy group, a $C_{1-18}$ silyl group, a $C_{2-20}$ heterocyclic group, and an oxo group, and substituent group B: a halogen atom, a cyano group, a nitro group, an amino group, a hydroxyl group, a carboxyl group, a $C_{1-6}$ alkyl group, a $C_{6-20}$ aryl group, a $C_{1-6}$ alkoxy group, a $C_{2-20}$ heterocyclic group, and an oxo group.

2. The production method of a thiopyranose compound according to claim 1, wherein $R^{1A}$ to $R^{4A}$, $R^{1B}$ to $R^{4B}$, $R^5$, and X in the above formulas are selected from the following list, and

TABLE 1

| | |
|---|---|
| $R^{1A}$ | Hydrogen atom, |
| $R^{1B}$ | $C_{1-6}$ alkyl group, $C_{2-6}$ alkenyl group, $C_{6-20}$ aryl group, $C_{2-20}$ heterocyclic group, $C_{1-6}$ alkoxy $C_{1-6}$ alkyl group, $C_{6-20}$ aryloxy $C_{1-6}$ alkyl group, $C_{6-20}$ aryl $C_{1-6}$ alkyloxy $C_{1-6}$ alkyl group, $C_{2-6}$ alkanoyloxy $C_{1-6}$ alkyl group, $C_{7-20}$ aroyloxy $C_{1-6}$ alkyl group, $C_{3-20}$ silyloxy $C_{1-6}$ alkyl group |
| $R^{2A}$ | Hydrogen atom, hydroxyl group, |
| $R^{2B}$ | $C_{1-6}$ alkyl group, $C_{2-6}$ alkenyl group, $C_{6-20}$ aryl group, $C_{2-20}$ heterocyclic group, $C_{1-6}$ alkoxy group, $C_{2-6}$ alkenyloxy group, $C_{6-20}$ aryloxy group, $C_{6-20}$ aryl $C_{1-6}$ alkyloxy group, $C_{2-6}$ alkanoyloxy group, |
| $R^{3A}$ | |
| $R^{3B}$ | |
| $R^{4A}$ | $C_{7-20}$ aroyloxy group, $C_{3-20}$ silyloxy group, azido group, halogen atom, |
| $R^{4B}$ | $C_{1-20}$ acylimino group |
| $R^5$ | Hydrogen atom, |
| X | Halogen atom, $C_{1-6}$ alkylsulfonyloxy group, $C_{6-20}$ arylsulfonyloxy group | wherein two adjacent alkoxy groups of $R^{1A}$ to $R^{4A}$ may be linked to form $-O-Y^1-O-$, each of $R^{1A}$ to $R^{4A}$ and $R^{1B}$ to $R^{4B}$ may have a substituent selected from the substituent groups A and B, Substituent group A: a halogen atom, a cyano group, a nitro group, an amino group, a hydroxyl group, a carboxyl group, a carbamoyl group, a sulfamoyl group, a $C_{1-6}$ alkyl group, a $C_{2-6}$ alkenyl group, a $C_{2-6}$ alkynyl group, a $C_{3-8}$ cycloalkyl group, a $C_{6-20}$ aryl group, a $C_{1-6}$ alkoxy group, a $C_{6-20}$ aryloxy group, a $C_{1-20}$ acyl group, a $C_{1-20}$ acyloxy group, a $C_{1-20}$ acylamino group, a $C_{1-6}$ alkoxycarbonyl group, a $C_{6-20}$ aryloxycarbonyl group, a $C_{1-6}$ alkoxycarbonyloxy group, a $C_{1-6}$ alkylamino group, a di($C_{1-6}$ alkyl)amino group, a $C_{1-6}$ alkylthio group, a $C_{1-6}$ alkylsulfonyl group, a $C_{6-20}$ arylsulfonyl group, a $C_{1-6}$ alkylsulfonyloxy group, a $C_{6-20}$ arylsulfonyloxy group, a $C_{1-18}$ silyl group, a $C_{2-20}$ heterocyclic group, and an oxo group, the substituent group A may be substituted with the following substituent group B, the hydroxyl group, the amino group, and the carboxyl group in the substituent group A may be protected, Substituent group B: a halogen atom, a cyano group, a nitro group, an amino group, a hydroxyl group, a carboxyl group, a $C_{1-6}$ alkyl group, a $C_{6-20}$ aryl group, a $C_{1-6}$ alkoxy group, a $C_{2-20}$ heterocyclic group, and an oxo group, and the above-described substituents may be further substituted with a group in the substituent group B.

3. The production method of a thiopyranose compound according to claim 1, wherein A in the above formulas is an oxygen atom.

4. The production method of a thiopyranose compound according to claim 1,
wherein each of $R^{2A}$ to $R^{4A}$ and $R^{2B}$ to $R^{4B}$ in the above formulas is independently a hydrogen atom or $OR^{OH}$.

5. The production method of a thiopyranose compound according to claim 1,
wherein $R^{1B}$, $R^{2B}$, $R^{3B}$, to $R^{4B}$ in the above formulas are hydrogen atoms.

6. The production method of a thiopyranose compound according to claim 1,
wherein the sulfur compound is sodium hydrogen sulfide.

7. The production method of a thiopyranose compound according to claim 1,
wherein $R^{2A}$, $R^{3A}$, and $R^{4A}$ in the above formulas are $OR^{OH}$'s.

8. The production method of a thiopyranose compound according to claim 1,
wherein $R^{1A}$ in the above formulas is a hydrogen atom, a methyl group, or $CH_2OR^{OH}$.

9. The production method of a thiopyranose compound according to claim 1,
wherein X in the above formula is a $C_{1-6}$ alkylsulfonyloxy group or a $C_{6-20}$ arylsulfonyloxy group.

10. The production method of a thiopyranose compound according to claim 1,
wherein X in the above formula is a halogen atom.

11. The production method of a thiopyranose compound according to claim 1,
wherein a reaction of the compound represented by Formula (1) with the sulfur compound is performed in an aprotic polar solvent.

12. The production method of a thiopyranose compound according to claim 1,
wherein a reaction of the compound represented by Formula (1) with the sulfur compound is performed in a protic polar solvent.

13. The production method of a thiopyranose compound according to claim 1,
wherein $R^{1A}$ in the above formulas is a hydrogen atom, a methyl group, or $CH_2OR^{OH}$, and $R^{2A}$ in the above formulas is a hydrogen atom.

14. The production method of a thiopyranose compound according to claim 1,
wherein the compound represented by Formula (2) is a compound represented by any one of the following Formulas (2-1) to (2-6), and

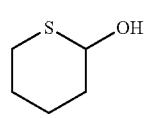
(2-1)

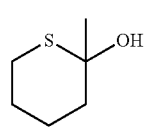
(2-2)

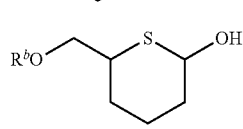
(2-3)

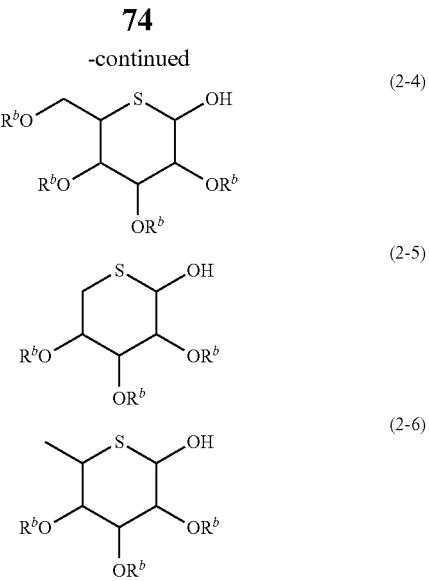
(2-4)

(2-5)

(2-6)

wherein $R^b$ represents a $C_{2-6}$ alkanoyl group, a $C_{7-20}$ aroyl group, or a $C_{6-20}$ aryl $C_{1-6}$ alkyl group.

15. The production method of a thiopyranose compound according to claim 14,
wherein $R^b$ in Formulas (2-4) to (2-6) is a $C_{2-6}$ alkanoyl group or a $C_{7-20}$ aroyl group.

16. The production method of a thiopyranose compound according to claim 15,
wherein $R^b$ in Formulas (2-4) to (2-6) is an acetyl group or a benzoyl group.

17. The production method of a thiopyranose compound according to claim 1,
wherein the compound represented by Formula (2) is a compound represented by any one of the following Formulas (3-1) to (3-5), and

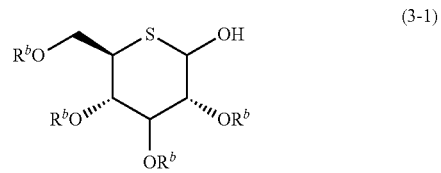
(3-1)

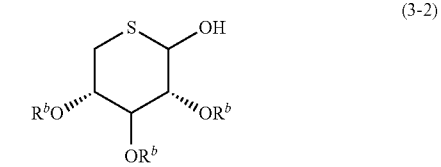
(3-2)

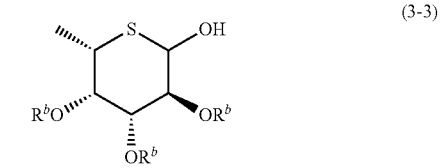
(3-3)

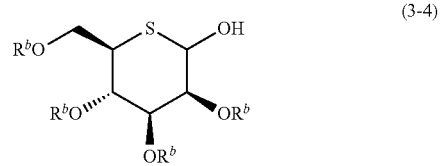
(3-4)

-continued

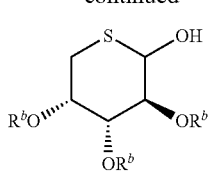
(3-5)

wherein $R^b$ represents a benzoyl group.

18. The production method of a thiopyranose compound according to claim 1,
wherein the hydroxyl protecting group $R^{OH}$ is a $C_{7-20}$ aroyl group having a molecular weight of 106 or greater.

19. The production method of a thiopyranose compound according to claim 1,
wherein the compound represented by Formula (2) is synthesized through the following synthetic route (i) comprising:
synthesizing a compound represented by Formula (D) as the compound represented by Formula (1) from a compound represented by the following Formula (A) through a compound represented by the following Formula (C); and
reacting the compound represented by Formula (D) and hydrogen sulfide or a salt thereof, thereby to obtain a compound represented by Formula (E) as the compound represented by Formula (2):

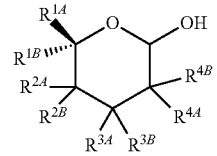
(A)

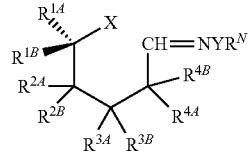
(C)

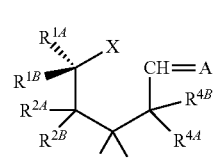
(D)

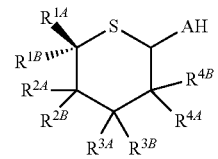
(E)

wherein $R^{1A}$ to $R^{4A}$, $R^{1B}$ to $R^{4B}$, and A have the same meanings as those in Formula (1), here, X is a halogen atom, Y represents an oxygen atom or $NR^N$, $R^N$'s are the same as or different from each other, and $R^N$ represents a hydrogen atom, a $C_{1-6}$ alkyl group, a $C_{6-20}$ aryl $C_{1-6}$ alkyl group, or a $C_{6-20}$ aryl group.

20. The production method of a thiopyranose compound according to claim 1,
wherein the compound represented by Formula (2) is synthesized through the following synthetic route (ii) comprising:
synthesizing a compound represented by Formula (D) as the compound represented by Formula (1) from the compound represented by the following Formula (A) through a compound represented by the following Formula (C'), and further through a compound represented by the following Formula (C); and
reacting the compound represented by Formula (D) and hydrogen sulfide or a salt thereof, thereby to obtain a compound represented by Formula (E) as the compound represented by Formula (2):

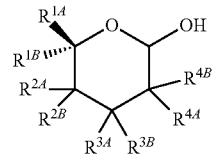
(A)

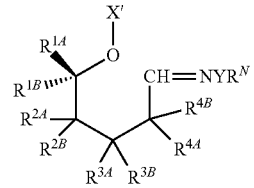
(C')

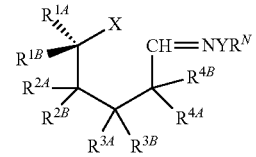
(C)

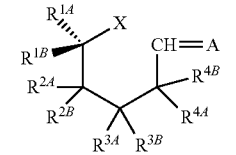
(D)

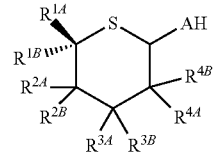
(E)

wherein $R^{1A}$ to $R^{4A}$, $R^{1B}$ to $R^{4B}$, and A have the same meanings as those in Formula (1), here, X is a halogen atom, X' is a $C_{1-6}$ alkylsulfonyl group or a $C_{6-20}$ arylsulfonyl group, Y represents an oxygen atom or $NR^N$, $R^N$'s are the same as or different from each other, and $R^N$ represents a hydrogen atom, a $C_{1-6}$ alkyl group, a $C_{6-20}$ aryl $C_{1-6}$ alkyl group, or a $C_{6-20}$ aryl group.

21. The production method of a thiopyranose compound according to claim 1,
wherein the compound represented by Formula (2) is synthesized through the following synthetic route (iii) comprising:
synthesizing a compound represented by Formula (D') as the compound represented by Formula (1) from the compound represented by the following Formula (A) through a compound represented by the following Formula (C'); and reacting the compound represented by Formula (D') and hydrogen sulfide or a salt thereof, thereby to obtain a compound represented by Formula (E') as the compound represented by Formula (2):

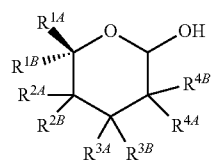
(A)

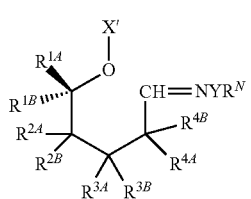
(C')

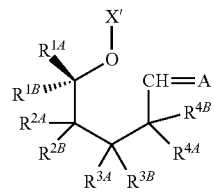
(D')

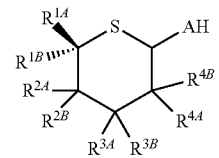
(E)

wherein $R^{1A}$ to $R^{4A}$, $R^{1B}$ to $R^{4B}$, and A have the same meanings as those in Formula (1), X' is a $C_{1-6}$ alkylsulfonyl group or a $C_{6-20}$ arylsulfonyl group, Y represents an oxygen atom or $NR^N$, $R^N$'s are the same as or different from each other, and $R^N$ represents a hydrogen atom, a $C_{1-6}$ alkyl group, a $C_{6-20}$ aryl $C_{1-6}$ alkyl group, or a $C_{6-20}$ aryl group.

* * * * *